US008715276B2

(12) United States Patent
Thompson et al.

(10) Patent No.: US 8,715,276 B2
(45) Date of Patent: May 6, 2014

(54) METHODS AND APPARATUS FOR TREATMENT OF HOLLOW ANATOMICAL STRUCTURES

(75) Inventors: Russell B. Thompson, Los Altos, CA (US); Fiona M. Sander, Los Altos Hills, CA (US); Chris Scott Jones, Menlo Park, CA (US)

(73) Assignee: Covidien LP, Mansfield, MA (US)

( * ) Notice: Subject to any disclaimer, the term of this patent is extended or adjusted under 35 U.S.C. 154(b) by 828 days.

(21) Appl. No.: 12/264,170

(22) Filed: Nov. 3, 2008

(65) Prior Publication Data

US 2009/0125009 A1 May 14, 2009

Related U.S. Application Data

(62) Division of application No. 11/222,069, filed on Sep. 8, 2005, now abandoned.

(60) Provisional application No. 60/608,335, filed on Sep. 9, 2004, provisional application No. 60/617,621, filed on Oct. 8, 2004, provisional application No. 60/618,827, filed on Oct. 13, 2004, provisional application No. 60/621,251, filed on Oct. 22, 2004, provisional application No. 60/624,009, filed on Nov. 1, 2004, provisional application No. 60/645,964, filed on Jan. 21, 2005, provisional application No. 60/659,287, filed on Mar. 7, 2005, provisional application No. 60/664,316, filed on Mar. 22, 2005.

(51) Int. Cl.
*A61B 18/04* (2006.01)

(52) U.S. Cl.
USPC .......................................................... 606/27

(58) Field of Classification Search
CPC ...... A61B 18/04; A61B 18/08; A61B 18/082; A61B 2018/00005; A61B 2018/00011; A61B 2018/00065; A61B 2018/00404; A61B 2018/00625; A61B 2018/00946; A61B 2018/046
USPC ...................................................... 606/32–50
See application file for complete search history.

(56) References Cited

U.S. PATENT DOCUMENTS

| 4,682,596 | A |   | 7/1987  | Bales et al. |
|-----------|---|---|---------|--------------|
| 4,968,306 | A | * | 11/1990 | Huss et al. ................. 604/264 |
| 5,122,138 | A |   | 6/1992  | Manwaring |
| 5,188,602 | A |   | 2/1993  | Nichols |
| 5,304,171 | A |   | 4/1994  | Gregory et al. |
| 5,336,178 | A |   | 8/1994  | Kaplan et al. |
| 5,433,708 | A |   | 7/1995  | Nichols et al. |
| 5,505,730 | A |   | 4/1996  | Edwards |

(Continued)

FOREIGN PATENT DOCUMENTS

| WO | WO 94/07446   | 4/1994 |
|----|---------------|--------|
| WO | WO 2006/059793 | 6/2006 |

*Primary Examiner* — Ronald Hupczey, Jr.
(74) *Attorney, Agent, or Firm* — Thomas M. Johnston, Esq.

(57) ABSTRACT

One embodiment comprises an apparatus for applying energy to a hollow anatomical structure having an inner wall. The apparatus comprises an elongate shaft having a distal end and a proximal end opposite the distal end; and a capacitive treatment element located near the distal end. The capacitive treatment element is sized for insertion into the hollow anatomical structure and placement near the inner wall. The capacitive treatment element is configured to create an electric field that extends at least partially into the inner wall. Other devices and methods for treatment of hollow anatomical structures are disclosed as well.

32 Claims, 45 Drawing Sheets

(56) References Cited

U.S. PATENT DOCUMENTS

| | | |
|---|---|---|
| 5,514,130 A | 5/1996 | Baker |
| 5,542,928 A | 8/1996 | Evans et al. |
| 5,827,268 A | 10/1998 | Laufer |
| 5,964,752 A | 10/1999 | Stone |
| 6,033,383 A | 3/2000 | Ginsburg |
| 6,047,700 A | 4/2000 | Eggers et al. |
| 6,156,036 A | 12/2000 | Sussman et al. |
| 6,669,694 B2 | 12/2003 | Shadduck |
| 6,719,738 B2 | 4/2004 | Mehier |
| 6,802,838 B2 | 10/2004 | Loeb et al. |
| 6,911,028 B2 | 6/2005 | Shadduck |
| 7,077,836 B2 | 7/2006 | Lary et al. |
| 7,137,977 B2 | 11/2006 | Brucker et al. |
| 7,163,533 B2 | 1/2007 | Hobbs et al. |
| 7,184,827 B1 | 2/2007 | Edwards |
| 7,311,708 B2 | 12/2007 | McClurken |
| 7,524,316 B2 * | 4/2009 | Hennings et al. ............ 606/7 |
| 2001/0034503 A1 | 10/2001 | Mehier |
| 2002/0068866 A1 * | 6/2002 | Zikorus et al. ............ 600/424 |
| 2002/0177846 A1 * | 11/2002 | Mulier et al. ............ 606/27 |
| 2003/0109869 A1 | 6/2003 | Shadduck |
| 2004/0010248 A1 | 1/2004 | Appling et al. |
| 2004/0068306 A1 | 4/2004 | Shadduck |
| 2004/0092913 A1 | 5/2004 | Hennings et al. |
| 2004/0199226 A1 | 10/2004 | Shadduck |
| 2004/0254532 A1 | 12/2004 | Mehier |
| 2005/0070886 A1 | 3/2005 | Maglione et al. |
| 2005/0113798 A1 * | 5/2005 | Slater et al. ............ 604/508 |
| 2005/0288655 A1 | 12/2005 | Root et al. |
| 2007/0032785 A1 | 2/2007 | Diederich et al. |
| 2008/0132826 A1 | 6/2008 | Shadduck |
| 2008/0171982 A1 | 7/2008 | Mehier |
| 2008/0287939 A1 | 11/2008 | Appling et al. |

* cited by examiner

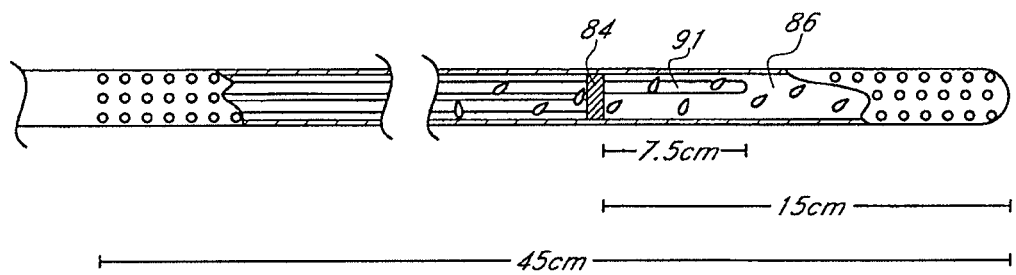
FIG. 14
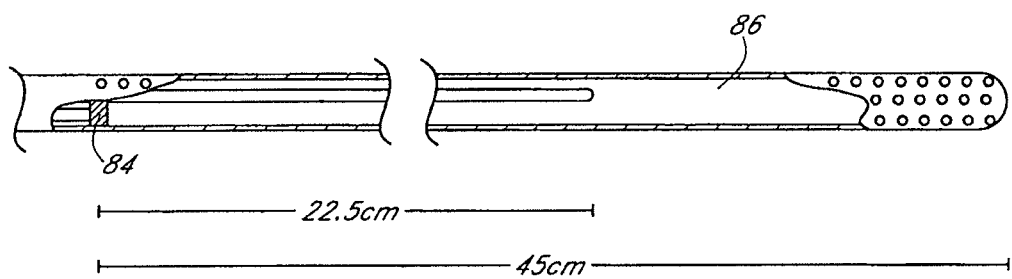
FIG. 15
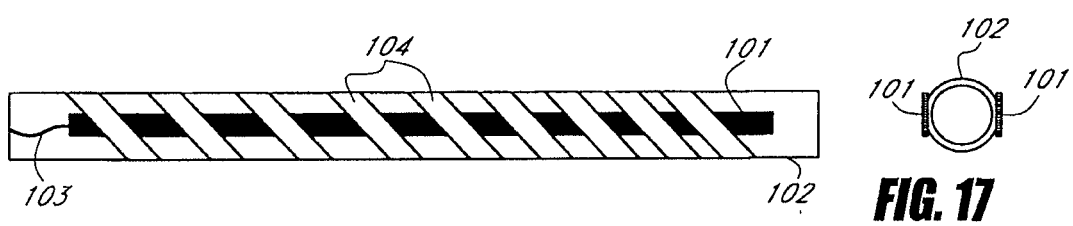
FIG. 16
FIG. 17

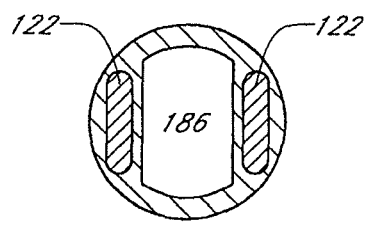
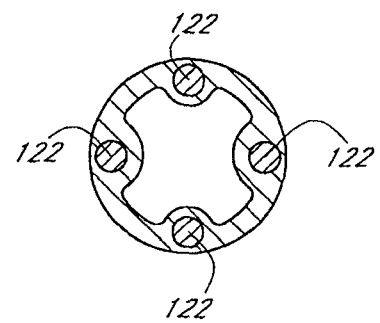
FIG. 21  FIG. 22
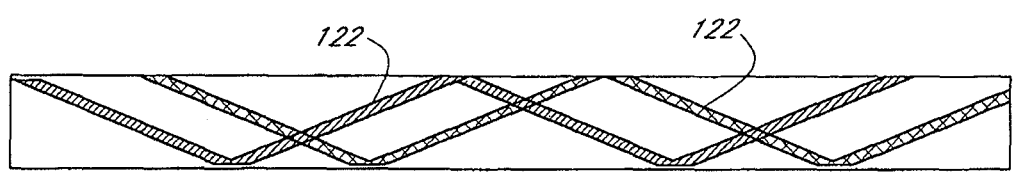
FIG. 23

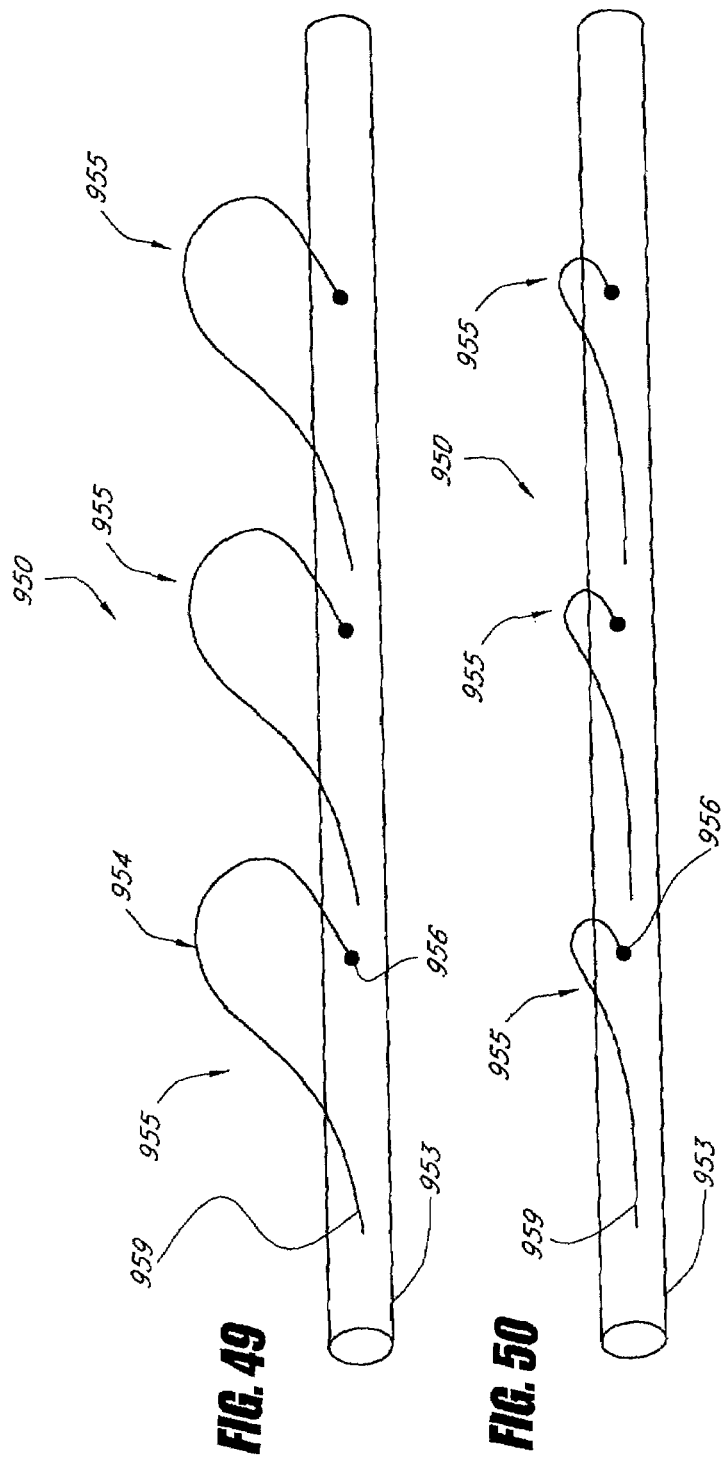

SHEATH FUNNEL

ALTERNATING POLARITY RF

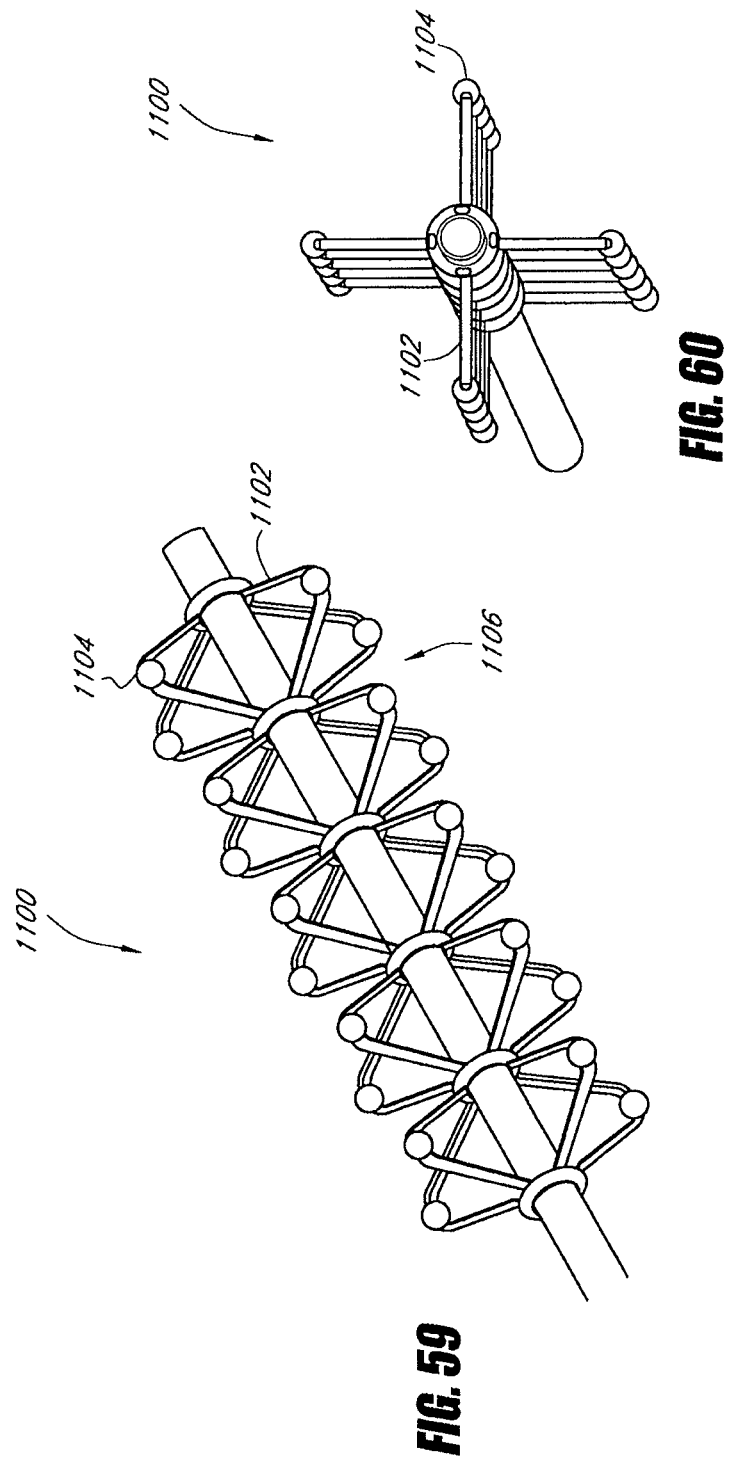

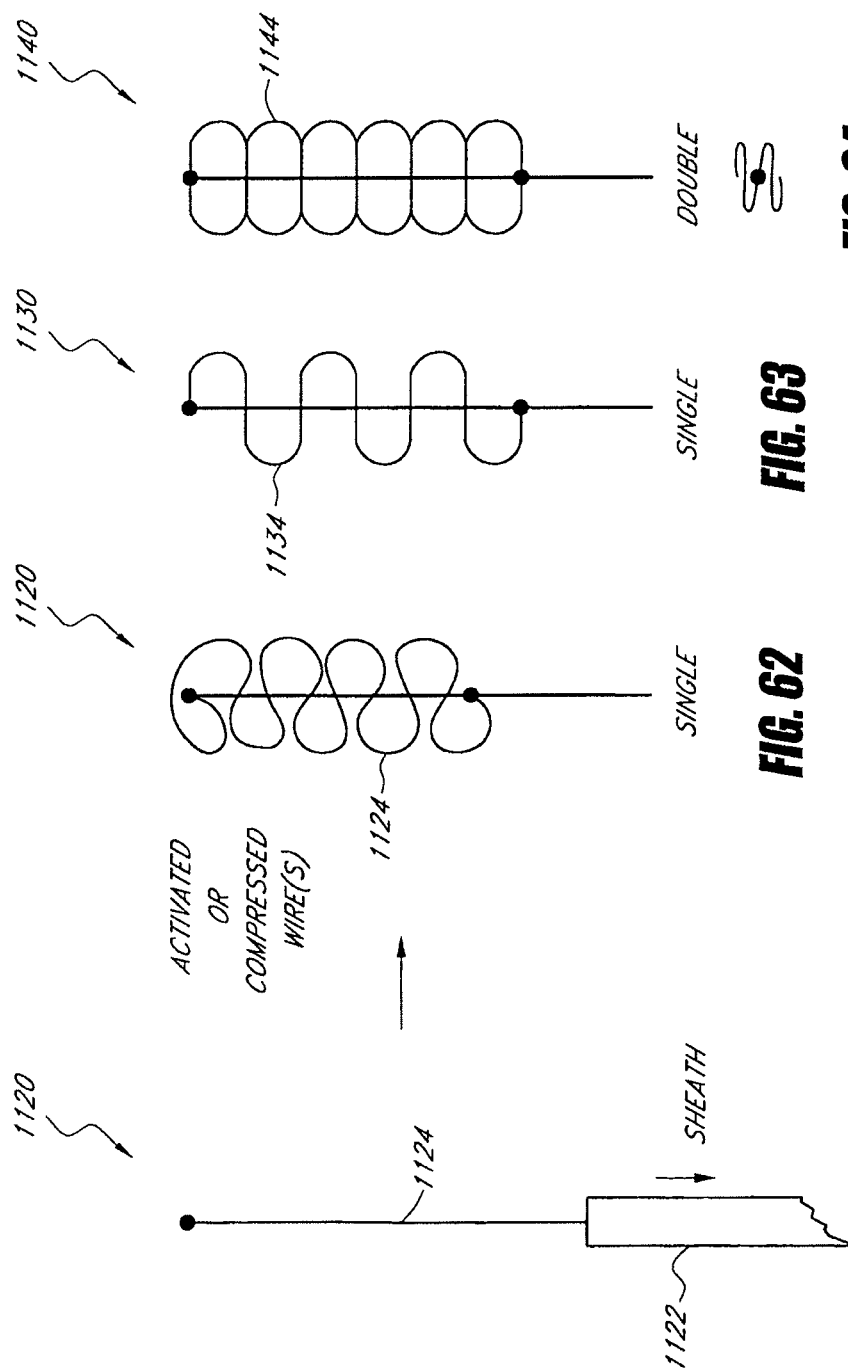

FIG. 74
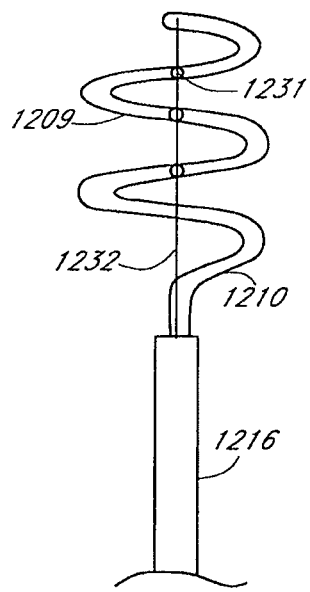
FIG. 75
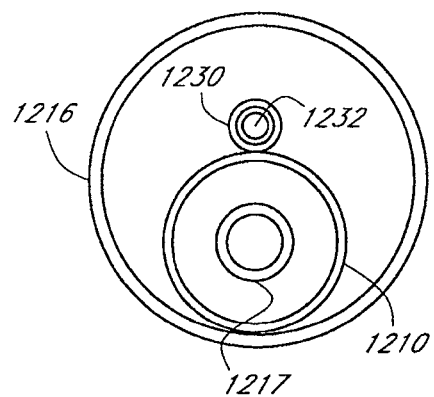
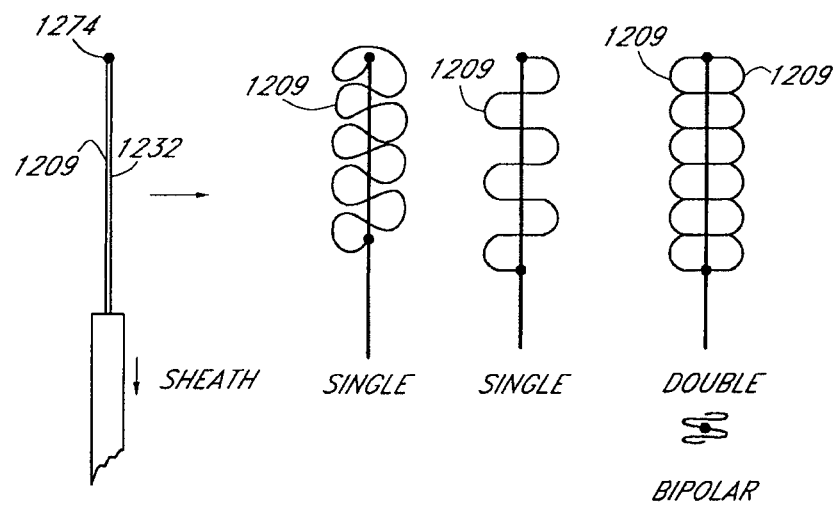
FIG. 76

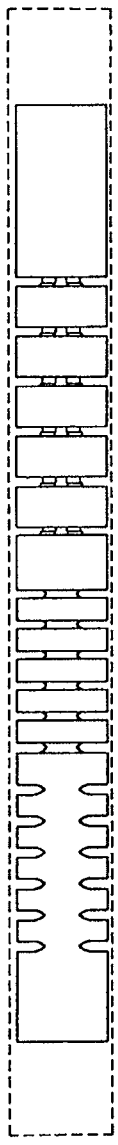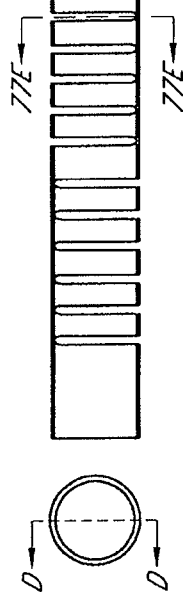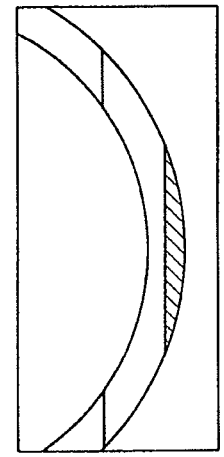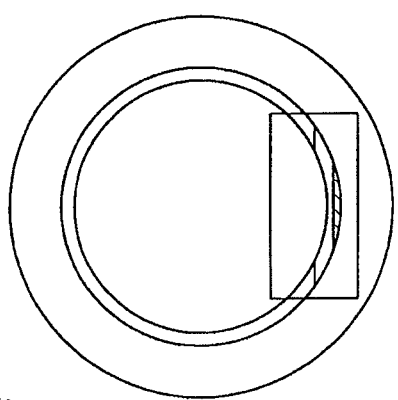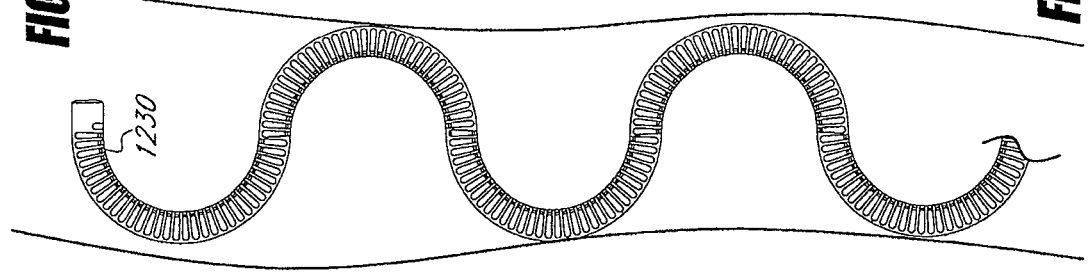
FIG. 77B
FIG. 77D
FIG. 77F
FIG. 77C
FIG. 77E
FIG. 77A

SINGLE

SINGLE

DOUBLE

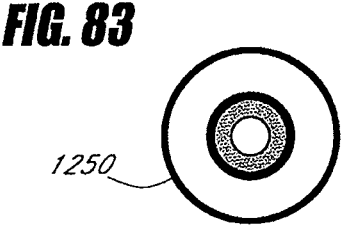
FIG. 83
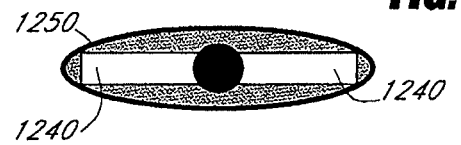
FIG. 85
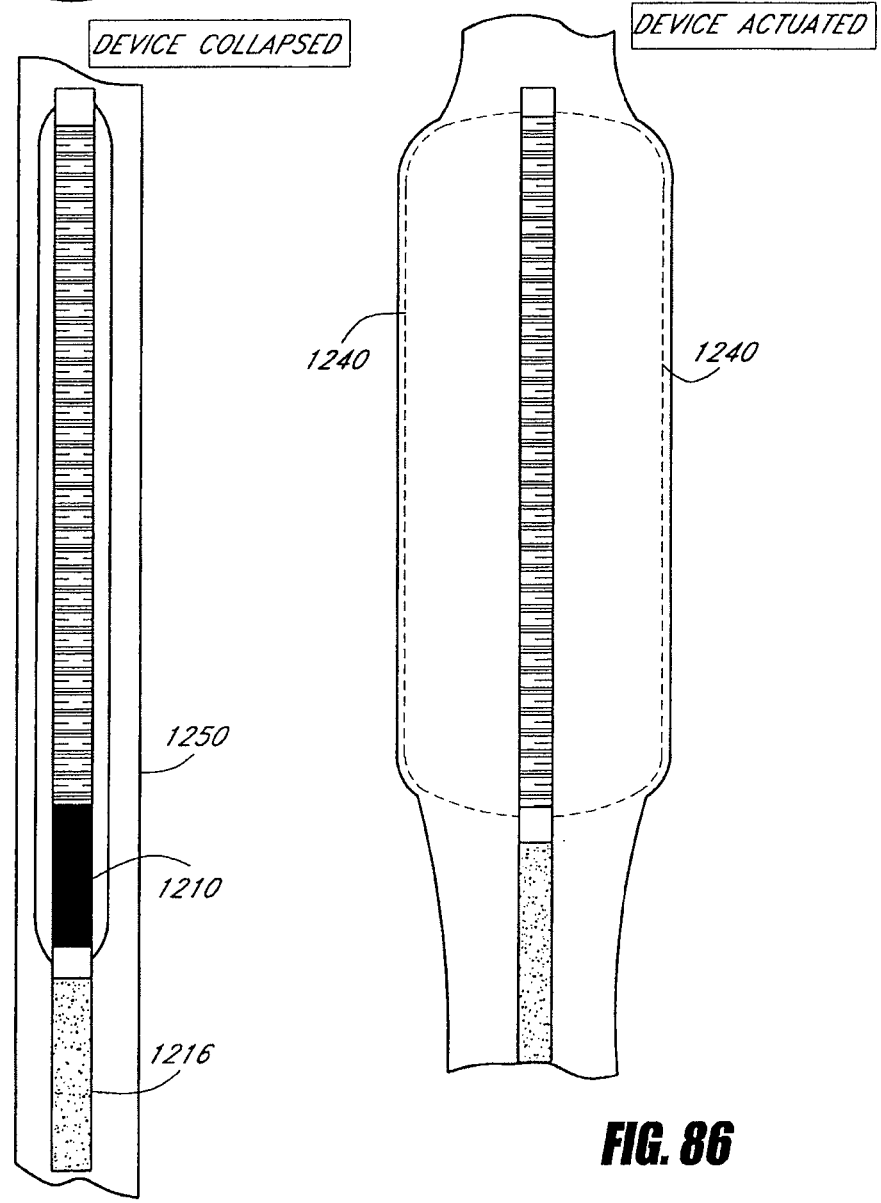
FIG. 84
FIG. 86

METHODS AND APPARATUS FOR TREATMENT OF HOLLOW ANATOMICAL STRUCTURES

RELATED APPLICATIONS; PRIORITY

This application is a divisional of application Ser. No. 11/222,069 filed Sep. 8, 2005, now abandoned, which claims the benefit under 35 U.S.C. §119(e) of each of the following U.S. Provisional Patent Applications: No. 60/608,335, filed Sep. 9, 2004, titled CATHETER WITH THERMAL ELEMENT FOR LIGATION OF HOLLOW ANATOMICAL STRUCTURES; No. 60/617,621, filed Oct. 8, 2004, titled ELECTRODE ELEMENT SYSTEMS; No. 60/618,827, filed Oct. 13, 2004, titled CATHETER WITH THERMAL ELEMENT FOR LIGATION OF HOLLOW ANATOMICAL STRUCTURES; No. 60/621,251, filed Oct. 22, 2004, titled VEIN CONFORMING CATHETER; No. 60/624,009, filed Nov. 1, 2004, titled CATHETER WITH THERMAL ELEMENT FOR LIGATION OF HOLLOW ANATOMICAL STRUCTURES; No. 60/645,964, filed Jan. 21, 2005, titled HOLLOW ANATOMIC STRUCTURE CONFORMING CATHETER; No. 60/659,287, filed Mar. 7, 2005, titled CATHETER WITH THERMAL ELEMENT FOR LIGATION OF HOLLOW ANATOMICAL STRUCTURES; and No. 60/664,316, filed Mar. 22, 2005, titled CATHETER WITH CAPACITIVE ELEMENT FOR TREATMENT OF HOLLOW ANATOMICAL STRUCTURES. The entirety of each of the above-mentioned provisional patent applications is hereby incorporated by reference herein and made a part of this specification.

BACKGROUND OF THE INVENTIONS

1. Field of the Inventions

Certain embodiments disclosed herein relate to methods and devices for treating hollow anatomical structures such as varicose veins.

2. Description of the Related Art

The human venous system of the lower extremities consists essentially of the superficial venous system and the deep venous system with perforating veins connecting the two systems. The superficial system includes the long or great saphenous vein and the small saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and allows only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional, distal valvular failure. Two venous conditions or symptoms which often result from valve failure are varicose veins and more symptomatic chronic venous insufficiency.

SUMMARY OF THE INVENTIONS

One embodiment comprises an apparatus for applying energy to a hollow anatomical structure having an inner wall. The apparatus comprises an elongate shaft having a distal end and a proximal end opposite the distal end; and a capacitive treatment element located near the distal end. The capacitive treatment element is sized for insertion into the hollow anatomical structure and placement near the inner wall. The capacitive treatment element is configured to create an electric field that extends at least partially into the inner wall.

One embodiment comprises an apparatus for applying energy to a hollow anatomical structure having an inner wall. The apparatus comprises an elongate shaft suitable for insertion into the hollow anatomical structure; and a dielectric heating element connected to the shaft.

One embodiment comprises a method of treating a hollow anatomical structure. The method comprises inserting a capacitive treatment element into the hollow anatomical structure; positioning the capacitive treatment element near an inner wall of the hollow anatomical structure; and, with the capacitive treatment element, creating an electric field that extends at least partially into the inner wall.

One embodiment is an apparatus for applying energy to a hollow anatomical structure having an inner wall. In one such embodiment, the apparatus comprises a heat emitter containing an electrically resistive fluid. The heat emitter generates heat in the resistive fluid by passing an electrical current through the fluid. The heat emitter can be positioned within a hollow anatomical structure in order to ligate a portion of the hollow anatomical structure.

An alternative embodiment of an apparatus for applying energy to a hollow anatomical structure having an inner wall comprises a heat emitter containing a heating medium that has a self-regulating maximum temperature associated with a phase change of the heating medium. The heat emitter is generally configured to be positioned within the hollow anatomical structure.

Another embodiment comprises a method of treating a hollow anatomical structure having an inner wall. The method comprises positioning a heating element in a first position in said hollow anatomical structure. The heating element has a length and a width measured orthogonal to the length. The length of the heating element is preferably greater than the width. While in a first position, the heating element is operated and emits heat from substantially all of its length. The heat is emitted into the inner wall of the hollow anatomical structure. The element is subsequently moved to a second position within the anatomical structure by a distance corresponding to approximately the structure's length. While stationary in this position, the element is again operated and again emits heat into the inner wall along substantially the length of the element. In one embodiment, the element is turned off before it is moved to the second position.

In another embodiment is also an apparatus for applying energy to a hollow anatomical structure comprises a catheter sized for at least partial insertion into the hollow anatomical structure. The catheter has a heat-emission region, which in turn has a length and a width measured orthogonal to the length. The length of the heat emission region is preferably greater than its width. The heat-emission region emits heat at a substantially uniform temperature along substantially all of its length.

In some embodiments, methods of adjusting an operating temperature of the system are provided. In one embodiment, the operating temperature can be adjusted by adjusting a relief valve. In another embodiment, the operating temperature of the system can be adjusted by choosing or adjusting the fluid used in the system. In another embodiment, the operating temperature of the system can be varied by adjusting both a relief valve and varying the properties or amount of a fluid.

One embodiment is an apparatus for applying energy to a hollow anatomical structure having an inner wall. In one such embodiment, the apparatus comprises a heating element configured to create an electric field that extends at least partially into a tissue of a surrounding HAS in which the device is positioned. The heating element generates heat in the surrounding fluid and/or tissue by causing movement of dipolar molecules in the surrounding fluid/tissue.

In one embodiment, a capacitive heating element comprises a pair of elongate parallel electrodes separated by a non-conductive element. The non-conductive element can comprise an air gap, a solid non-conductive material, or a combination thereof. In another embodiment, a capacitive heating element comprises two pairs of elongate parallel electrodes separated by non-conductive elements. In further embodiments, a capacitive heating element can include three or more pairs of elongate parallel electrodes separated from one another by electrically non-conductive elements. In further embodiments, a capacitive heating element can include a plurality of electrodes wrapped in a helical pattern around a solid or hollow central core. In another embodiment, a capacitive heating element comprises a plurality of ring-shaped electrodes. In each of the above embodiments, the electrodes can be configured to be joined to a power source in order to apply electric fields across adjacent electrodes such that the electric fields extend outwards from the radial extent of the device.

In one embodiment, a catheter comprises an elongate shaft and an electrode element located distal of the elongate shaft. A sheath is slidably disposed on the shaft. The sheath and catheter are relatively moveable between a first configuration in which the sheath covers substantially all of the electrode element, and a second configuration in which the sheath covers less than substantially all of the electrode element. The electrode element may be energized by an energy source using alternating current in the RF range.

In another embodiment, a catheter system comprises an elongate shaft and an energy-emission element located distal of the elongate shaft. The energy-emission element includes a plurality of emission segments, a plurality of the segments are independently operable to emit energy into the surroundings of the energy-emission element. Optionally, the catheter system further comprises a power source drivingly connected to the emission segments. The power source is operable pursuant to a multiplexing algorithm to deliver power to, and operate, the emission segments in a multiplexed fashion. In one embodiment, the energy-emission element comprises an electrode element. The electrode element may be energized by an energy source using alternating current in the RF range. In one embodiment, the electrode comprises an RF emitter.

In another embodiment, a catheter system comprises an elongate shaft and an energy-emission element located distal of the elongate shaft. The energy-emission element has an effective axial length along which the energy-emission element emits energy. The effective axial length is adjustable.

In another embodiment, a catheter comprises an elongate shaft and one or more expandable members located on the elongate shaft. One or more electrode elements are positioned on the one or more expandable members. The one or more electrode elements may be energized by an energy source using alternating current in the RF range.

In another embodiment, a device for treating a hollow anatomical structure comprises an elongate structure with an energy-delivering distal portion. The distal portion is movable between a first position with a minimal transverse dimension and a second position with a maximum transverse dimension, wherein the maximum transverse dimension of the planar shape is selected to engage an internal wall of the hollow anatomical structure sufficiently to cause the hollow anatomical structure to conform to the shape of the distal portion.

Certain disclosed embodiments comprise a device and/or a method capable of providing heat energy along a circumferential band to a vein wall over a specific length without localized boiling, the likelihood of recurrence due to neovascularization, excessive pain levels & recovery times, coagulum build-up causing incomplete treatments, long treatment times from having to pull back the catheter, and the issue of variable pullback rates causing incomplete treatments and the subsequent need for re-treatment.

In one embodiment, a catheter includes a plurality of primary leads to deliver energy for ligating a hollow anatomical structure. Each of the primary leads includes electrodes located at the working end of the catheter. The primary leads are constructed to expand outwardly within a single plane for the purpose of conforming the hollow anatomical structure it is placed within to the expanded profile of the catheter. In doing so, the hollow anatomical structure is placed into apposition with the electrodes. Energy can then be applied from the leads to create a heating effect in the surrounding tissue of the anatomical structure. The diameter of the hollow anatomical structure is reduced by the heating effect, and the electrodes of the primary leads are moved closer to one another as the diameter reduces. Where the hollow anatomical structure is a vein, energy is applied until the diameter of the vein is reduced to the point where the vein is occluded. The catheter can include a lumen to accommodate a guide wire or to allow fluid delivery.

Certain devices and methods disclosed herein are capable of more evenly distributing energy along the target hollow anatomical structure utilizing lower temperatures and the ability to regulate power via a temperature feedback loop in a continuous simultaneous length.

Devices and methods disclosed herein are preferably suitable for ligation of hollow anatomical structures in the body, including but not limited to varicose veins generally, perforator and superficial veins, as well as hemorrhoids, esophageal varices, and also fallopian tubes.

Certain objects and advantages of the invention are described herein. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of the embodiments summarized above are intended to be within the scope of the invention herein disclosed. However, despite the foregoing discussion of certain embodiments, only the appended claims (and not the present summary) are intended to define the invention. The summarized embodiments, and other embodiments of the present invention, will become readily apparent to those skilled in the art from the following detailed description of the preferred embodiments having reference to the attached figures, the invention not being limited to any particular embodiment(s) disclosed.

BRIEF DESCRIPTION OF THE DRAWINGS

FIG. 14 is a partial cut-away view of the working end of the device of FIG. 13 in a short length;

FIG. 15 is a partial cut-away view of the working end of the device of in FIG. 13 in a long length.

FIG. 16 is a cut-away view of the working end of another embodiment of a HAS ligating device.

FIG. 17 is a cross-sectional end view of the ligating device of FIG. 16.

FIG. 21 is a cross-sectional view taken through the diameter of the working end of another embodiment of a HAS treatment device.

FIG. 22 is a cross-sectional view taken through the diameter of the working end of another embodiment of a HAS treatment device.

FIG. 23 illustrates another embodiment of an energy element for use in a HAS ligating device.

FIG. 49 illustrates another embodiment of a working portion of the catheter body with individually expandable loops;

FIG. 50 illustrates the embodiment of FIG. 49 with the individually expandable loops retracted;

FIG. 59 illustrates another embodiment of an expandable device having expandable ribbons along a working portion of the catheter;

FIG. 60 illustrates the expandable device of FIG. 59 in an expanded configuration;

FIG. 61 illustrates an embodiment of an expandable device having a sheath and an expandable ribbon along a working portion of the catheter in a non-expanded configuration;

FIG. 62 illustrates the embodiment of FIG. 61 in an expanded configuration;

FIG. 63 illustrates another embodiment similar to the embodiment shown in FIGS. 61 and 62 having another expanded configuration;

FIG. 64 illustrates another embodiment similar to the embodiment of FIGS. 61-63 having another expanded configuration.

FIG. 74 is a schematic view of another embodiment of an HAS conforming device in which the working end of the catheter is expanded outside the sheath.

FIG. 75 is a cross-sectional view of the device of FIG. 74 in which the pull wire and catheter shaft is shown within the sheath.

FIG. 76 is a schematic view of some additional embodiments of a HAS conforming catheter.

FIGS. 77A-F illustrates embodiments of distal flexible components for use in an HAS conforming device.

FIG. 81 is a view of an alternate embodiment of the device in FIG. 79.

FIG. 82 is a view of an alternate embodiment of the device in FIG. 79.

FIGS. 83-86 show schematic views of another embodiment in the collapsed and expanded states of the device and respective cross-sectional views of the same.

DETAILED DESCRIPTION OF THE PREFERRED EMBODIMENTS

Figure 1:
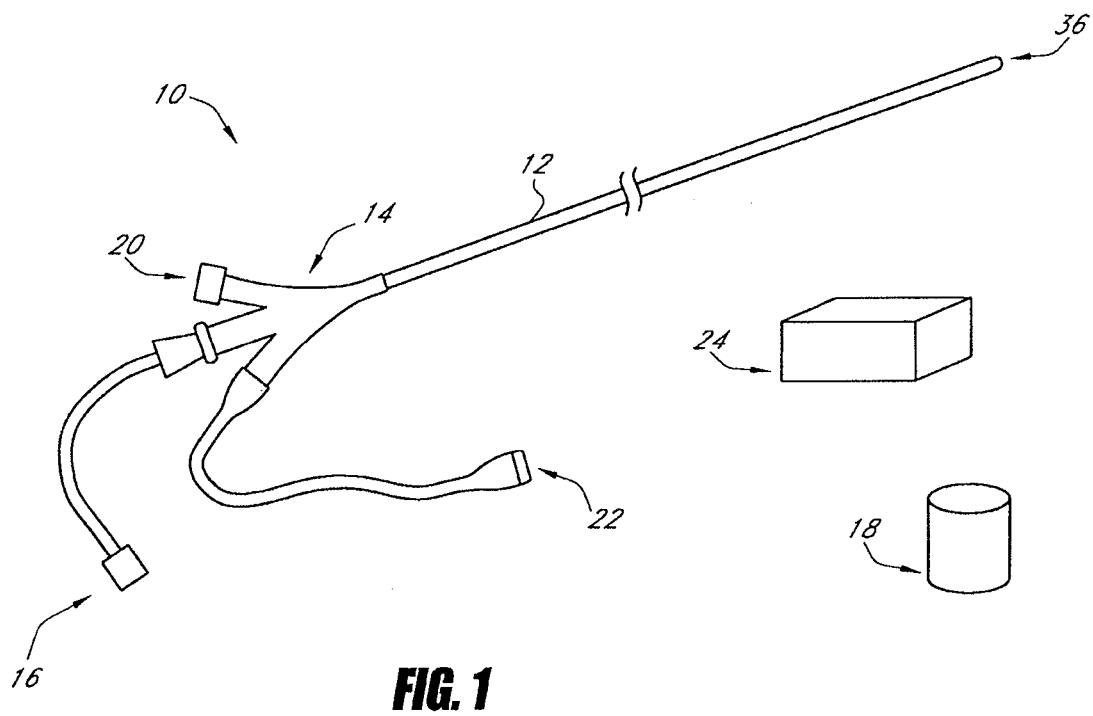
FIG. 1 is a schematic view of one embodiment of a device for ligating a hollow anatomical structure (HAS), including a handle and connections.

FIG. 1 shows an embodiment of a device or catheter 10 for applying energy to a hollow anatomical structure (HAS), such as a vein. The catheter 10 includes a catheter shaft 12 having a handle 14. The catheter shaft 12 can comprise a biocompatible material having a low coefficient of friction. In one configuration, the catheter shaft 12 is sized to fit within a vascular structure that may be between 5 and 9 French, which corresponds to a diameter of between about 1.7 mm (0.07 in) and about 3.0 mm (1.2 in), or other sizes as appropriate to correlate to the HAS. Thus, in some embodiments the catheter shaft 12 may have a diameter of about 1-2 mm. The handle 14 includes a fluid port 16 for infusion of an electrically conductive fluid or liquid drawn from a reservoir 18, a pressure relief valve 20 for venting the shaft 12 to ambient air, and a connection 22 for interfacing with an energy source 24. In the present embodiment, the energy source 24 can be either alternating current (AC) or direct current (DC) like an RF generator or other type of power supply. The fluid reservoir 18 provides a flow of electrically conductive fluid or liquid into the catheter shaft 12, and the energy source 24 provides a power output that the user can manually adjust. The system can also include a temperature sensor (not shown) such as a thermocouple or thermistor to provide feedback to the user regarding system operation and temperature. For example, a thermocouple can be placed on the surface of the shaft 12.

Figure 2:
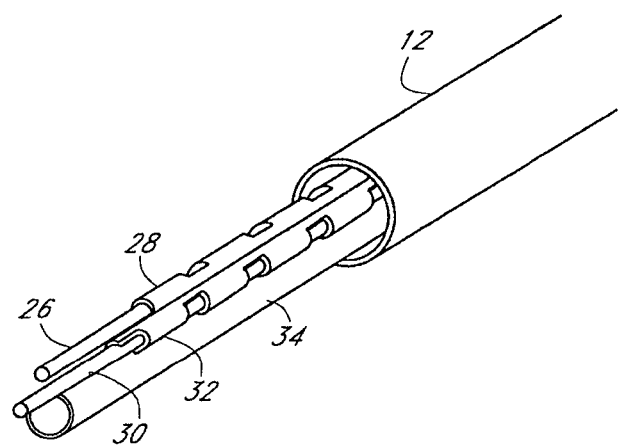
FIG. 2 is a cut-away perspective view of a working (distal) end of the device of FIG. 1.
Figure 3:
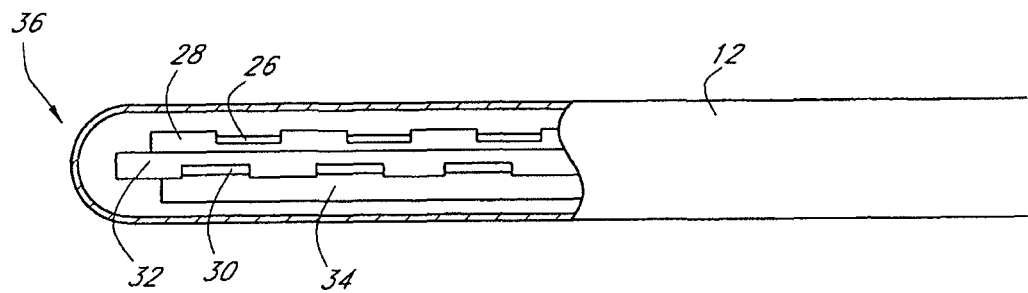
FIG. 3 is a partial cross-sectional view of the working end of the device of FIG. 1.

Referring now to FIGS. 2 and 3, a positive RF wire 26 encased in an insulation material 28, and a negative RF wire 30 encased in an insulation material 32, are located within a catheter shaft 12. The insulation material 28, 32 is stripped or skived away from a portion of the respective wires 26, 30 at specific intervals along the lengths of the wires 26, 30 to expose the wires 26, 30 to the interior of catheter shaft 12. The RF wires 26 and 30 are skived along a length that corresponds to the desired vein-treatment length. In the depicted embodiment, the skived areas or electrodes are situated in a longitudinally-alternating configuration along the lengths of the respective wires 26, 30. However, in other embodiments a symmetric or mirrored configuration may be employed, with the skived portions on the wires 26, 30 adjacent one another.

Contained within the catheter shaft 12 is a fluid lumen 34. The fluid port 16 communicates with the interior of fluid lumen 34, with the interior of catheter shaft 12 and with a manually adjustable pressure relief valve 20. The fluid lumen 34 terminates just proximal to the tip 36 and allows fluid to flow into the interior of catheter shaft 12. The electrically conductive fluid or liquid can flow from the reservoir 18, through the fluid port 16, through the fluid lumen 34, into the catheter shaft 12, thus surrounding the positive RF wire 26 and the negative RF wire 30. The fluid lumen 34 can be used to infuse additional fluid into the catheter shaft 12. This additional fluid may become necessary as a replacement for fluid that has changed phase, formed vapor bubbles and moved up the catheter shaft 12 toward the pressure relief valve 20. Replacement fluid can be slowly dripped into the catheter shaft 12 at a rate sufficient to keep the system functioning, but not so much that the added fluid would cool the catheter shaft 12 too much. In one embodiment, the fluid lumen 34 can have an outside diameter of about 0.5 mm to 1 mm.

The catheter shaft 12 can be vented to ambient air via the pressure relief valve 20. This valve can be used to build, maintain and/or relieve pressure in the system and tune the boiling point as desired. As the fluid is heated to its boiling point, the gaseous bubbles that form within the shaft 12 interrupt the path of the electrical energy as it flows through and heats the fluid. As the fluid temperature increases, the presence of more and more bubbles increases this inhibiting effect. Accordingly, the creation of bubbles (and/or the retention of bubbles in the conduction path(s) between the exposed portions of the wires 26, 30) is one mechanism that can be used to control the temperature of the system. Bubbles created through boiling can be controllably released through the pressure relief valve 20, discussed above.

In addition, at a given pressure (which can be set via the pressure relief valve 20) the conductive fluid has an inherent or "self-regulating" maximum temperature or boiling point which in turn sets an inherent or "self-regulating" maximum temperature of the working end of the catheter. This advantageously provides an effective safety feature for the catheter, which can be set to prevent overheating of the treated tissue and/or to preclude the need for a temperature feedback loop that actively governs power delivery to achieve a desired set-point temperature.

In some embodiments, electrically conductive fluids of varying degrees of viscosity, and conductivity might be employed. Such fluids might include saline, water, biocompatible oils, dextrose solution, and the like. The fluid is chosen to get a desired boiling point. The boiling point can be derived from a desired treatment temperature (for example, a treatment temperature of 100° might require a conductive-fluid boiling point of 113, given potential losses in the catheter system, and potential losses in the thermal coupling of the catheter to the wall of the HAS in which the catheter is employed). Thus, a temperature of the working end can be controlled by controlling the boiling point of the fluid (for example, by choosing a fluid with a particular boiling point), by controlling a flow rate of the fluid through the system, or by controlling the pressure at which the pressure valve vents.

The following table shows examples of liquids that can be used alone or mixed in such a system, including the boiling points of the liquids at one atmosphere (1 atm), or seven hundred and sixty torr (760 mm Hg).

| Liquid | Boiling Point (° C.) |
| --- | --- |
| 0.9% Saline | 100 |
| Acetone | 56.48 |
| Benzene | 80.1 |
| Chloroform | 62.26 |
| Ethyl Acetate | 77 |
| Ethyl Alcohol | 78.3 |
| Heptane | 98 |
| Hexane | 69 |
| Hydrogen Peroxide 6% | 106 |
| Iron (III) Nitrate Xonahydrate | 125 |
| Isopropyl Alcohol | 80.3 |
| Liqui-Nox | 101.1 |
| Methanol | 64.5 |
| Naptha (Benzine, 76C Naptha) | 100-140 |
| Octane | 126 |
| Petroleum Spirits | 35-180 |
| Sucrose Solutions (dextrose, fructose) | 100-150 |
| α-Trichloroethane | 74.1 |
| Trichloroethylene | 86.7 |
| Toluene | 110.4 |
| Water | 100 |
| Xylene (m, o, p) | 139, 144.4, 138.3 |

The catheter shaft 12 can include an atraumatic tip 36 for facilitating manipulation of the catheter into the HAS of the patient. The tip 36 is preferably tapered inward or rounded at its distal end, or the tip 36 can have other shapes that facilitate threading or tracking of the catheter through the bends in the vascular system.

In one embodiment, the tip 36 can, for example, be fabricated from a polymer having a soft durometer, such as 70 Shore A. Further, the tip can be fabricated from any number of materials with varying durometer such as pebax, polyimide, polyethylene, silicone (softer more atraumatic materials) or stainless-steel or ceramic as a blunt tip. Additionally, the tip might employ an endostructure or exostructure to define its flexibility characteristics.

Figure 4:
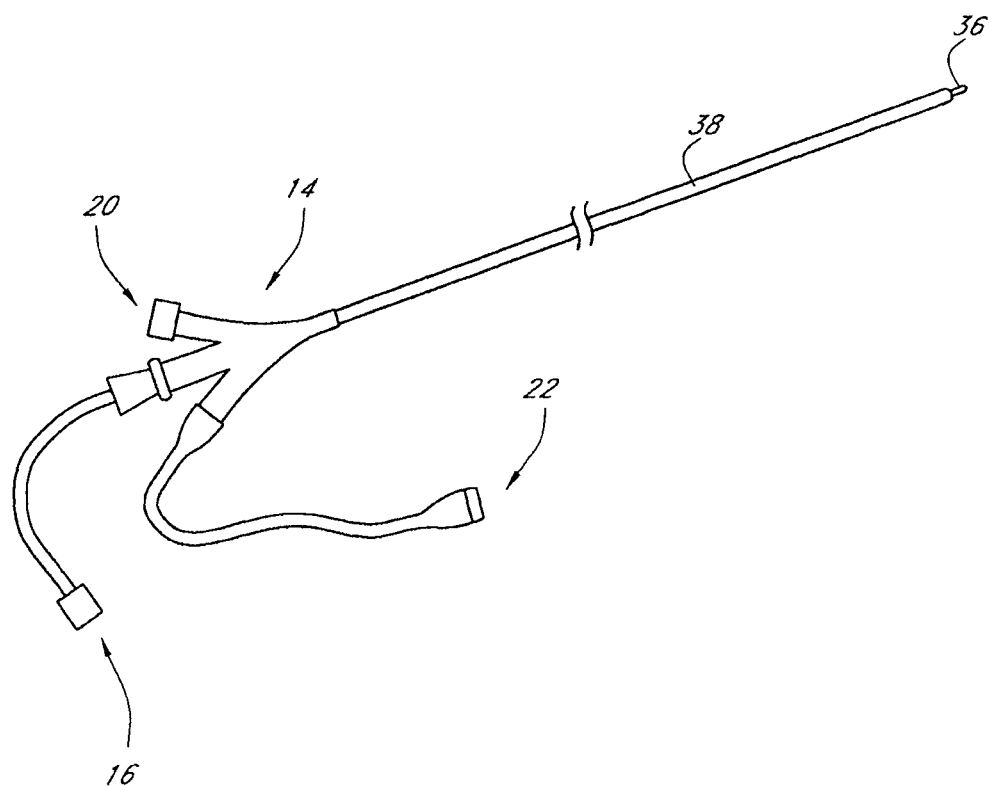
FIG. 4 is a schematic view of another embodiment of a HAS ligating device, in which the working end is retracted within a sheath.
Figure 5:
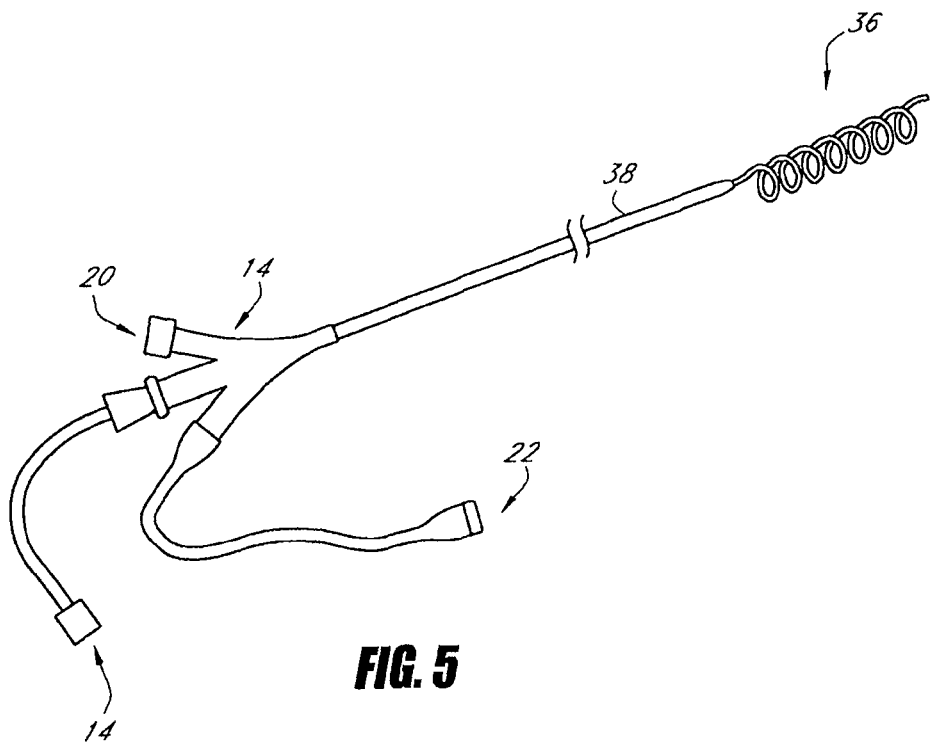
FIG. 5 is a schematic view of the catheter of FIG. 4 in which the working end of the catheter is expanded outside the sheath.

A second embodiment of the catheter, depicted in FIGS. 4 and 5, may be generally similar to the embodiment depicted in FIGS. 1-3, except as further described herein. The embodiment of FIGS. 4-5 employs a coiled catheter shaft 36 to facilitate apposition with the HAS wall. The embodiment of FIGS. 4 and 5 may be particularly useful in situations where external compression (such as manual, Esmark, or Tumescent Anesthesia) of the HAS or other methods are insufficient to cause the HAS diameter to reduce sufficiently to appose a fixed-diameter catheter. The coiled configuration may comprise an open helix or corkscrew, and can be made from a deformable material like pebax, polyimide, polyethylene or silicone. The helical shape can also be obtained by using a shaped spine or wire made from nickel-titanium, stainless-steel or other materials with similar characteristics.

An outer sheath 38 can be used to enclose and straighten the coiled catheter shaft 36 for introduction into and advancement through the HAS to be treated. In certain embodiments, the outer sheath 38 can be retractable, and the treatment length can be adjusted by actuating the retractable outer sheath 38 from outside of the body. This can be done by introducing the catheter into the body with the sheath 38 covering an active portion of the catheter and advancing the tip to the treatment site. The sheath 38 can then be withdrawn until the length of the active portion matches the length of the desired treatment area. The retractable sheath 38 can accordingly insulate adjacent tissue from thermal damage.

One embodiment of the inventions comprises a method of treating a HAS by gaining HAS access; inserting a catheter with an outer access sheath into the HAS; positioning the tip of the catheter near the saphenofemoral junction or other desired treatment starting point in the HAS; withdrawing the protective outer sheath to allow the catheter to assume a deployed (e.g. helical) shape (see the coiled catheter shaft 36 of FIG. 5); supplying electrical energy to the device; maintaining the device in position for a clinically effective time period (for example, 15, 30 or 60 seconds); retracting the catheter back into the outer sheath; withdrawing the catheter from the HAS; and confirming that the HAS has been occluded (using ultrasound, for example).

Figure 6:
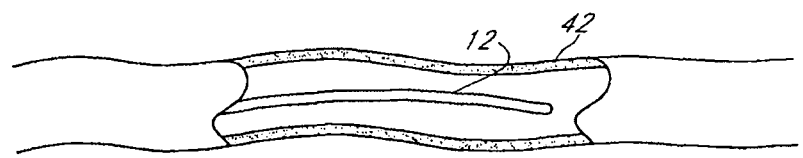
FIG. 6 is a partial cut-away view depicting the working end of the device of FIG. 1, within a HAS to be treated.
Figure 8:
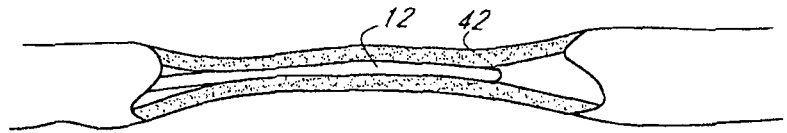
FIG. 8 is a partial cut-away view depicting the working end of the device of FIG. 1 within the treated HAS.

Referring now to FIGS. 6 and 8, the catheter shaft 12 of the embodiment of FIGS. 1-3 is shown in the vessel segment to be treated just prior to treatment and just after treatment, respectively. Thus, in FIG. 6, the catheter shaft 12 extends inside a HAS without touching the side walls of the HAS 42, but in FIG. 8, the side walls 42 of the HAS are in apposition with the catheter shaft 12.

Figure 7:
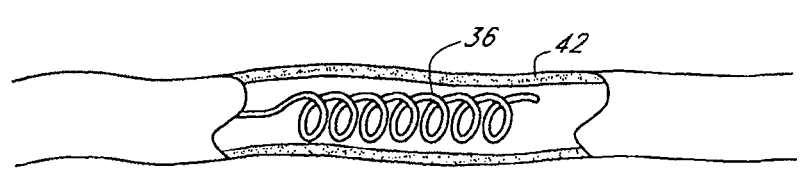
FIG. 7 is a partial cut-away view depicting the working end of the device of FIGS. 4-5, expanded outside the sheath and within a HAS to be treated.
Figure 9:
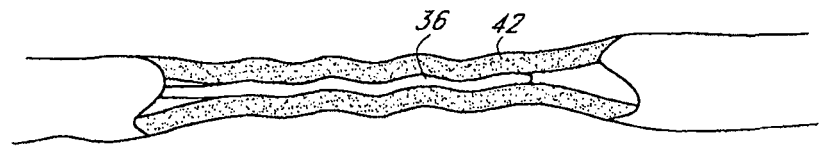
FIG. 9 is a cut-away view depicting the working end of the device of FIGS. 4-5, expanded outside the sheath and within the treated hollow anatomical structure.

Referring now to FIGS. 7 and 9, the catheter shaft 36 of the embodiment of FIGS. 4-5 is shown in the vessel segment to be treated just prior to treatment and just after treatment, respectively. Thus, in FIG. 7, the catheter shaft 36 extends inside a HAS without touching the side walls of the HAS 42, but in FIG. 9, the side walls 42 of the HAS are in apposition with the catheter shaft 36.

In some embodiments, a catheter can include holes positioned along the length of the catheter tube to allow fluid to escape and heat the surrounding tissue. Furthermore, in an embodiment where such holes are present, higher fluid flow rates and pressure can be maintained to force small jets of liquid against and/or into the wall of the target anatomical structure.

Figure 10:
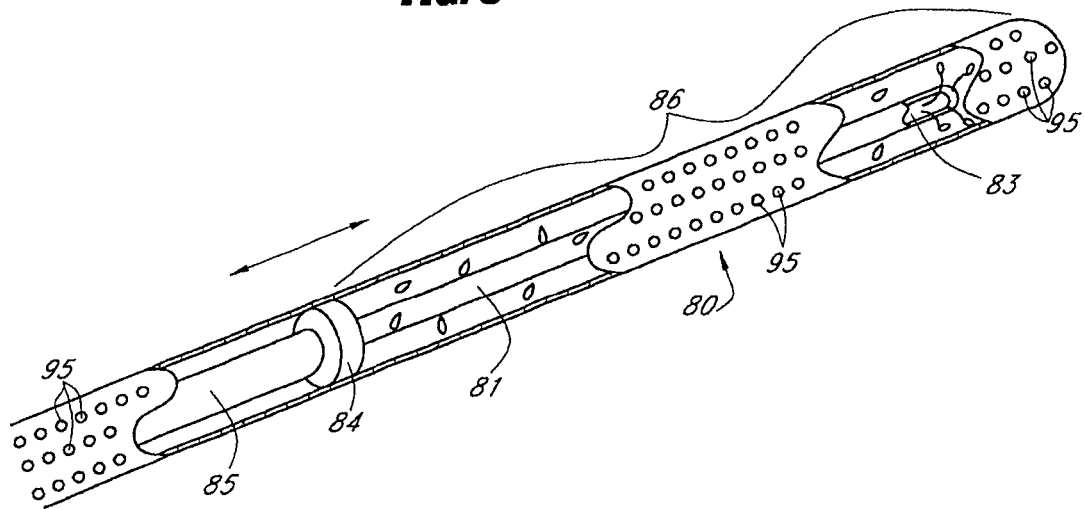
FIG. 10 is a partial cut-away view of the working end of an alternative embodiment of the device of FIG. 1.

FIG. 10 shows another embodiment of a HAS treatment device configured to emit steam through a plurality of openings along a portion of its length. Except as further described below, the device of FIG. 10 can be generally similar to either of the embodiments of FIGS. 1-3 or 4-5. The device may be constructed of a catheter shaft 12 comprising a perforated outer sheath 80 at the working end. The sheath 80 generally surrounds a fluid cavity 86 which can have an energy element 81 extending therethrough. In some embodiments, the energy element 81 is configured to heat a liquid contained within the fluid cavity 86.

In some embodiments, the sheath 80 is made of a material that can withstand high temperatures, such as Polyamide, Teflon or Ultem. This sheath 80 is preferably sufficiently lubricious to allow introduction into the HAS, to facilitate navigation through the HAS to the desired treatment site, and to prevent blood coagulum build-up on its exterior. The sheath 80 can therefore be coated with a lubricious and/or non-stick coating, comprising Teflon or Paralyene, for example. The outer sheath 80 may also be made from a suitable kink-resistant material, such as braided Polyimide, for example.

As shown in FIG. 10, the sheath 80 can include a plurality of micro-perforations 95. The micro-perforations 95 can be formed by puncturing the sheath 80 substantially without removing material. Thus, each micro-perforation provides a fluid pathway between an interior and an exterior of the sheath 80 which is substantially closed under normal conditions. However, when a fluid pressure within the sheath exceeds a fluid pressure outside of the sheath, the fluid will pass through the micro-perforations. The internal/external pressure differential required to cause such a fluid flow can generally be varied by varying properties of the sheath, such as a durometer of the material, by varying the amount of micro-perforations present on the sheath or by varying the diameter of the micro-perforations themselves.

FIG. 10 also illustrates an energy element 81 located within the sheath. The energy element 81 can comprise one or more RF electrodes, thermal resistance heaters, laser, or other device capable of delivering energy to a load. The energy element 81 may comprise a resistive wire coiled around an inner member and connected to the energy supply 24 via the connector 22 located at the catheter handle 14. The resistive wire can be made of metal capable of transferring electrical energy. For example, the wire can be a material such as copper or nichrome. The energy element can be powered by an AC or DC power supply. The energy element 81 may also comprise coaxially-placed electrodes as discussed above. The energy element 81 is preferably configured to deliver a controlled quantity of energy to a load surrounding or adjacent to the element 81 at a controlled rate and/or for a controlled length of time.

In some embodiments, the energy element 81 extends along substantially the entire length of the outer sheath 80 so that the inner member tip is adjacent the tip of the outer sheath 80. In some embodiments, the energy element 81 may extend a finite length, for example 45 cm, measured from the distal tip of the outer sheath 80 towards the proximal handle 14. Preferably, the length of the energy element 81 generally corresponds to the desired length of the HAS to be treated.

In some embodiments, energy is transferred from the energy element 81 to a HAS via a fluid located within the outer sheath 80 and surrounding the energy element 81 within a fluid chamber 86. In some embodiments, the fluid is introduced into the fluid chamber 86 as a liquid which is then heated above its boiling temperature, thereby causing a phase change that initiates production of gas (such as steam when the liquid is water). Once the fluid pressure of the gas exceeds a threshold pressure, the gas is forced through the micro-perforations in the outer sheath 80 towards the HAS. Before the fluid pressure within the fluid chamber 86 exceeds the threshold pressure, the micro-perforations remain closed, thereby retaining the heated fluid within the fluid chamber 86.

The liquid may be delivered into the fluid chamber 86 via an internal lumen 83 extending longitudinally through the energy element 81. In some embodiments, the energy element 81 comprises only a single distal opening such that fluid may exit through only the very distal tip of the energy element 81. The energy element 81 further comprises a proximal opening (not shown) configured to allow a fluid to enter the lumen in the handle 14 via a connector 20 from an auxiliary fluid source 18 (see FIG. 1). In some embodiments, a fluid pressure applied by the fluid source 18 is sufficient to ensure that the fluid chamber 86 remains filled, but is not so high as to cause release of the liquid through the micro-perforations 95.

In some embodiments, the fluid is heated through direct contact with the energy element 81. The energy element 81 heats the liquid via regulated power delivery from the energy source 24 (see FIG. 1) until the liquid reaches its boiling point. The regulation of delivered power can be accomplished with an electrical power source via an optimized power curve created expressly for the energy element 81.

The boundaries of the fluid chamber 86 are defined by the outer sheath 80, the distal tip, and a proximally-placed seal component 84 that seals around the energy element 81 and abuts the inner walls of the outer shaft 80. The seal is preferably substantial enough to prevent undesired leakage at the expected operating fluid pressures. Thus, in some embodiments, the fit between the seal component 84 and the energy element 81 is an interference fit. Additionally, a material from which the seal component 84 is made will preferably be substantially resistant to high temperatures and will provide a good sealing force. In some embodiments, the sealing component comprises a Silicone material. Alternatively, the sealing component can be made of Pebax, Santoprene, PET, or other suitable material. A seal component can be formed by molding, casting, machining or otherwise shaping from a suitable material.

In some embodiments, the length of the fluid chamber 86 can be adjusted by varying an axial placement of the seal 84. For example, in some embodiments this adjustment is performed by actuating an attached seal actuation member 85. This actuation member 85 is preferably strong enough and attached to the seal 84 with enough strength to allow for significant 'pushability' as well as 'pullability' since it has to overcome a relatively large frictional force created by the internal seal. Therefore, in some embodiments, the actuation member 85 can be a tube made of a material capable of providing significant column strength while still bonding well to the seal, such as stainless-steel or Hytrel. Actuation of the member 85 may be facilitated by any suitable mechanism located at the proximal catheter handle 14.

Figure 11:
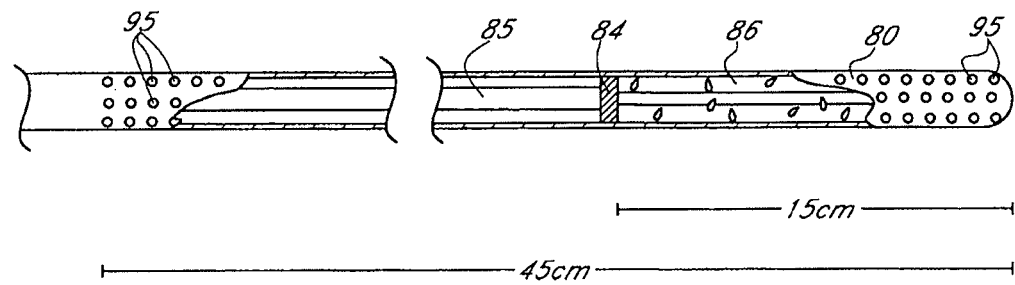
FIG. 11 is a partial cutaway view of the working end of the device of FIG. 10 in a short length.
Figure 12:
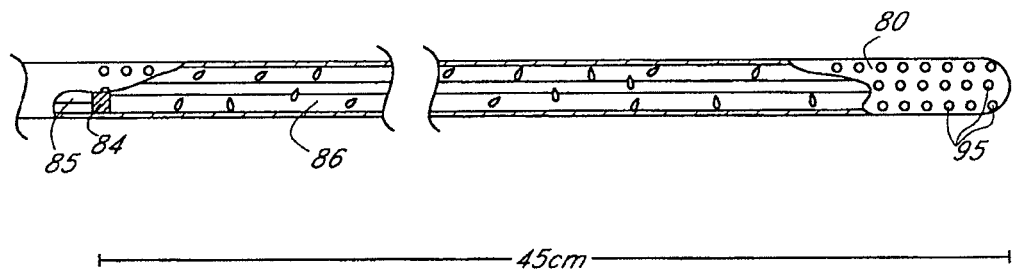
FIG. 12 is a partial cutaway view of the working end of the device of FIG. 10 in a long length.

With reference now to FIG. 11 and FIG. 12, in some embodiments the entire length of the outer sheath 80 can include micro-perforations 95. However, in the illustrated embodiment, the seal position defines the proximal extent of the fluid chamber 86, and hence the portion of the catheter configured to emit high temperature gas is substantially limited to the section immediately surrounding the fluid cavity 86. Thus, in the illustrated embodiment, the length between the seal component 84 and the distal tip of the sheath 80 corresponds to the treated length of the HAS. In embodiments where the seal 84 is slidable relative to the outer sheath 80, the treatment length can be adjusted from a minimum length (for example: 15 cm) to a maximum length (for example: 45 cm) and any length in between. In some embodiments, the treatment length can be adjustable between about 1 cm and about 60 cm. In other embodiments, the treatment length can be adjustable between about 5 cm and about 45 cm, and in one preferred embodiment, the treatment length can be adjustable between about 15 cm and about 45 cm.

Figure 13:
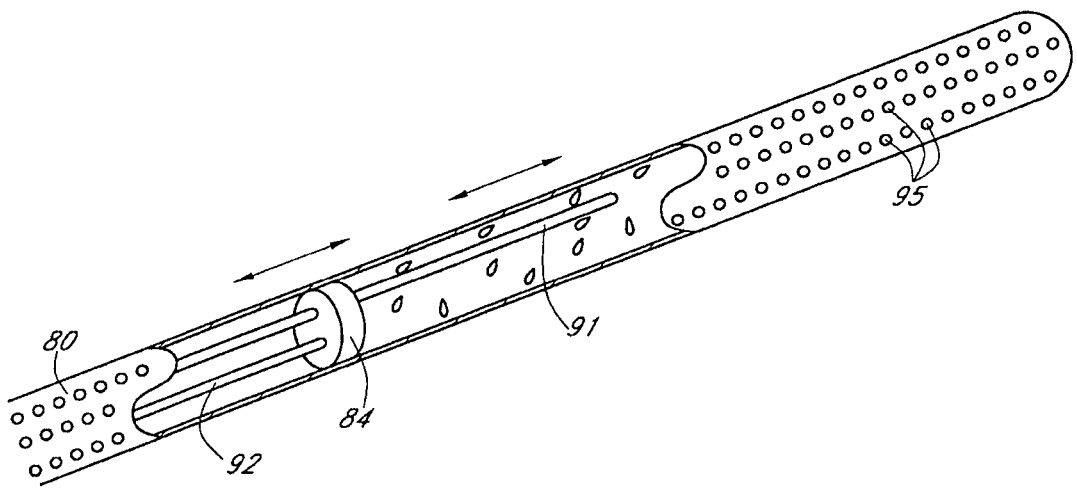
FIG. 13 is a cut-away view of the working end of an alternative embodiment of the device of FIG. 1.

In the embodiment illustrated in FIG. 13, an energy element 91 may be substantially solid, such as a laser fiber, so that fluid may not be delivered through it. In this embodiment, the seal 84 may still be statically or adjustably positioned so as to provide a desired treatment length. The tip of the energy element 91 can be axially positioned relative to the distal tip of the catheter and seal 84 to provide optimized energy delivery. For example, in some embodiments the distal tip of the energy element 91 is positioned about half way between the seal 84 and the distal tip of the catheter. Fluid may then be delivered through a separate fluid lumen 92 that is placed within the outer sheath 80 and ends adjacent a distal side of the seal 84. In some embodiments, a structure forming the fluid lumen 92 may also act as a seal actuation member (performing the function described above with respect to the actuation member 85).

FIGS. 14 and 15 illustrate embodiments of a device with a variable fluid chamber length and a solid energy element 91, such as a laser fiber. In the embodiments of FIGS. 14 and 15, the seal position defines the proximal extent of the fluid chamber 86, and hence the portion of the catheter configured to emit high temperature gas can be substantially limited to the section immediately surrounding the fluid cavity 86. Thus, in the illustrated embodiment, the length between the seal component 84 and the distal tip of the sheath 80 defines the treated length of the HAS. In embodiments where the seal 84 slides relative to the outer sheath 80, the treatment length can be adjusted from a minimum length (for example: 15 cm) to a maximum length (for example: 45 cm) and any length in between. In some embodiments, the treatment length can be adjustable between about 1 cm and about 60 cm. In other embodiments, the treatment length can be adjustable between about 5 cm and about 45 cm, and in one preferred embodiment, the treatment length can be adjustable between about 15 cm and about 45 cm.

FIG. 16 shows the working end of another embodiment of a device for ligating a HAS. In this embodiment, RF electrodes 101 are shown as a pair of linear, flat metal strips attached to an outer surface and along the length (the length parallel to the axis of cylindrical symmetry) of an inner catheter lumen 102. FIG. 16 shows only one of the two electrodes, as the second electrode is located on the opposite side of the catheter lumen 102. FIG. 17 shows an end-on view of the structure of FIG. 16, showing the electrodes 101 on either side of the catheter lumen 102. These electrodes 101 can be flat wire, round wire or metal tape such as copper tape or stainless-steel tape. Signal wires 103 may be attached to one end of the electrodes 101 by soldering, spot welding, bonding with a conductive adhesive, such as silver epoxy, or by using other suitable methods.

In some embodiments, a thin electrically insulative material 104 such as polyimide, Teflon or silicone tape may be helically wound around the inner lumen assembly (e.g., the inner lumen 102 and the electrodes 101). The insulative material 104 can be about 0.003 inches to about 0.020 inches thick. However, material thicknesses outside of this range can also be used.

Figure 18:
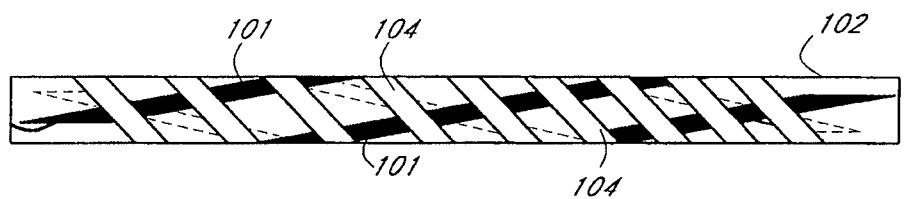
FIG. 18 is a cut-away view of the working end of another embodiment of a HAS ligating device.

Helically winding an electrically insulative material 104 around the electrodes 101 can effectively form multiple discrete shorter electrodes from each longer electrode 101. When the sections of exposed electrodes are equal in surface area along each strip (each exposed section having a corresponding exposed section of approximately similar dimensions on the other electrode 101), the heat produced starts near the signal wire attachment section and eventually propagates along the electrodes 101 to the distal end. For example, the portions of the electrodes 101 nearest the attachment point of the signal wire 103 can be hotter than those portions of the electrodes 101 farther away from that attachment point. The pitch of the helical tape windings of the insulative material 104 can be varied as shown in FIGS. 16 and 18, such that the exposed electrode surface area decreases as the windings move distally from the signal wire attachment point. Thus, in such an embodiment, the heating is advantageously more uniform over the length of the entire electrode strip pair. For instance, the pitch of the wound insulative material 104 may vary so as to allow an open gap width substantially less than the width of the material itself at the distal end of the catheter, and substantially more than the insulative material width towards the proximal end.

FIG. 18 shows an alternative embodiment of an energy element. In the embodiment of FIG. 18, the electrode strips 101 are helically wound around an inner catheter lumen 102 in a direction counter to a helical winding direction of the insulative material 104. This counter winding of the electrodes 101 can prevent a circumferential bias of the heat that can otherwise be generated by the configuration of FIGS. 16 and 17, where the electrodes 101 are not wound. Heat generated by purely longitudinal (non-wound) electrodes 101 may have some zones of greater heat generation nearer the portions of the catheter lumen 102 contacted by the electrodes 101, thus creating a temperature gradient with a bias between hotter and cooler zones. By winding the electrodes 101, the temperature gradients can be changed and temperature bias can be reduced.

Figure 19:
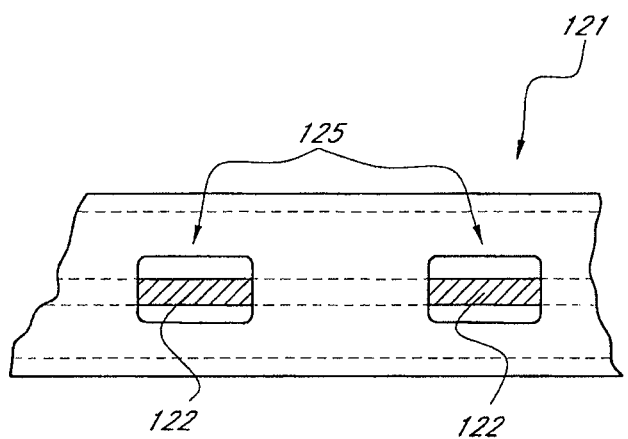
FIG. 19 is a partial cut-away view of the working end of another embodiment of a HAS ligating device.
Figure 20:
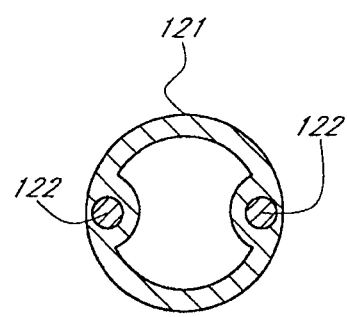
FIG. 20 is a cross-sectional view taken through the diameter of the working end of the embodiment of FIG. 19.

FIGS. 19 and 20 illustrate another embodiment of an energy element. In this embodiment, a catheter lumen comprises an extrusion tube 121 that contains electrode wires 122 within the wall of the extrusion tube 121. A plurality of windows 125 can be provided at various positions along the extrusion tube 121 in order to expose portions of the electrode wires 122. For example, such a structure can be formed by extruding a tube around a pair of electrode wires 122. The skived windows 125 can be formed during the tubing molding process itself, by mechanical cutting or by a secondary etching process. Mechanical cutting can include skiving performed by selective cutting using a laser or water jet, for example. FIG. 20 shows a cross section through the diameter of the embodiment of FIG. 19.

FIGS. 21-22 show cross sections through the diameters of two alternative embodiments of extrusions. As shown, the wires 122 can extend longitudinally and substantially parallel to the extrusion axis. These wires may be generally round (FIGS. 20 and 22) or generally rectangular (FIG. 21) in cross section. Many other wire cross-sectional shapes are possible which may be beneficial to the design for flexibility and electrode configuration. The internal lumen 186 is useful as the fluid cavity (see the fluid cavity 86 of FIG. 10, for example). This lumen 186 can be used for temperature sensors and other signal wires which can run internally to the lumen but are not shown. These wires can run from the distal working portion of the catheter to the proximal handle 14 and connector 20 (see FIG. 1).

Alternatively, the wires 122 can wind helically through the tube wall to promote overall device flexibility. FIG. 23 shows schematically an example of a pair of helically wound wires embedded within the tube extrusion wall. Two wires are used in this example for clarity, but as in FIG. 22, multiple pairs could be used. As discussed earlier, skived windows can be incorporated in this extrusion to expose sections of the wire pairs in order to create working electrodes.

Figure 24:
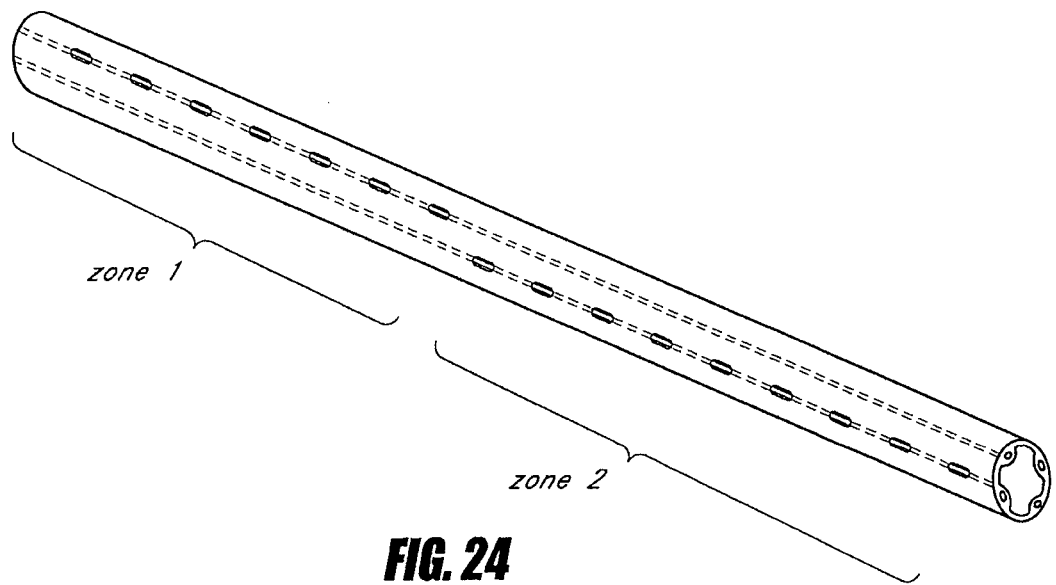
FIG. 24 illustrate another embodiment of an energy element for use in a HAS ligating device.
Figure 25:
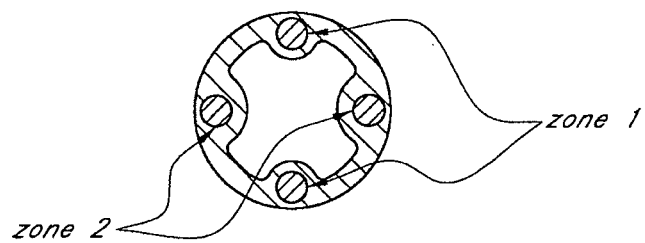
FIG. 25 illustrates a cross-sectional view taken through the diameter of the working end of the embodiment of FIG. 24.

The isometric view of FIG. 24 (an end view of which is shown in FIG. 25) shows an example of multiple pairs of RF electrodes. In this version, the pairs of electrodes can be multiplexed or otherwise operated or controlled separately in pair-wise fashion, in order to increase or vary the overall treatment length while minimizing the power required for the treatment. This can be facilitated by concentrating power to single electrode pairs in subsequent order thereby providing heat to specific zones all at once. Two zones are depicted, however more zones can be created along the length of the device to provide longer overall treatment lengths. Each portion can then treat a separate and discrete section of the HAS to which that portion is adjacent via individual control.

Yet another variation can be to have a common wire, which has exposed section windows, and each of the other wires defines a treatment length by its section of skived window electrodes. This version typically reduces the number of wires required, yet the device could nonetheless be operated in a multiplexed fashion, as discussed above.

Any of the energy elements depicted in FIGS. 16-25 may be incorporated into any of the embodiments of the HAS treatment catheters disclosed herein (e.g., in any of the catheters of FIGS. 1-3, 4-5, 10-12, 13-15, 26) to deliver power to the fluid(s) at (or to deliver both power and fluid to) the distal tips of those catheters. Alternatively, any of these energy elements can be used as stand-alone HAS treatment devices.

Figure 26:
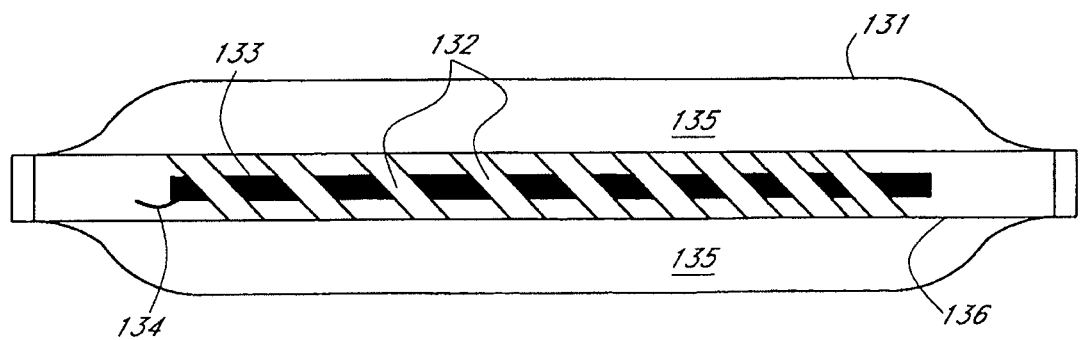
FIG. 26 is a schematic view of another embodiment of a distal portion of a HAS ligating device having a balloon.

FIG. 26 shows another embodiment of an energy element device. In this embodiment, an electrical element is housed within an expandable balloon 131. Similarly to the above embodiments, a dielectric tape 132 can be wound around a pair of electrodes 133 connected to an RF energy source (not shown) via signal wires 134. (Only one electrode 133 is shown in this view, but a similar electrode can be located opposite the depicted electrode 133.) The electrodes 133 can heat a conductive fluid 135 confined within the space created by the interior of the balloon 131 and the exterior of the inner lumen 136. The conductive fluid 135 can also be used to inflate the balloon 131. As the fluid 135 is heated by the energy flowing through it, the heat can be transferred to a HAS in which the device is positioned. This heat may be conducted into the tissue of the HAS directly from the balloon 131.

In some preferred embodiments, the balloon 131 can be made from substantially elastic materials such as silicone, or C-FLEX (i.e. any of the family of materials manufactured and sold under the trademark C-FLEX by CONSOLIDATED POLYMER TECHNOLOGIES, INC. based in Clearwater Fla.). These balloons are typically adjustable in diameter and can expand to fit within many different HAS diameters. Alternatively, the balloon can be made of PET or similar inelastic materials which predefine the balloon size. The balloon can be expanded or collapsed by at least one fluid port located on the catheter shaft and inside the balloon section. This fluid port can be configured to communicate with another lumen that runs internal to the outer catheter shaft, and it can exit in the handle 14 (see FIG. 1) utilizing a luer-type connector for connection to a fluid source.

As the balloon 131 is expanded, it can also displace any fluid, such as blood, present in the immediate treatment area of the HAS. This fluid displacement can facilitate treatment of the HAS further by removing possible heat sinks and focusing the heat more directly into the wall of the HAS.

The balloon 131 can further be configured to collapse as the HAS itself is collapsing in response to the applied treatment. By evaluating the amount of fluid forced out of the balloon at the catheter handle, treatment success or completion can be indicated. The balloon can be inflated with fluid so as to completely fill the volumetric portion of the vein it is delivering treatment to. If the fluid is then allowed to be squeezed out by the surrounding and collapsing vein wall (typically via a release valve at the proximal handle), then the amount of vein collapse can be determined by correlating the ejected fluid volume with the reduction in the internal volume of the treated HAS segment. Since HAS collapse is indicative of a successful treatment, the amount of fluid released at the proximal handle valve can be measured to indicate treatment completion.

The balloon 131 can also be manually collapsed during the last portion of the treatment cycle. This manual collapse can allow the natural collapse of the HAS being treated.

Except as further described herein, the catheters of FIGS. 1-26 can, in some embodiments, be similar to any of the catheters described in U.S. Pat. No. 6,401,719, issued Jun. 11, 2002, titled METHOD OF LIGATING HOLLOW ANATOMICAL STRUCTURES. In addition, the catheters of FIGS. 1-3, 4-5, 10-12, 13-15 and 16-26 may, in certain embodiments, be employed in practicing any of the methods disclosed in the above-mentioned U.S. Pat. No. 6,401,719. The entirety of above-mentioned U.S. Pat. No. 6,401,719 is hereby incorporated by reference herein and made a part of this specification.

Exemplary, but non-limiting embodiments of the devices of FIGS. 1-9 can be constructed as described below. Some materials that can be used are set forth in this list: polyimide tubing (e.g., amber colored with an outer diameter of approximately 0.094 inches); computer ribbon wire from disk drive cable (two strands with low-temperature insulation pulled away from ribbon); insulation displacement connector (IDC) from disk drive cable; 36 AWG copper wire (two strands about 16 inches long); solder; Devcon 5-minute epoxy; Loctite UV adhesive (line stock); Tri-Arm (line stock); two closed-end luer caps; IV extension tubeset (one male and one female luer); cable assembly (strain relief cable, Lemo connector, resistor, heat shrink tubing, black connector sleeve, solder, epoxy, flux, etc.); saline (e.g., 0.9% isotonic saline); 5 cc or 10 cc syringe.

Some equipment that can be used is set forth in this list: soldering iron; UV light source; ruler; razor blades; plastic toothpicks; scalpel and blades; tweezers; cutting tweezers; microscope; EFD dispensing tips; syringe (e.g., 3 cc); foam swabs.

The following list and figures describe a procedure that can be used for preparation and assembly of an embodiment of the inventions described herein.

Exemplary Materials and Procedures

Preparation of RF conductors:

Cut the 2-stranded computer ribbon cable to a length of 14 inches.

Using the IDC (Insulation Displacement Connector), begin regular punches of the cable at one end.

Figure 27:
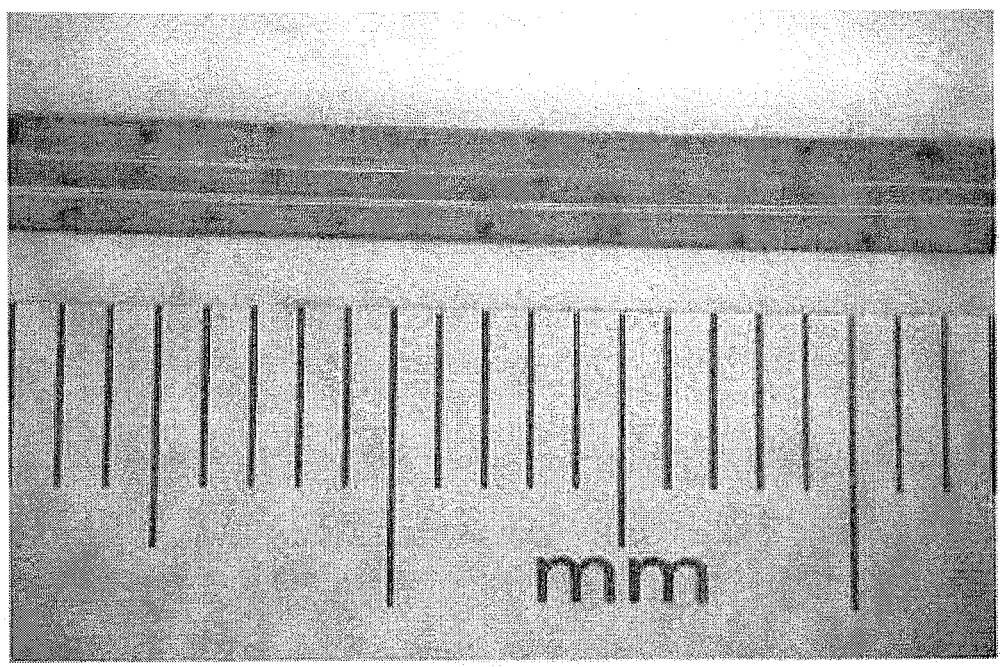
FIG. 27 is a photograph of a portion of an embodiment of a HAS ligating device during manufacture.

Continue using the IDC to make a pattern of exposed portions of electrical conductors by alternating the two rows of the IDC (line up the previous cut in one row of the IDC connector and then compress the cutting blades to add a new cut). FIG. 27 illustrates regularly-spaced cuts in the insulation of the ribbon cable, next to a ruler to show approximately how large the cuts are.

Continue making alternately spaced cuts on the insulation of the RF+ and RF− conductors (spaced 0.050 inches apart) until the distal six inches of the ribbon cable is treated with the IDC.

On the proximal end of the ribbon cable, split the two conductors and expose 2 mm of the conductor.

Cut the two pieces of 36 AWG copper wire to a length of 15 inches.

Strip both ends of the wires using a razor blade to expose 2-4 mm of copper conductor.

Solder a copper wire to each exposed (proximal) end of the ribbon cable.

Using two-part epoxy, coat the exposed portions of both solder joints. Set aside to cure.

Assembly of Shaft and Hub

Cut the polyimide tubing to a length of 11.5 inches.

Threat the ribbon cable into the polyimide tubing positioning the tip of the active RF portion of the ribbon cable within 1-3 mm of the distal end of the polyimide tubing.

Do not allow the epoxy to flow more than 3 mm into the tube. As the epoxy is curing, create a rounded tip on the end of the polyimide tubing for an atraumatic tip.

Thread the proximal end of the polyimide and the copper RF conductor wires into the distal end of the Tri-Arm. Thread the two conductors down one of the side arms leaving the polyimide tube in the main channel approximately 6-10 mm inside the Tri-Arm.

Using UV epoxy, wick adhesive between the polyimide tubing and the Tri-Arm, taking care not to allow adhesive to block the inlet to the polyimide tubing. Quickly, fully cure the adhesive using the UV light source.

Figure 28:
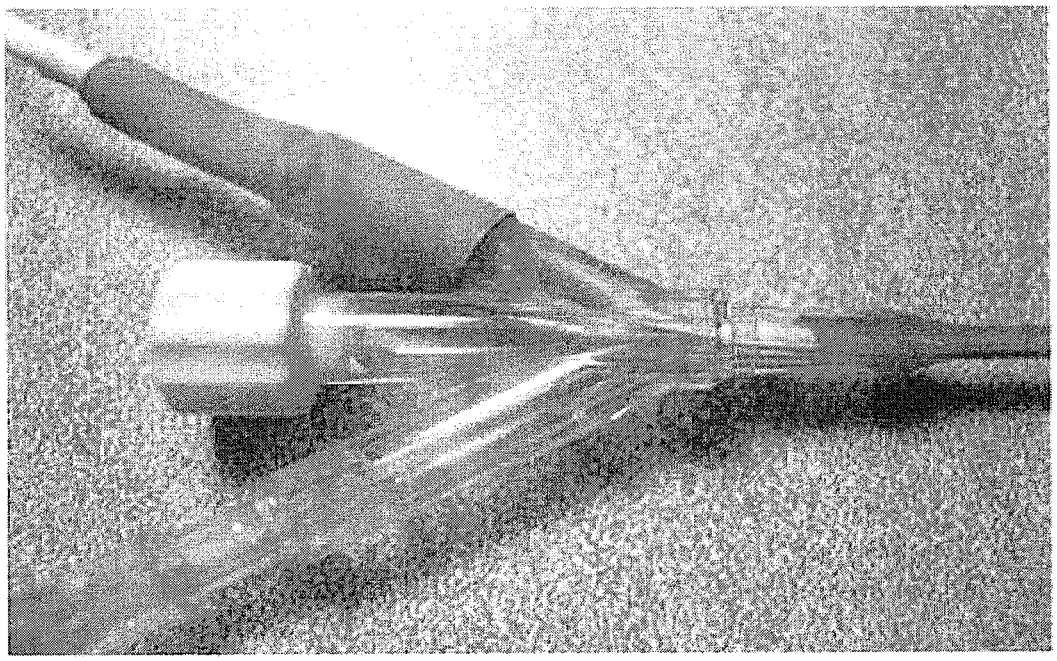
FIG. 28 is a photograph of another portion of an embodiment of a HAS ligating device during manufacture.

Using the two-part epoxy, a 3 cc syringe and 18 G dispensing tip, inject glue into the side arm with the wires to encase and seal the wires within the epoxy as shown in FIG. 28. (Note: leave room at the exit of the side arm to attach the cable assembly). Set aside to cure.

Final Assembly

Figure 29:
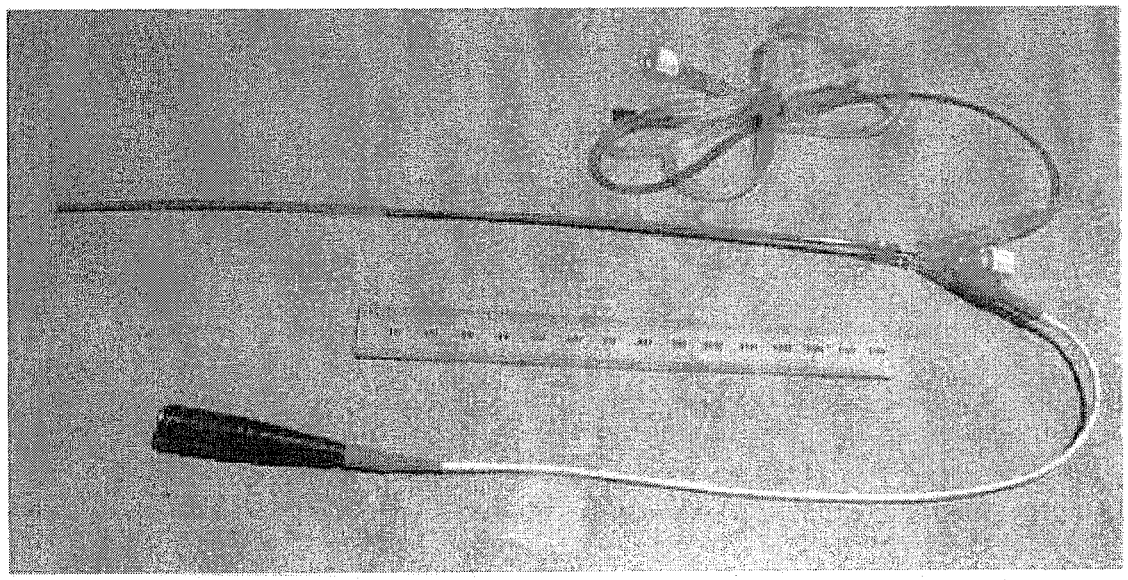
FIG. 29 is a photograph of an embodiment of a HAS ligating device during manufacture.

Integrate RF conductor wires into the cable assembly (using strain relief cable, Lemo connector, resistor for Closure 1, various heat shrink tubing for strain reliefs, black connector sleeve, epoxy, solder, flux, etc., as shown in FIG. 29.

Attach the IV extension tubeset to the side arm (e.g., the connector 20) of the Hub (e.g., the handle 14) (see FIG. 1).

Saline Priming the Device

Fill a 5 or 10 cc syringe with isotonic saline.

Uncap the ends of both the central infusion lumen and the end of the IV extension tubeset.

Inject saline into the central lumen of the Tri-Arm until most bubbles exit the end of the IV extension tubeset.

Cap the end of the IV extension tubeset.

Vary back and forth between injecting saline under pressure and then aspirating by pulling back the syringe until all of the bubbles within the polyimide tubing are gone.

Remove the syringe and cab from the central port of the Tri-Arm without trapping any air in the Hub.

The following list describes materials that may be useful for bench testing an embodiment of the inventions described above:

The medical device described above (referred to below as "RF Generator")

Catheter ID Bypass Box with Thermocouple Bypass Circuit

Two VNUS Instrument Cables

Omega thermocouple reader and thermocouple

The following list describes an example of a setup and testing procedure and method for using embodiments of the inventions described above:

Equipment Setup

Prepare the RF generator for use by plugging in the generator.

Plug one instrument cable into the RF generator and the other end into the bypass box.

Plug the second instrument cable into the bypass box and the self-regulating Hot Rod Device.

Set the bypass box's switch to Power Mode—this bypasses the thermocouple (not installed on the prototype) and operates the RF Generator in continuous power mode.

Set the generator power to the desired power setting.

Plug the thermocouple into the Omega Thermocouple Reader.

Bench Temperature Testing Procedure

Uncap the end of the IV extension tubeset.

Place the tip of the thermocouple midway along the active RF portion of the shaft.

Turn the RF generator on and record the maximum temperature achieved.

FIGS. 30-35 illustrate embodiments of heating element devices configured to apply energy to a hollow anatomical structure (HAS) by employing a capacitive structure. The devices of FIGS. 30-35 couple energy to the HAS without placing the electrical elements in direct contact with the HAS wall through a process known as dielectric heating. In some embodiments, devices can be employed as the working section of an HAS treatment catheter, e.g., at the distal tip thereof or somewhere along the length of the catheter shaft.

Many materials, both electrically conductive and non-conductive, dissipate energy when subjected to an alternating electric field through a process known as dielectric heating. Dielectric heating generally works by causing rapid movement of dipolar molecules (such as water) within a material by applying a rapidly alternating electric field, thereby causing the dipolar molecules to rapidly re-orient according to the orientation of the field. The quantity of energy dissipated in the form of heat when the material is placed in an alternating electric field depends on a material property called a "dielectric loss factor." The dielectric loss factor of a material is the product of the Dielectric Constant of the material ($\in_r$) and the Loss Tangent (tan δ) of the material.

Dipolar molecules have both positive and negative charges separated by a small distance. When an electric field is created in the vicinity of dipolar molecules, the molecules are forced to align with the field. As the polarity of the electric field alternates, the dipolar molecules rotate to align to the new field orientation. This rapid movement of the molecules effectively heats the material by internal friction. Thus, materials with more polar molecules will tend to have higher dielectric loss factors than materials with fewer polar molecules. Non-polar materials such as fat and dry tissue do not react to the electric field, and therefore, are not directly heated by capacitive RF energy.

In a typical good quality, low loss capacitor used in electronic applications, it is desirable to reduce the effects of dielectric heating. Thus, the dielectric materials of such capacitors typically have relatively low dielectric loss factors as a result of a high dielectric constant (i.e., a higher number of molecules that react to the electric field) and a small loss tangent (i.e., a measure of how much energy is lost to molecular friction). However, in situations where it is desirable to heat the dielectric material, the dielectric material preferably has a relatively large loss factor as a result of a larger loss tangent. In both cases, the dielectric material preferably includes a sufficiently high dielectric constant to achieve the desired degree of capacitance.

The degree of the dielectric heating effect depends upon the frequency of the AC power used, the RF voltage field and the loss factor of the material being heated. The equation shown below determines the heating effect:

$$P_d = 2\pi f(\epsilon_r \epsilon_0) \tan(\delta) E_{rms}^2$$

From this expression, it is apparent that power dissipation in the dielectric material increases proportionally with frequency, dielectric constant, and loss tangent.

Unlike polymeric and ceramic materials used for making most capacitors for electronic applications, the dielectric properties of biological materials change more rapidly with changing frequency. For example, as illustrated in the following table, dielectric constant ($\epsilon_r$) and loss tangent (tan δ) increase at increasing applied frequencies:

| Frequency | Saline $\epsilon_r$ | Saline tan δ | Blood $\epsilon_r$ | Blood tan δ | Blood Vessel $\epsilon_r$ | Blood Vessel tan δ |
|---|---|---|---|---|---|---|
| 100 kHz | 98 | 2752 | 5120 | 25 | 930 | 62 |
| 500 kHz | 91 | 593 | 4195 | 6 | 313 | 37 |
| 1 MHz | 84 | 323 | 2997 | 5 | 216 | 27 |
| 10 MHz | 70 | 39 | 277 | 7 | 110 | 6 |

Applying the earlier formula for volumetric heating using the values in the preceding table, and using an electric field strength of 10,000 V/m yields:

| Frequency | Saline (Pd) (w/cm³) | Blood (Pd) (w/cm³) | Blood Vessel (Pd) (w/cm³) |
|---|---|---|---|
| 100 kHz | 150 | 71 | 32 |
| 500 kHz | 150 | 70 | 32 |
| 1 MHz | 151 | 83 | 32 |
| 10 MHz | 152 | 108 | 37 |

Thus, as shown above, with all other things being equal, the highest dissipation of heat occurs in saline, and then in blood, with heat dissipation to the vessel wall occurring the slowest.

Radiofrequency generators will generally output power efficiently over a finite range of impedance and phase angle. If the source and the load impedances are not matched, a reduced amount of power is transmitted from the source to the load. In the case of dielectric heating, the load is represented by the parallel resistance created by the properties of the capacitor, i.e., dielectric constant and loss tangent.

Dielectric resistivity manifests itself both as a series and a parallel resistance with the pure capacitance. Generally, a low series resistance and high parallel resistance. The impedance presented to the RF generator is then the parallel impedance of the Rp and Cp in series with the series resistor, Rs. Since this impedance varies with frequency, either steps to match the impedance with the RFG should be performed, or an operating frequency should be selected to match the impedance of the circuit. Coupling the electric field through the dielectric is generally easier when operating at higher frequencies, because the impedance experienced by the capacitive device is lower at higher frequencies.

FIGS. 30-35 illustrate embodiments of devices capable of coupling an electric field into an HAS surrounding or adjacent the devices. The devices 500, 550, 600, 650 generally comprise an elongate structure having at least one pair of electrodes 510A, 510B, 560A, 560B, 560C, 560D, 610A, 610B, 660A, 660B, 660C, 660D, 660E, surrounded by an insulative sheath 515, 565, 615, 665 which substantially prevents direct conduction of electrical energy into surrounding fluid or tissue. For example, as shown in the embodiment illustrated in FIGS. 30-31, the electrodes 510A, 510B are generally arranged to form one or more capacitive electric fields. When an electric field is applied across the electrodes, portions of the field will extend radially outwards from the device. Thus, by rapidly alternating the polarity of the field, the dipolar water molecules in the adjacent surrounding fluid and tissue will be heated by dielectric heating. The shape and extent of the electric field can be varied by adjusting the physical geometry of the device and/or by varying electrical properties (e.g. field voltage, frequency, power, etc.) of the device 500 or power supply. Heating will generally stop when the fluid or tissue within the electric field becomes sufficiently desiccated that the electric field no longer interacts with water molecules. In this way, depth of heating penetration can be limited.

Figure 30:
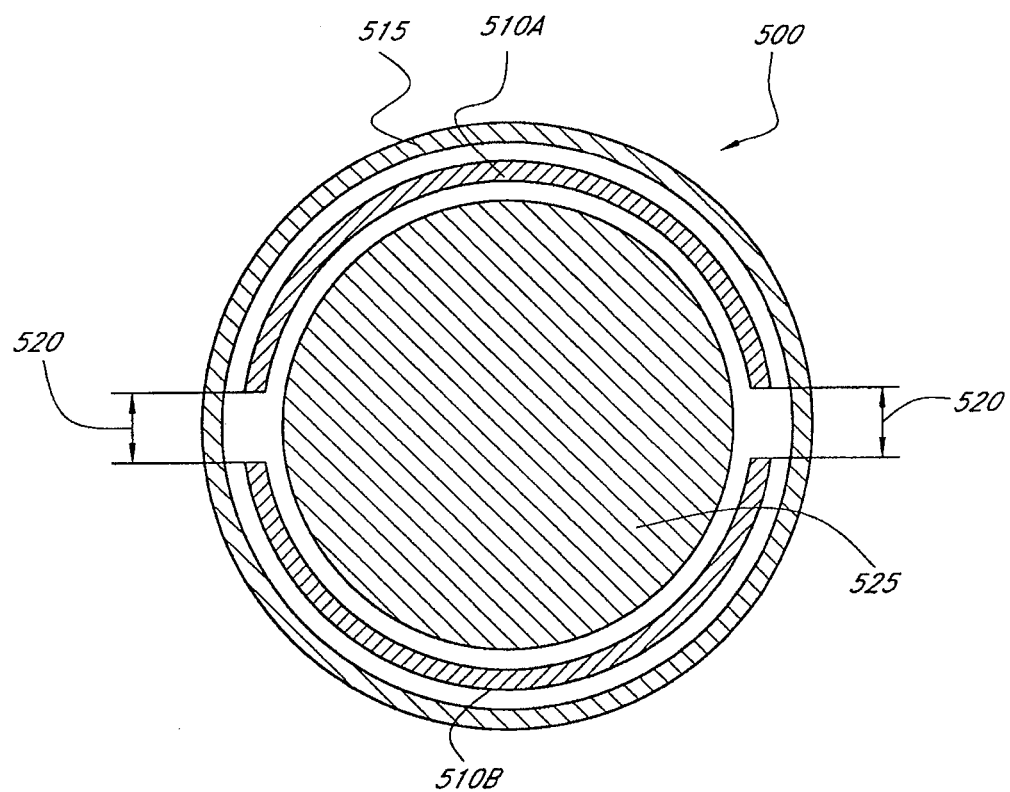
FIG. 30 is a cross-sectional view of one embodiment of a capacitive HAS heating element.
Figure 32:
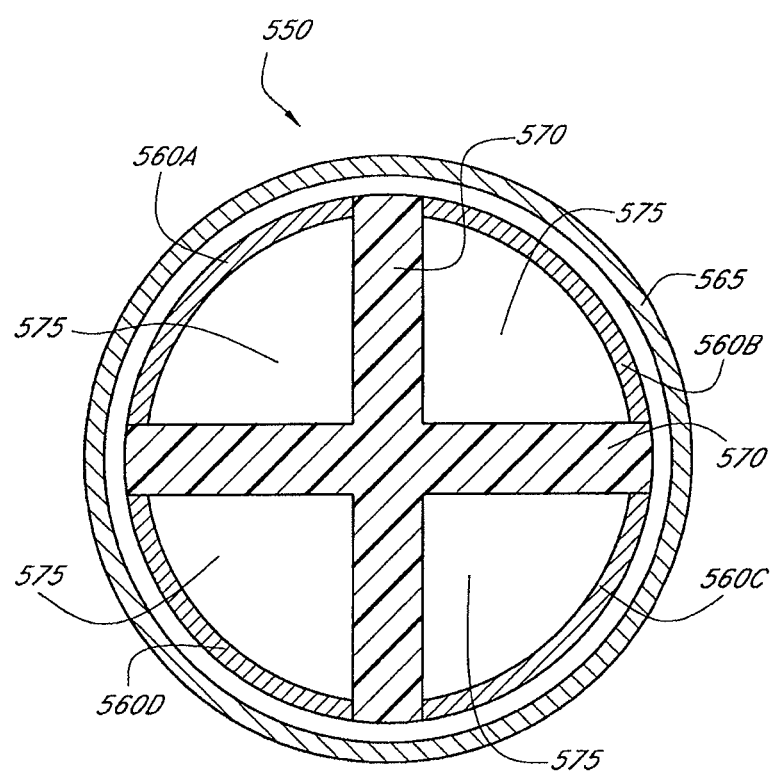
FIG. 32 is a cross-sectional view of another embodiment of a capacitive HAS heating element.

The electrodes 510A, 510B, 560A, 560B, 560C, 560D, 610A, 610B, 660A-E are preferably separated by electrically non-conductive, insulative segments 520, 570, 620, 670. For example, as shown in FIG. 30, the insulative segments 520 between the electrodes 510A, 510B can be any suitable material as desired (including air). In many embodiments, the material separating the electrodes 510A, 510B preferably has a substantially low dielectric constant, and a substantially low loss tangent relative to the same properties of the tissue to be treated. For example, in one embodiment, the tissue to be treated is a blood vessel with a dielectric constant of about 70, and a loss tangent of about 39. In one such an embodiment, a material with a dielectric constant of less than about 10 and a loss tangent of less than about 5 would be desirable. In alternative embodiments, materials with larger dielectric constants and/or loss tangents could also be used. In some embodiments, for example, as shown in FIG. 30, the device 500 can comprise a substantially solid section 525 of an electrically non-conductive material such as PEEK, Pebax, Polyimides, nylon, polyurethane, PTFE, or another suitable electrically non-conductive material. In alternative embodiments, for example, as shown in FIG. 32, the device 550 can comprise one or more substantially hollow lumens 575 to provide internal space for a guidewire, fluid infusion, optical fibers, or another purpose. In some embodiments, the device can include a partial separator between the electrodes, thereby dividing the internal space into two or more parallel lumens.

The outer non-conductive sheath 515, 565, 615, 665 surrounding the electrodes preferably are made of a material that is substantially electrically non-conductive, yet is substantially "invisible" to the RF field at the applied frequency. For example, many polymers will have sufficiently few dipolar molecules as to be substantially unaffected by the alternating electric field across the electrodes elements. It is believed that, at sufficiently high frequencies (e.g., about 10 to about 30 MHz), materials such as PET, PTFE, FEP, PE Polyolefin (or other materials with dielectric constants and loss tangents that are appreciably less than the same properties of the biological structure to be treated) will be substantially unaffected by RF power in the electrodes. The thickness of the outer sheath is typically minimized to substantially limit the amount of heating experienced by the sheath, yet remains thick enough to provide adequate electrical insulation and to resist melting due to contact with the heated tissue.

Figure 31:
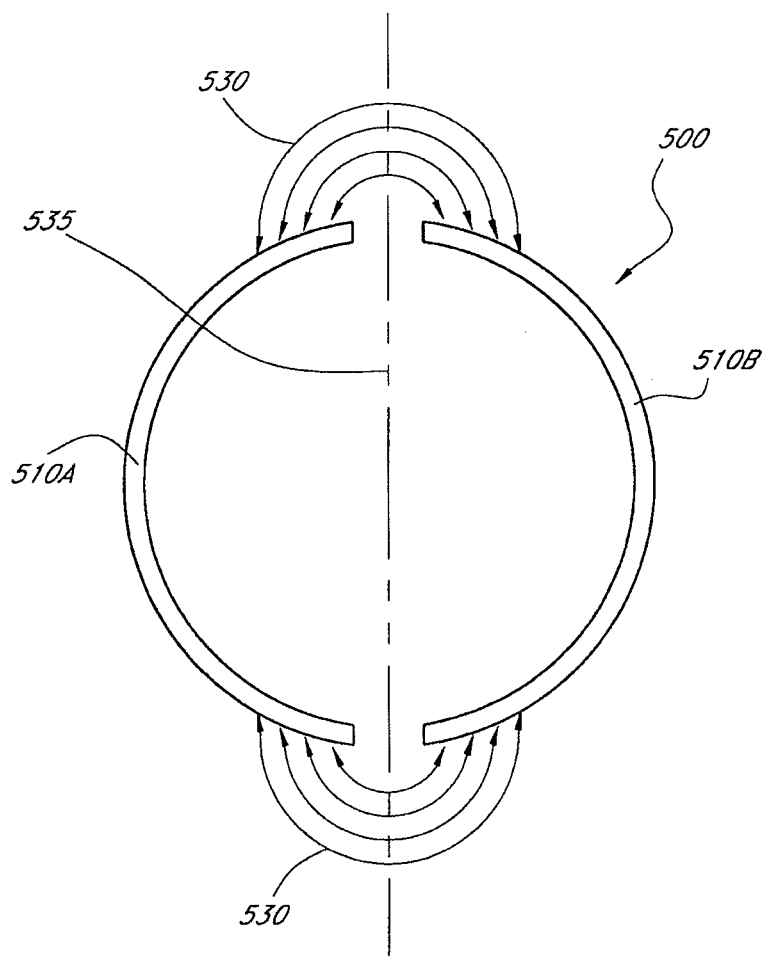
FIG. 31 is a schematic view illustrating an electric field generated by the device of FIG. 30.

FIGS. 30 and 31 illustrate one embodiment of a capacitively coupled thermal element 500 which generally comprises first 510A and second 510B electrodes separated by an insulating section 520, such as an air gap or a section of an insulative material. For example, in one embodiment, the first 510A and second 510B electrodes comprise elongate sections of semi-cylindrical electrically conductive elements. The device 500 of FIGS. 30 and 31 will couple an electric field 530 into the tissue with electric field lines extending radially around the device 500. Thus, heating will occur along the contour lines of electric field, which are strongest along the plane 535 separating the first 510A and second 510B semi-cylindrical electrodes. Thus, in one embodiment, the device 500 of FIGS. 30 and 31 is rotated during use (e.g., when the electric field 530 is being generated) along its axis in order to apply even heating to the surrounding HAS tissue and/or fluid.

Figure 33:
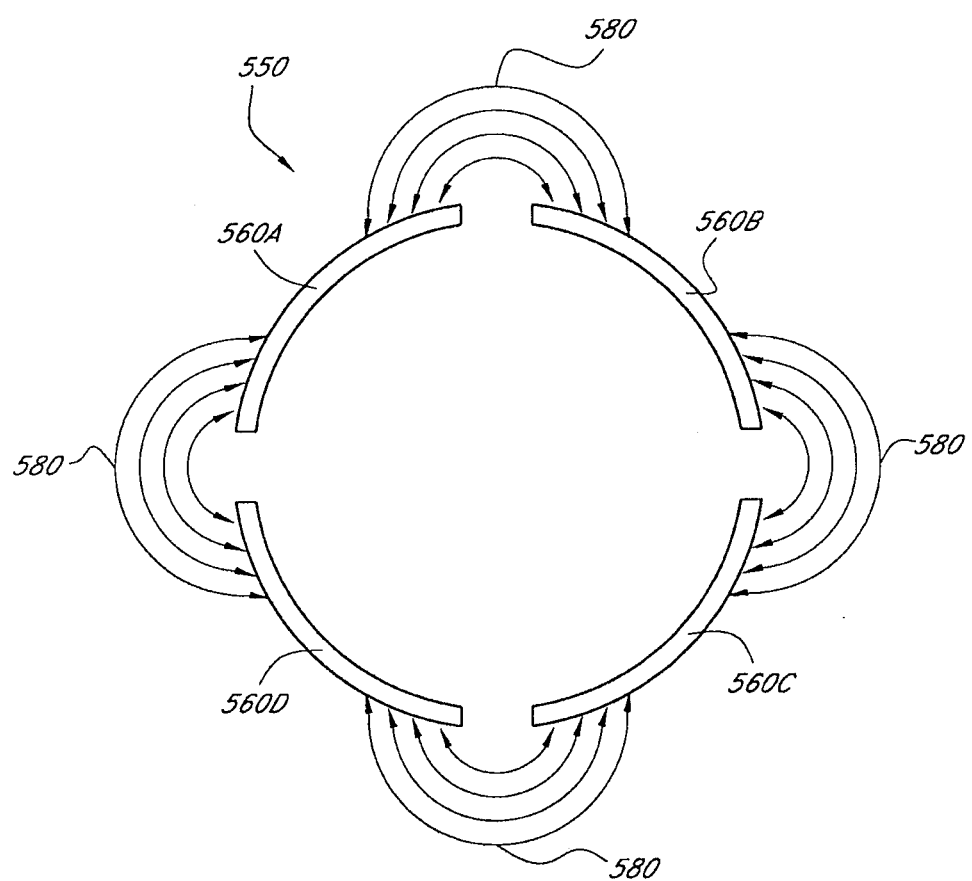
FIG. 33 is a schematic view illustrating an electric field generated by the device of FIG. 32.

In an alternative embodiment, illustrated for example in FIGS. 32 and 33, four or more elongate electrodes 560A, 560B, 560C and 560D can be provided around the circumference of the device 550. The four sections 560A-D can be connected to a power supply with alternating polarity. For example, the segment at 12 o-clock to 3 o-clock and the segment at 6 o-clock to nine o-clock can be a positive polarity when the segments at 9-12 o-clock and 3-6 o-clock are negative. Such a device will generally form electric field lines 580 along multiple planes as shown in FIG. 33, thereby providing heating around more of the circumference of the device. In some embodiments, the electrodes 560A-D may extend linearly along a catheter, thereby forming one or more substantially planar areas of maximum field strength. The electrodes of FIGS. 30-33 are shown as cylindrical sections. However, the electrodes can comprise any other cross-sectional shape as desired, such as planar, rectangular, triangular, etc.

Figure 34:
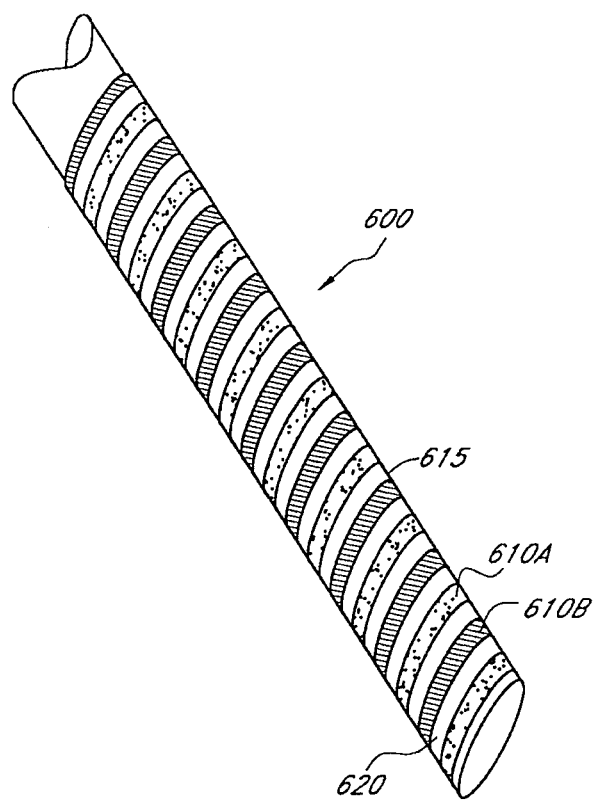
FIG. 34 is a schematic perspective view of one embodiment of a capacitive HAS heating element having a pair of helically-wound electrodes.

In an alternative embodiment, illustrated for example in FIG. 34, the electrodes can be wound around the catheter in a helical pattern, or otherwise coiled around the catheter shaft. Wrapping the first 610A and second 610B electrodes in a helical pattern along the device provides a number of advantages. For example, the helical pattern of maximum field strength achieved with a pair of helically wound electrodes can create a more uniform distribution of energy around the circumference of the device and along the length of the device. The spacing between adjacent windings can be adjusted in order to achieve a desired field pattern and energy distribution. Additionally, helically wound electrodes will typically offer more flexibility and maneuverability to the device than linear electrodes.

In some embodiments, the electrodes extend along substantially an entire desired working length. For example, in some embodiments, the electrodes can have an operative length of anywhere from one to sixty cm. For example, in some embodiments, total working lengths of 9 cm, 15 cm, 30 cm, 45 cm or other lengths can be used as desired. In some embodiments, variable length treatment devices may be constructed by providing a plurality of discrete segments along the axis of the device. The operative length of the device can then be varied by activating or de-activating one or more pairs or sets of discrete segments as desired.

The elongate electrodes can be made of any suitable material, such as copper or other conductive metallic tape, etched flex circuits, metalized polymer substrates (e.g., formed by vapor deposition or other process). In some embodiments, a metallic tape can be co-extruded into an elongate catheter. In some embodiments, the electrodes are preferably substantially flexible to allow the device to be guided to a desired treatment site.

Figure 35:
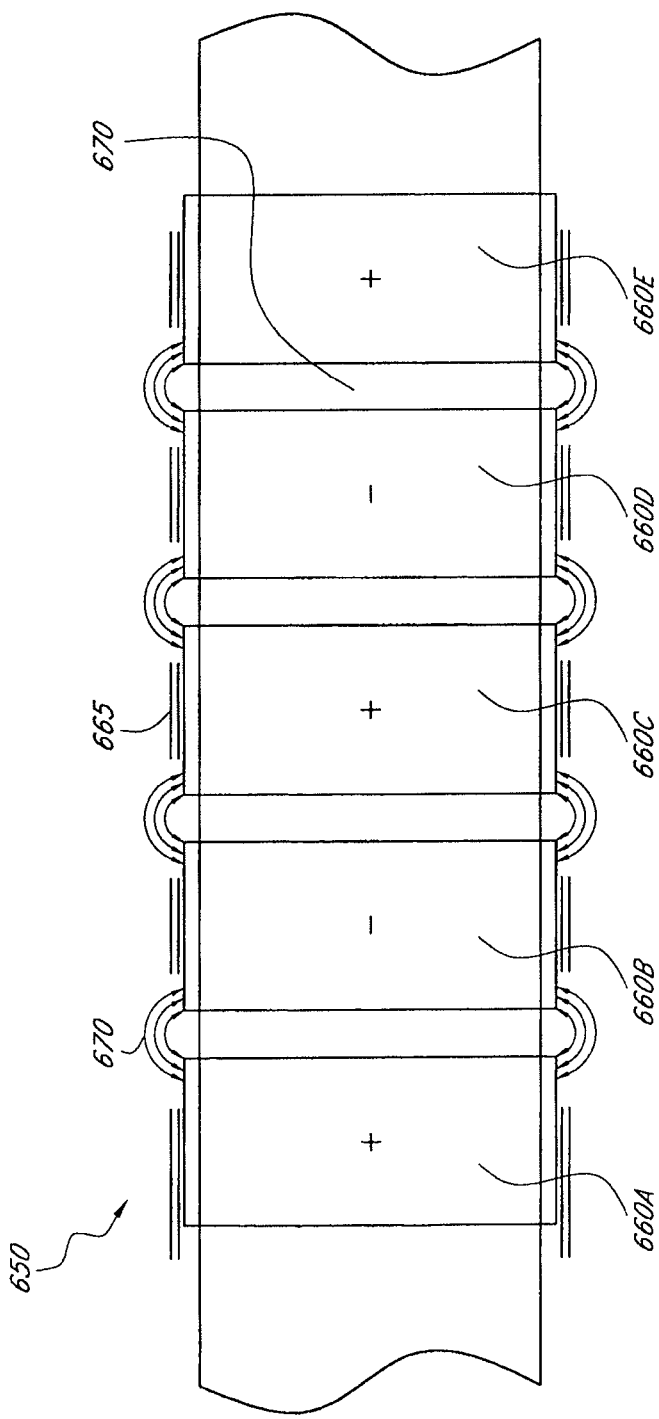
FIG. 35 is a schematic view of an alternative embodiment of a capacitive HAS heating device.

FIG. 35 illustrates another embodiment of a capacitively coupled HAS heating element 650 comprising a plurality of axially-separated rings 660A-E. The rings 660A-E are joined to a power supply in an alternating positive/negative manner, such that electric fields 670 can be created at the junctions of the rings 660A-E. Thus, an operative length of the device 650 can be varied by applying RF power to a select number of rings 660A-E along a desired length or section of the device 650. If desired, the device 650 can be pulled and/or pushed axially in order to increase uniformity of heating the HAS wall.

Embodiments of methods for using devices such as those illustrated in FIGS. 30-35 will now be described. In one embodiment, a device having a plurality of elongate electrodes is inserted into an HAS and guided to a desired treatment site. Once the heating element of the device is positioned at the treatment site, RF power can be applied to the electrodes. The device can be rotated about its longitudinal axis and/or pushed or pulled axially in order to provide even heating of the HAS wall. In some embodiments, the device can be pulled proximally or pushed distally during treatment in order to affect a section of the HAS longer than the operative section of the device. In alternative embodiments, the power supplied to the heating element can be stopped before re-positioning the device in a different section of the HAS, or in a different HAS altogether. Once the device is re-positioned, power can again be supplied to the heating element for treatment of the new site.

In some embodiments, any of the devices of FIGS. 30-35 may have multiple, separately operable electrodes or separately operable electrode pairs (e.g. each electrode/pair having a separate power delivery conductor or otherwise being separately addressable for power application). Thus, when used with an appropriate control system, subsets of the available electrodes/pairs can be operated sequentially in a "multiplexed" fashion (e.g., similar to the multiplexed mode of operation depicted in FIG. 41 and described below). Any of the techniques or modes described below for multiplexed operation of electrodes can be used in conjunction with any appropriate embodiment depicted in FIGS. 30-35 when multiple, selectively or separately energizable electrodes/pairs are provided as part of the device. The devices may therefore include a control unit configured to sequentially energize selected subsets of the entire set of electrodes/pairs on the shaft. The control unit may include an appropriate multiplexing or sequential-operation algorithm (e.g., program instructions) stored in memory and executable by a processor of the control unit, to selectively operate the electrode/pair subsets as desired.

The devices of FIGS. 30-35 advantageously have very simple constructions requiring no moving parts. These devices can also advantageously provide substantially long working sections, thus requiring minimal movement of the device during treatment. The devices of FIGS. 30-35 also advantageously reduce the need for physical contact between the device and the HAS wall, and substantially reduces the need for the device to be centered within the HAS.

Although many of the forgoing embodiments have been described in the context of treating a hollow anatomical structure (such as a blood vessel), it should be understood that the above embodiments are not necessarily limited to such uses. For example, the systems and devices described herein can be used for any clinical procedure in which it is desirable to apply energy to anatomical, biological, or foreign structures within a patient.

In some respects, some embodiments of the devices described herein may be similar to one or more of the catheters described in U.S. Pat. No. 6,401,719, issued Jun. 11, 2002, titled METHOD OF LIGATING HOLLOW ANATOMICAL STRUCTURES. In addition, the devices described herein may, in certain embodiments, be employed by practicing any of the methods disclosed in the above-mentioned U.S. Pat. No. 6,401,719, the entirety of which is hereby incorporated by reference herein and made a part of this specification.

The features of a system and method having electrode elements will now be described. The drawings, associated descriptions, and specific implementation are provided to illustrate embodiments of the invention and not to limit the scope of the invention. In addition, methods and functions described herein are not limited to any particular sequence, and the acts or states relating thereto can be performed in other sequences that are appropriate. For example, described acts or states may be performed in an order other than that specifically disclosed, or multiple acts or states may be combined in a single act or state.

Figure 36:
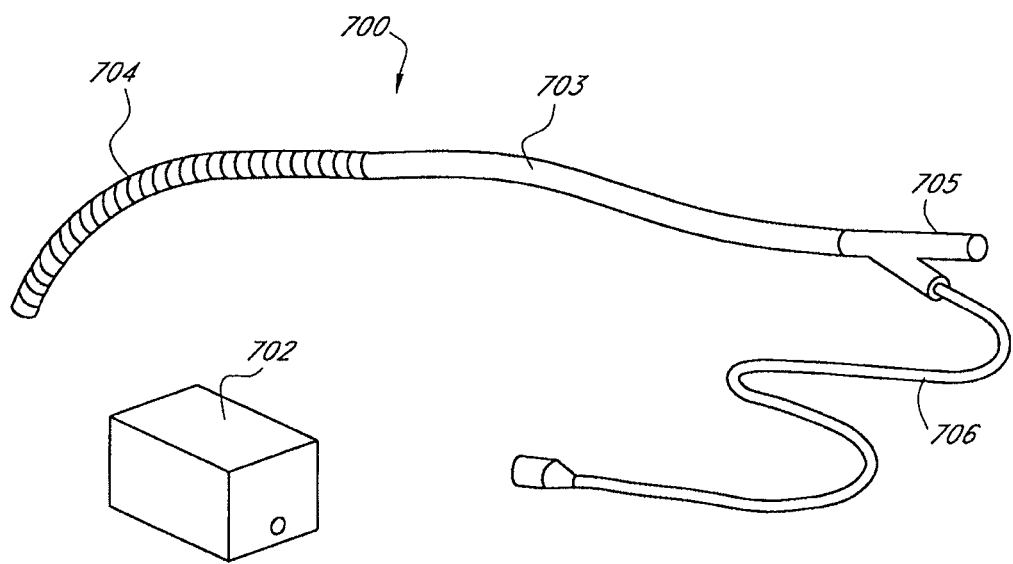
FIG. 36 illustrates an overall view of an RF element system according to one embodiment.

FIG. 36 illustrates an embodiment of an RF element system for applying energy to the wall of a hollow anatomical structure such as (but not limited to) the inner wall(s) of a vein, e.g. a varicose vein. As illustrated, the RF element system comprises a catheter 700. The catheter 700 includes a catheter shaft 703, which may be used to maneuver the distal or working portion 704 of the catheter 700 during placement. In one embodiment, the catheter shaft 703 comprises a biocompatible material having a low coefficient of friction. For example, the shaft 703 may comprise a polyimide. In other embodiments, the shaft 703 may comprise Teflon®, Hytrel®, or any other such suitable material. In one embodiment, the catheter shaft 703 is sized to fit within a vascular structure that may be between 2 and 14 French, but preferably between 4 and 8 French, which corresponds to a diameter of between 1.3 mm (0.05 in) and 2.7 mm (0.10 in), or other sizes as appropriate. The distal portion 704 transfers energy (e.g., RF energy where the distal portion comprises one or more RF electrodes) to an inner vein wall. The proximal end of the catheter has a handle 705. The handle 705 includes a port for fluid and a connection 706 for interfacing with an energy source 702.

In one embodiment, an energy source 702 comprises an alternating current (AC) source. In other embodiments, the energy source 702 comprises a direct current (DC) power supply, such as, for example, a battery, a capacitor, or other energy source. In some embodiments, the energy source 702 preferably comprises an RF generator powered by an AC or DC supply. The power source 702 may also incorporate a controller that, by use of a microprocessor, applies power using a temperature sensor located in the working portion of the catheter 700. For example, the controller may heat the tissue of a hollow anatomical structure to a set temperature. In an alternate embodiment, the user selects a constant power output of the energy source 702. For example, the user may manually adjust the power output relative to the temperature display from the temperature sensor in the working portion of the catheter 700.

Figure 37:
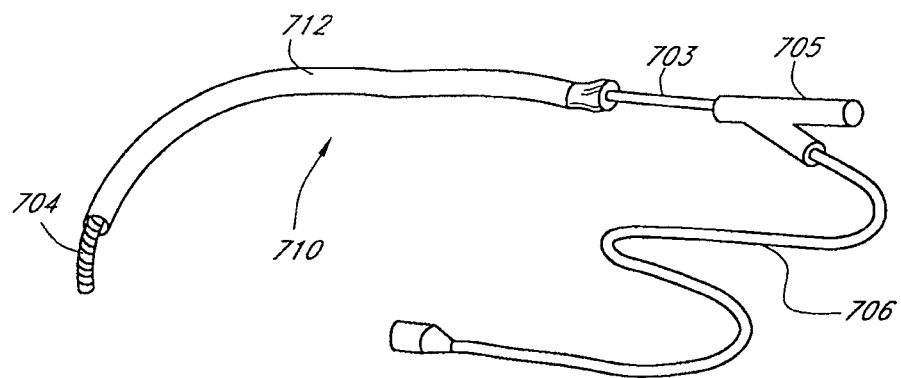
FIG. 37 illustrates an exemplary embodiment of a catheter sheath in a partially retracted position usable with the RF element system of FIG. 36.

FIG. 37 illustrates another embodiment of an RF element system similar to the embodiment of FIG. 36 except as described below. As shown, the catheter 710 includes an outer retractable sheath 712. The sheath 712 is advantageously used to protect the device during placement, facilitate introduction of the device, and/or adjust the exposed axial length of the electrode element for a user-selected and variable treatment length. For example, the sheath 712 may be used (e.g., pulled back (proximally) or pushed forward (distally)) to adjust the length of the region of the catheter that is exposed to a wall of the hollow anatomical structure.

In some embodiments, the catheter 710 has an internal lumen. The lumen preferably communicates between the distal tip and the proximal handle. The lumen may be used for fluid delivery such as saline, a venoconstrictor, sclerosant, high-impedance fluid, adhesive, hydrogel, or the like. In one embodiment, the catheter lumen can be used to apply a venoconstrictor prior to treatment with the electrode element. Application of a venoconstrictive agent to an interior portion of a hollow anatomical structure, e.g., a vein, can improve the apposition of the energy applying device to the structure wall. Venoconstrictive agents, when suitably applied, rely on the body's own physical reaction to the agent to contract and collapse around the therapeutic device.

The venoconstrictive agent preferably is easily applied over the target treatment length to enhance the performance of the device. The venoconstrictive agent preferably is non-toxic, well tolerated, effective in both sedated and non-sedated patients, and substantially free of adverse side effects. The venoconstrictive agent preferably is metabolized relatively quickly. Some embodiments comprise one or more of the following exemplary venoconstrictive agents: phenyl ephrine, high-concentration K+ solution, sumatriptan, dihydroergotamine, 5-hydroxytryptamine (or an equivalent that can bind to 5-HT1 receptors found in the saphenous vein), and other suitable agents.

In one application, the venoconstrictive agent is administered by direct injection to the interior of the hollow anatomical structure. In other applications, the venoconstrictive agent can be administered by superfusion to the exterior surface via injection, by systemic injection, or by other suitable methods. Application of the venoconstrictive agent may be made through the energy delivering device (e.g., the catheter 710), through another specialized delivery device, or through a nonspecialized delivery device. In some embodiments, occlusive methods, e.g., manual compression surrounding the area of interest, the use of a balloon, insertion of bioabsorbable occlusive elements or adhesives, can be used to locally isolate the venoconstrictive agent.

External physical and/or manual compression can also improve the apposition of the energy applying device to the structure wall. Compression methods can include external mechanical means to achieve compression, such as, for example, tumescent anesthesia, manual compression, vessel collapsing mechanisms that include spreadable opposed elements, reciprocating jaw mechanisms having penetrating elements, and devices for applying negative pressure to collapse the blood vessel.

Reducing the intra-luminal diameter of the vein can decrease the distance between the vein wall and the energy delivering device to increase the efficiency and uniformity of energy delivery to the vein wall. The vein can then be treated with the RF electrode element to further shrink the vein.

Upon completion of treatment, a hydrogel may be exuded from the distal catheter end allowing for complete vessel occlusion. For example, the hydrogel may be biocompatible or bioresorbable. In other embodiments, the hydrogel may be displaced by the constriction of the hollow anatomical structure resulting from the thermal injury response which results in substantially complete occlusion. In those sections of the hollow anatomical structure in which the material has not completely compressed, it can be resorbed by the body naturally. In yet other embodiments, the lumen may also accommodate a guide wire for catheter placement.

Figure 38:
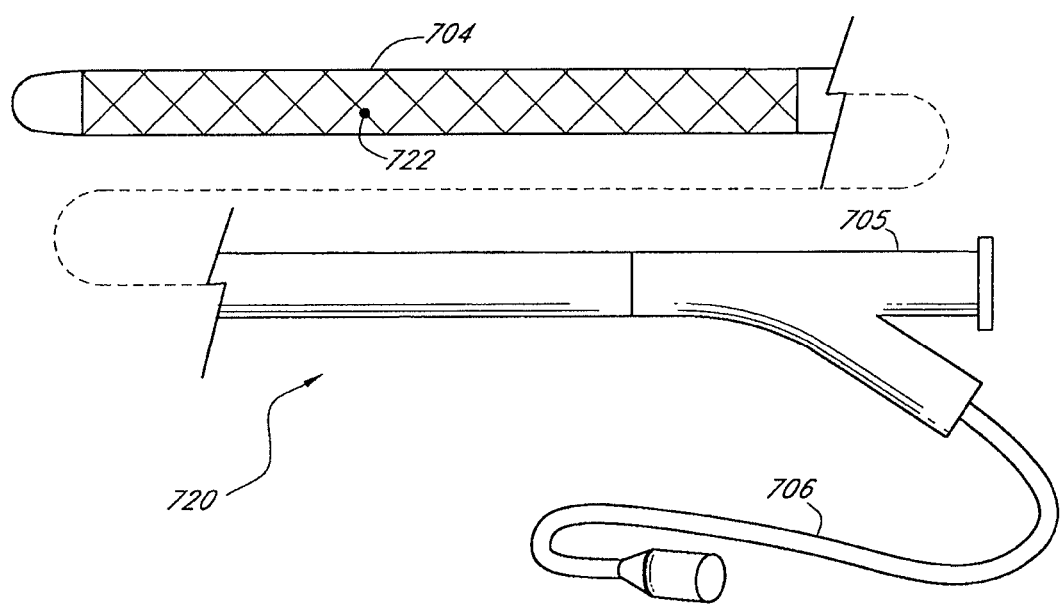
FIG. 38 illustrates a closer view of an exemplary embodiment of a catheter usable with the RF element system of FIG. 36.

FIG. 38 shows another embodiment similar to the embodiments described and depicted in FIGS. 36-37 above, except as noted below. A catheter 720 comprises a temperature sensor 722 as part of the electrode. In other embodiments, multiple sensors are placed along the axial electrode length. In some embodiments, the energy source can advantageously monitor individual sensors and use the multiple inputs for temperature feedback. In another embodiment, the controller may monitor for high temperature or low temperature signals. For example, an algorithmic process may be used to control the electrodes, thus maintaining a substantially axially-uniform temperature and/or heat output.

Figure 39:
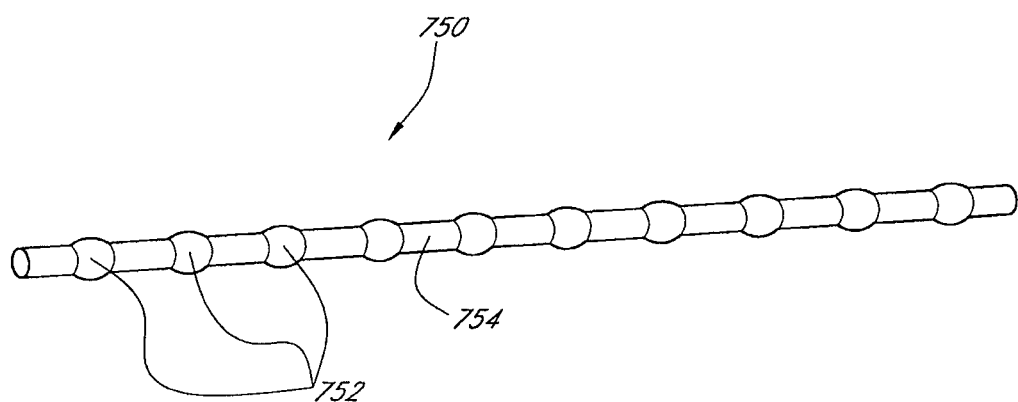
FIG. 39 illustrates a side view of another embodiment of the working end of the catheter of FIG. 38.

Some embodiments comprise a multi-ball configuration employed with or without a multiplexing process. For example, FIG. 39 illustrates one embodiment of the working end 750 of a catheter such as the catheter shown in FIGS. 36 and 37. The working end 750 comprises separate distinct protruding electrode elements 752 preferably comprising non-corrosive and biocompatible materials such as, for example, stainless steel or platinum. To improve the tissue heating by the electrode, the protruding elements 752 preferably are hemispherically shaped. In other embodiments the protruding elements can be other suitable shapes. The elements 752 preferably are spaced axially along the catheter shaft 754. In the illustrated embodiment, each element 752 preferably is attached to a signal wire by solder or spot weld. The signal wire, not shown, preferably is placed internal to the catheter tube and attached to the connector 706, as shown in FIG. 36. One or more temperature sensors can be positioned on or near one or more of the electrodes.

In some embodiments, one or more electrode elements can be temperature controlled by having a temperature sensor as shown in FIG. 38 in a monopolar mode. In other embodiments, one or more pairs of electrodes can be temperature controlled in a bipolar mode by having a temperature sensor located on or near one or more of the electrode pairs. In another embodiment, the sequential electrode elements are used in a power control mode relying on manual energy control.

Alternatively, in one embodiment having multiple electrode elements, a temperature sensor is located on the most distal electrode. For example, the most distal electrode may be used for the initial treatment profile, and the successive electrode pairs may use the same and/or a predetermined energy-time profile.

Figure 40:
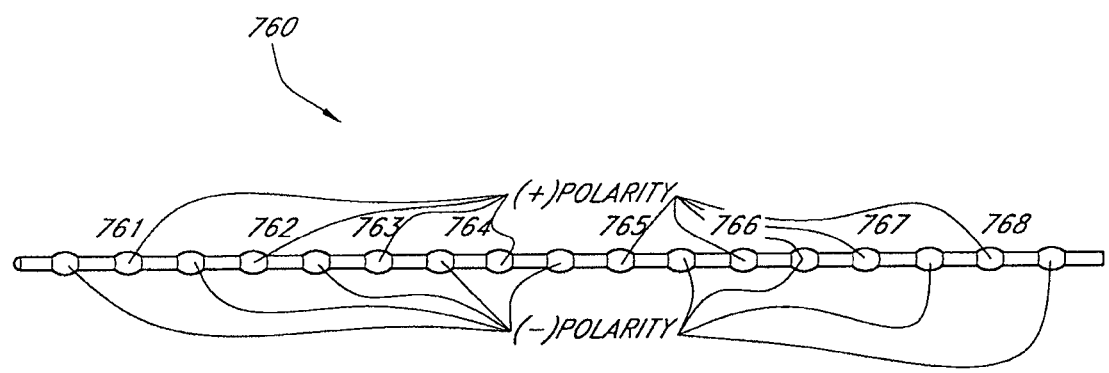
FIG. 40 illustrates a side view of the device of FIG. 39.

In one embodiment, a method of use of the RF electrode element system 760, which is similar to the system described with reference to FIG. 39, except as noted below, includes multiplexing through each of the electrode elements 761-768 shown in FIG. 40. The term "multiplex" as used herein is a broad term and is used in its ordinary sense and includes without limitation the energizing, or heating, of at least one active electrode element for a specific dwell time and cascading, or moving to another active electrode element until the end active electrode element is reached or until a cycle is completed. The cycle is then repeated until the complete treatment time is reached.

Each tissue section adjacent to an electrode preferably is kept at the treatment temperature by cycling through the electrode sequence within a defined time. With reference to FIG. 40, the electrode element configuration has eight active electrodes. In the illustrated embodiment, active electrodes 761 through 768 are indicated as having positive (+) polarity and the other nine return electrodes are indicated as having negative (−) polarity. The indicated polarity is merely exemplary. Where the energy source 702 comprises an AC source there is not really a polarity, but the indication of polarity is helpful to identify the active and return electrodes in the illustrated embodiment. Each of the active electrodes has two adjacent return electrodes. This is to increase and spread the RF tissue heating length and to create a uniform treatment length via an overlapping mechanism. In one embodiment, the return (−) electrodes are sequenced so that the relevant ones are 'on' when the adjacent active (+) electrodes are 'on.' In another embodiment, the return (−) electrodes are 'on' as a group, working with the relevant energized active (+) electrodes.

In one embodiment, the electrode elements 760 through 768 are sequentially energized for a dwell time of 0.2 seconds. In the example shown, three electrode elements are powered at a time. The table in FIG. 41 has shaded blocks of time, which represent the time that energy is being delivered to the specified active electrode elements. Since three electrode elements are on at one time, and the dwell time is 0.2 seconds, each electrode element is on for a total of 0.6 seconds during one cycle. In the table, for time 0 to time 0.2 seconds, electrode elements 761, 762 and 763 are energized. For time 0.2 seconds to 0.4 seconds electrode elements 762, 763 and 764 are energized. This process repeats by stepping through the electrode element set. For the 8 active electrode elements shown, one complete cycle takes 1.6 seconds.

Figure 41:
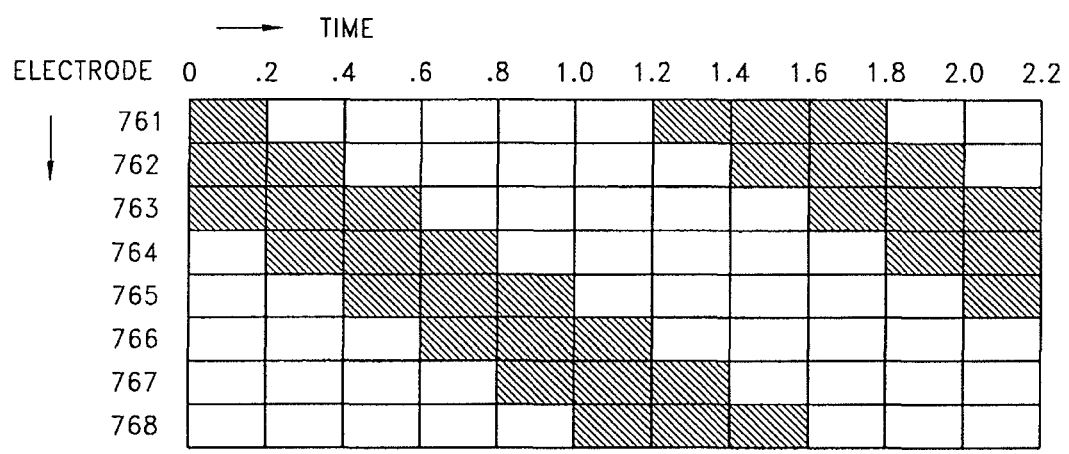
FIG. 41 illustrates a table depicting an exemplary treatment cycle usable with the catheter of FIG. 39.

In one embodiment, to avoid overcooling of a particular electrode element, the cycle time for the 8 active electrodes is of a short duration and/or the total number of electrode elements is limited. That is, in one embodiment, an electrode element may be re-energized before substantial cooling takes place. In addition, in one embodiment, to increase the treatment zone, the catheter may comprise multiple treatment zones, such as, for example, groups of eight electrode elements, as is shown in FIG. 41. Each group of eight electrode elements may treat the wall of the hollow anatomical structure before energy is applied to the next group of electrode elements. Alternative modes of multiplexing may also be employed. For example, the number of adjacent electrode elements simultaneously energized may vary. Also, the entire cycle may re-start at the first end energized, or the last end energized. Another mode of multiplexing may be accomplished through a sensing of the tissue impedance. Once a certain level is achieved, the next set of electrode elements is then energized.

Alternatively, at least one of the eight active electrode elements is energized to treat the hollow anatomical structure until treatment is complete. Then, the next active electrode element(s) apply a similar treatment time, and so on moving along the treatment zone. For the eight active electrode elements illustrated in FIG. 40, the treatment may be for one cycle. For example, active electrode element 761 may treat the hollow anatomical structure for 40 seconds. Once electrode element 761 has completed treatment, electrode element 762 repeats the same treatment time and energy settings. Such a process may continue for active electrode elements 763 through 768.

In other embodiments, alternate treatment cycles may be used. For example, active electrode elements 761 and 762 may concurrently treat the hollow anatomical structure for 40 seconds. Then, active electrode elements 763 and 764 apply a similar treatment, and so forth through active electrode elements 767 and 768 to complete the cycle.

Figure 42:
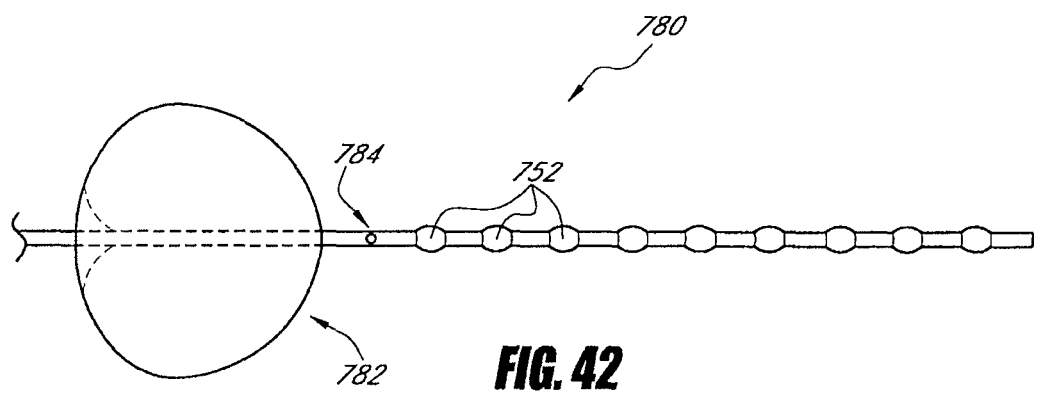
FIG. 42 illustrates a side view of another embodiment of an RF element system including an expandable balloon and a set of fluid ports.

FIG. 42 is another embodiment of the working portion of the catheter of FIG. 39. The device 780 has a balloon 782. The balloon 782 preferably is expandable by internal ports to the balloon. The illustrated device has one balloon located at one end of the electrode set. Additional fluid ports 784 proximal to the electrode elements 752 are preferably provided for fluid placement within the hollow anatomical structure.

In one embodiment, the catheter 780 is placed in the hollow anatomical structure, and then the balloon 782 is inflated through the internal ports. Once the balloon is inflated and in apposition to the vein wall, the fluid ports 784 preferably clear the treatment zone of the hollow anatomical structure of native fluid, such as blood, distal to the balloon 782, by injecting displacing fluid, such as, for example, saline. In one embodiment, the displacing fluid is followed by another injection of a venoconstrictor, which reduces the hollow anatomical structure lumen size prior to treatment. By temporarily reducing the hollow anatomical structure's size, the treatment time used for the active electrode elements 752 is reduced, thereby resulting in a shorter, safer and more effective treatment. Additionally, in one embodiment, constricting the hollow anatomical structure exsanguinates it of blood, enhancing the functionality of the device by reducing coagulum formation and promoting a better long-term efficacy by reducing the thrombotic occlusion.

In another embodiment, the device has a balloon at each end of the electrode set. The proximal balloon is inflated. A displacing fluid (as discussed above) is delivered using the fluid ports 784. The distal balloon preferably is partially inflated prior to fluid delivery and then fully inflated after fluid delivery to help isolate displacing fluid within that section of the hollow anatomical structure.

Figure 43:
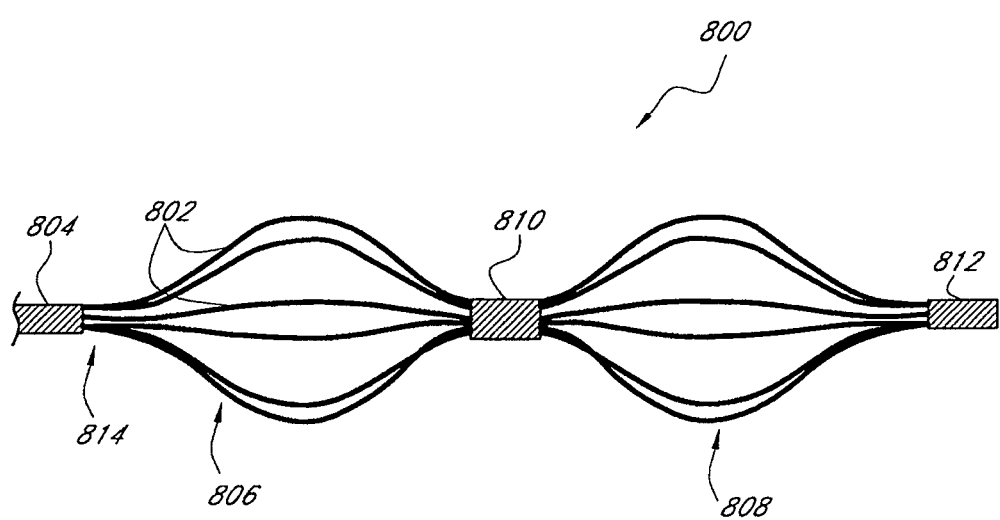
FIG. 43 illustrates an exemplary embodiment of an expandable set of spline electrodes capable of conforming and contacting a vein wall.

With reference to FIG. 43, one embodiment of an RF system 800 uses at least one expandable spline. The pre-shaped splines 802, six splines in this figure, act as individual electrode elements. The set of splines 802 are attached radially about the catheter shaft 804. The expandable electrode element set has at least one expandable section. In FIG. 43, the device shown has two expandable sections 806, 808. The electrode element set is anchored at the mid point 810, which does not substantially expand. The tip 812 and proximal end 814 attached to the shaft 804 also do not substantially expand.

In some embodiments, one or more electrode splines comprise one or more electrode elements. In one embodiment, a bipolar device comprises a plurality of electrodes on one or more splines. In another embodiment, a bipolar device has a plurality of splines having opposite polarities. In one embodiment, the electrode sets of each spline preferably are staggered relative to one another to form a checkerboard-like pattern. The checkerboard-like pattern preferably limits the likelihood that the electrodes will contact each other in the collapsed configuration. The exposed electrode portions preferably are positioned on the outer surface or face of the spline to contact a vein wall.

The device is designed to collapse by use of an outer sheath, which in FIG. 43 is in a retracted position. For example, the sheath may be used to help place the device in the vessel and to help remove the device after treatment. In another embodiment, the sheath is used to limit the treatment length. For example, a physician using an embodiment of the device having four segments can limit the treatment length by selectively deploying less than four segments from the sheath for treatment.

The self-adjusting splines preferably allow an appropriate amount of expansion for apposition to the tissue, while adjusting axially to bends or curves in the hollow anatomical structure. As the hollow anatomical structure is heated during treatment, the lumen preferably constricts and/or shrinks. The spline set preferably adjusts and collapses concurrently with the hollow anatomical structure. This same characteristic also gives the device of FIG. 43 versatility, as it is able to accommodate varying diametrical sizes of hollow anatomical structures.

Alternatively, the device comprises a stylet wire attached to the distal tip and placed axially and internally to the catheter in order to collapse and expand the pre-shaped splines. In this embodiment, the splines may be manually collapsed during treatment to duplicate the collapse or lumenal reduction of the hollow anatomical structure.

In some embodiments, each spline 802 is made of a spring type material such as Nitinol®. Other nickel based spring alloys, stainless spring alloys, 17-7 stainless, Carpenter 455 type stainless, or other non ferrous alloys such as beryllium copper can also be used. A temperature sensor can also be attached to one or more splines for temperature controlled energy delivery. Each spline 802 thus comprises a conductor which is covered in insulation over most of its length. To form one or more electrodes the insulation is skived away from portion(s) of the outward-facing surface of the spline(s) to selectively expose the underlying conductor.

Figure 44:
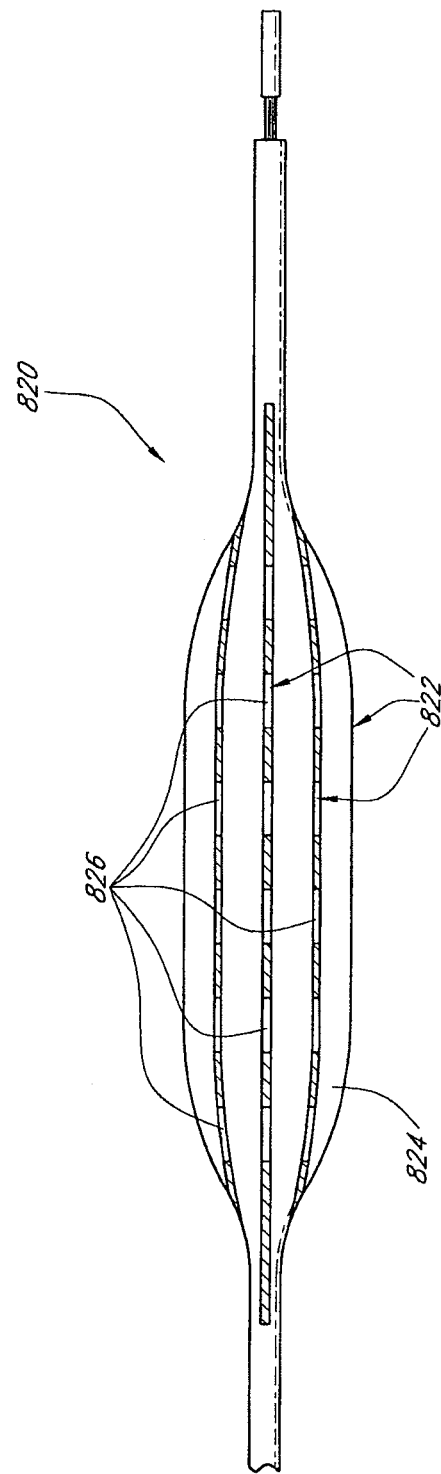
FIG. 44 illustrates an exemplary embodiment of an expandable set of spline electrodes having a long expandable section with a plurality of electrodes on each spline.

In the embodiment illustrated in FIG. 44, another embodiment of an RF system 820 is shown, one long expandable section makes up the expandable spline set 822. The spline set 822 preferably comprises splines having one or more electrode elements 826. To support the length during treatment, a balloon 824 is placed inside the spline set and is shown in FIG. 44. For example, this balloon 824 may use an internal lumen of the catheter (not shown) for inflation and deflation. Alternatively, the balloon 824 can be a separate device inserted into the long expandable spline set 820. Alternatively, open cell foam can be used in place of the balloon as the expanding component. The foam can be collapsed by a sheath, and by sliding the sheath proximally, the foam could expand as it is uncovered.

As discussed above with respect to the fixed diameter electrode element systems, spline electrode elements, when individually wired for power, may be used in conjunction with a multiplexing process. Such an embodiment allows for the sequential or "cascading" heating of specific active electrode element subsets of the spline set. This may involve energizing at least one spline for a specific dwell time and then cascading axially or moving to the next adjacent spline(s) or electrode element(s) until the end spline or electrode element is reached. The cycle is then repeated until the complete treatment time is reached. Multiplexing can be used with monopolar or bipolar configurations of electrode element subsets. For a monopolar mode, a ground pad or virtual electrode is used in conjunction with active spline electrodes powered by the multiplexer. For a bipolar mode, adjacent electrodes on each spline are powered for treatment along each spline. In another embodiment, adjacent splines are bipolar so that spline pairs treat the vein along the spline length. In one embodiment, an active spline and two return splines are powered to treat the hollow anatomical structure.

A balloon can also be used to expand and collapse the electrode elements. The balloon preferably displaces blood from lumen being treated and can reduce the amount of coagulum build-up on the inside of the heating element. Minimizing coagulum build-up during the collapse and removal of the device is advantageous. In one embodiment, the balloon occludes the vessel, impairing blood flow and subsequent coagulum build-up to facilitate device removal. The balloon can act as a support structure for the outer electrodes to enhance vein wall apposition.

Figure 45:
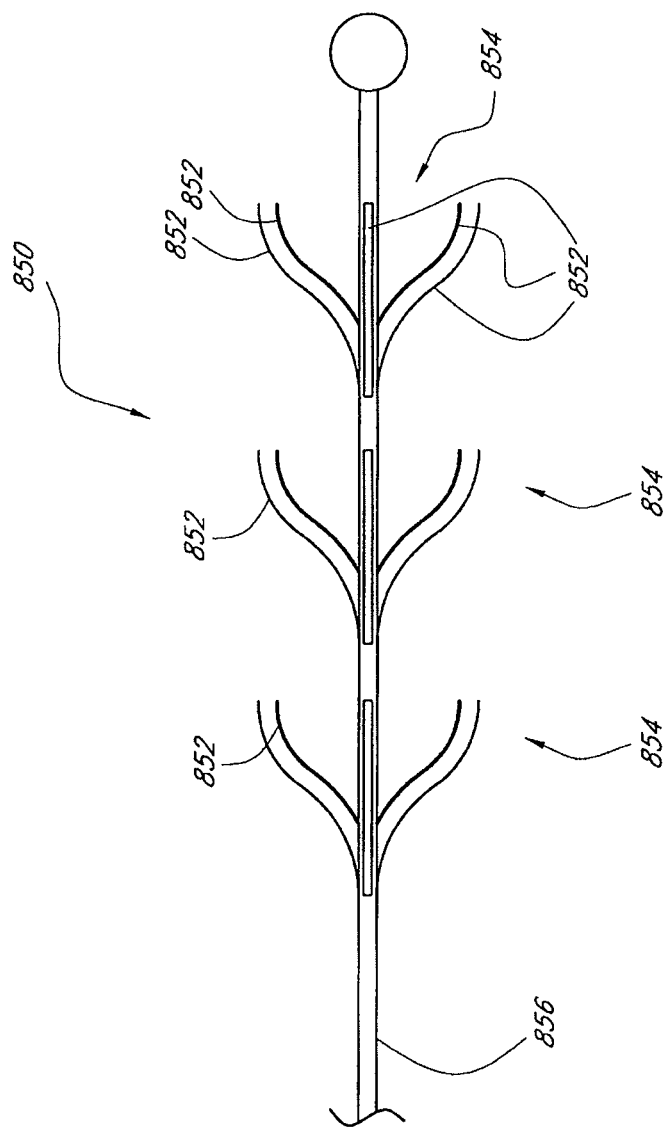
FIG. 45 illustrates an exemplary embodiment of an expandable set of cantilevered spline electrodes capable of conforming and contacting a vein wall.

FIG. 45 is another embodiment of the working end 850 of a catheter, using one or more expandable splines 852 in spline sets 854. In the illustrated embodiment, the splines 852 are cantilevered, being attached to the catheter 856 at one end. The cantilevered electrode preferably is only active at the distal tip portion. The arm of the electrode is electrically insulated. The pre-shaped spline sets 854 are axially spaced apart. A sheath cable used to control the collapsed and expanded positions of the electrodes. The sheath can also be used for placement and removal of the device. In some embodiments, it can be used to set the treatment length. For example, where there is more than one set of splines on the device, the sheath can be selectively withdrawn to expose a desired number of spline sets to treat a desired length of tissue.

A temperature sensor can be placed on the distal end of the cantilevered spline electrode. In some embodiments, the sensor can be used with the RF power controller described above. The temperature sensor preferably is placed proximal to the treatment zone. In some embodiments the device is used such that the electrodes move or are 'pulled back' during treatment. Using multiple electrode sets preferably reduces the treatment time required. In other embodiments, the device is used in a stationary manner and subsequently moved to another section of the hollow anatomical structure for another treatment.

Figure 46:
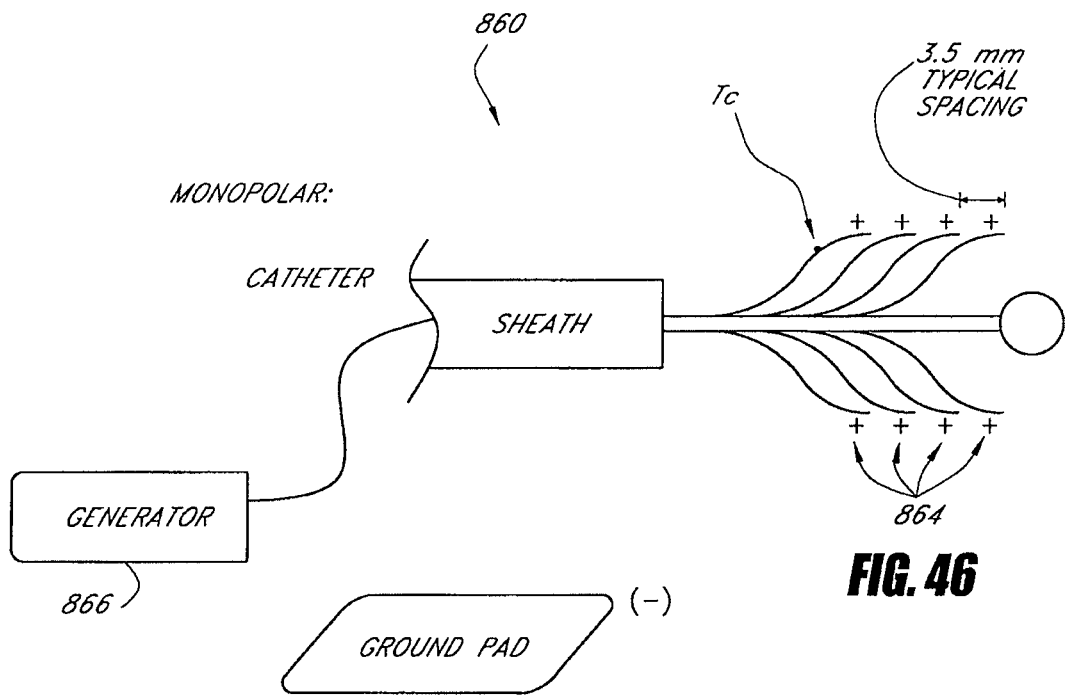
FIG. 46 illustrates another embodiment of the working portion of the catheter of FIG. 45 having a monopolar arrangement.

FIG. 46 shows another embodiment 860, similar to the embodiment of FIG. 45. In this embodiment, the spline sets 864 are configured for monopolar RF. The spline sets 864 are one polarity and a ground pad 866 is used to create the return path through the patient. By using multiple electrode sets, the treatment length can be longer.

Figure 47:
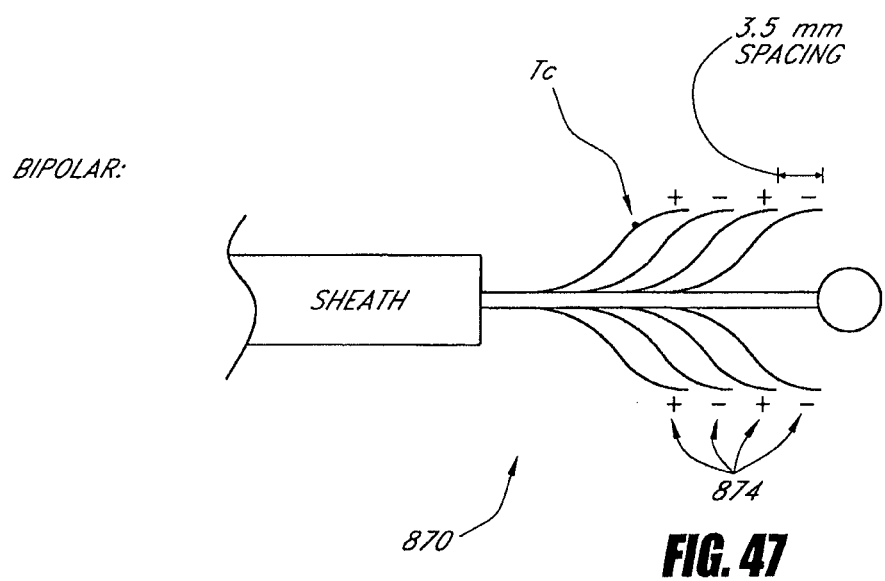
FIG. 47 illustrates another embodiment of the working portion of the catheter of FIG. 45 having a bipolar arrangement.

FIG. 47 shows another embodiment 870 of the device of FIG. 45. The spline sets 874 are arranged for bipolar RF. In this embodiment, each electrode spline set 874 has a different polarity from an adjacent electrode spline set.

The embodiments illustrated in FIGS. 45-47 can be used in conjunction with the multiplexer process when used in a stationary manner.

Figure 48:
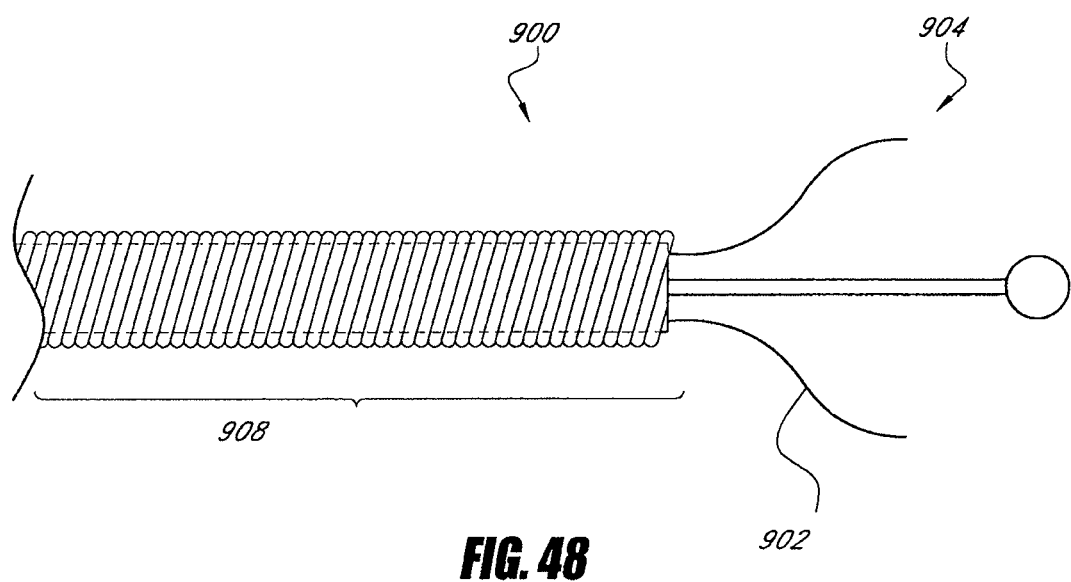
FIG. 48 illustrates another embodiment of the working portion of the catheter of FIG. 45 having a sheath capable of heating a vein wall.
Figure 51:
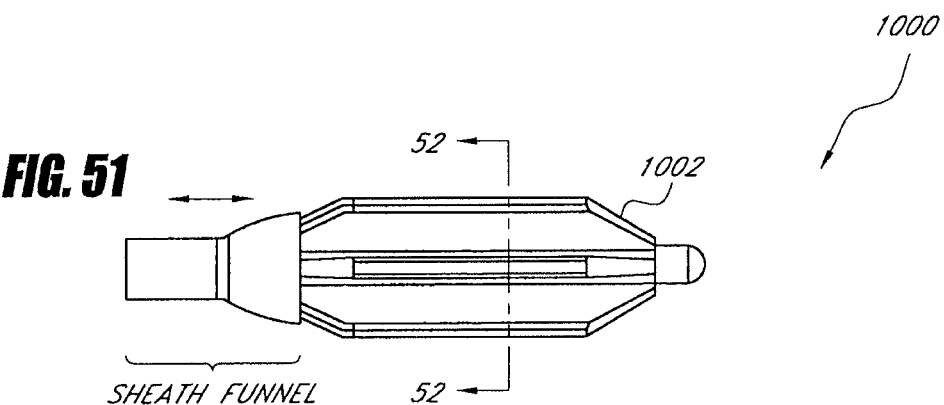
FIG. 51 illustrates another embodiment of a working portion of the catheter body formed from expandable foam.

With reference to FIG. 48, in one embodiment the device 900 has expandable-cantilevered electrodes 902 similar to those described above. The device has one or more electrodes 902 in one or more sets of electrodes 904. Proximal to the electrode sets 904 is a sheath-mounted heating element 908 (e.g., a resistive coil). The proximal heating coil preferably initiates the treatment process and the expanded electrodes preferably complete the treatment process. The effective length of the proximal coil element can be controlled by the use of a sheath component similar to that described above with reference to FIG. 37.

One or more temperature sensors can be placed on the distal end of the cantilevered spline electrodes. The device of the illustrated embodiment can be used with an RF power controller similar to that described above. The temperature sensor preferably is placed proximal to the treatment zone. The device can be used such that the device-electrodes move during treatment. Using multiple electrode sets preferably reduces the treatment time.

Another embodiment of a device 950 shown in FIGS. 49-50 utilizes at least one expandable loop 955 which emanates from the side of the main catheter body. One end 959 of the loop 955 is anchored to the catheter shaft 953. The other end of the loop passes through an opening 956 in the sidewall of the catheter tube 953 and extends through the catheter lumen to the handle (not shown) at the proximal end. This proximal end of the loop acts like a stylet, and is usable to manipulate the loop shape and size. FIG. 49 shows the loop 955 in an expanded or erected configuration suitable for HAS treatment, and FIG. 50 shows the loop 955 in a collapsed or low-profile configuration suitable for passing the device 950 through the HAS. The wire is typically circular in cross section. In one embodiment, the loop is pre-shaped in order to extend outward toward the walls of the hollow anatomical structure and eventually into contact with them. Alternatively the wire section that forms the actual exposed loop portion 954 may be a flat wire, rectangular, ovular, or other geometrical cross section. In one embodiment, rotating the stylet handle end of the loop manipulates, or twists, the loop toward or away from the catheter shaft.

In one embodiment, each loop preferably is individually erectable or powered to match varying hollow anatomical structure diameters providing tailored treatment parameters. In one embodiment, all loops can be of the same length/diameter and can be actuated simultaneously.

The loop 955 may comprise an electrode element similar to the initial embodiment of FIG. 43. For example the loop 955 may comprise active electrode elements 957 located thereon. In addition, each loop may have a temperature sensor on the active electrode element for use in temperature controlled energy delivery. In other embodiments, the active electrodes are of one polarity and use a ground pad as the return electrode for a monopolar setup.

In one embodiment, the active electrodes are bipolar (e.g., comprising a positive and negative pain) on the loop itself. Each loop is used to treat a section of the vein. The number of loops expanded determines the treatment length enabling the device to be adjusted to provide a variable treatment length. In some embodiments, the device is moved and newly placed to treat the adjacent vein wall relative to the initial treatment.

FIGS. 51-54 show various views of an expandable foam component 1000. The foam preferably is conformable to the vein and the rib like sections 1002 preferably can be placed in apposition to the vein wall.

In one embodiment, the foam is all open celled. In another embodiment, portions of the foam are open-celled. Open celled foam allows electrically conductive fluids, such as saline, to flow through it. The conductive fluid is used as a virtual electrode to contact the vein wall.

Figure 52:
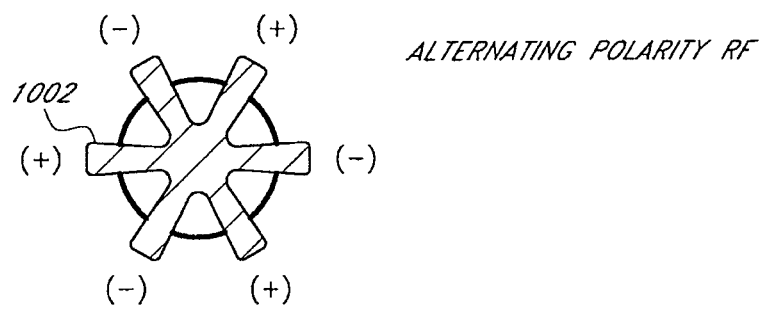
FIG. 52 illustrates a cross-section of the device of FIG. 51.
Figure 53:
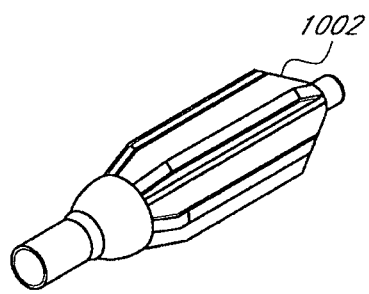
FIG. 53 illustrates a perspective view of the device of FIG. 51.
Figure 54:
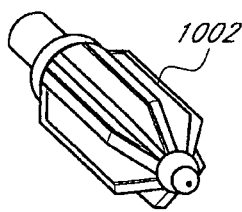
FIG. 54 illustrates another perspective view of the device of FIG. 51.

The foam component preferably has portions that are not open-celled in order to control or direct the conductive fluid flow. This is accomplished by using closed-cell foam or giving the foam surface a skin, which creates a fluid barrier. FIG. 52 shows a cross section 52-52 of the foam component 1000. The ribs 1002 are labeled either (+) or (−) to indicate the alternating polarity. As mentioned above, RF or alternating voltage doesn't have polarity, but the figures show it in order to help describe the device. The ribs 1002 preferably have a top edge surface exposed for fluid flow. The embodiment shown in FIG. 52 is for a bipolar device. Fluid flow for the (+) polarity and the (−) polarity preferably are maintained as separate systems electrically to avoid shorting internal to the device. In another embodiment, FIG. 52 is monopolar. A single source of conductive fluid is used with a ground pad on the patient.

Figures 55, 56:
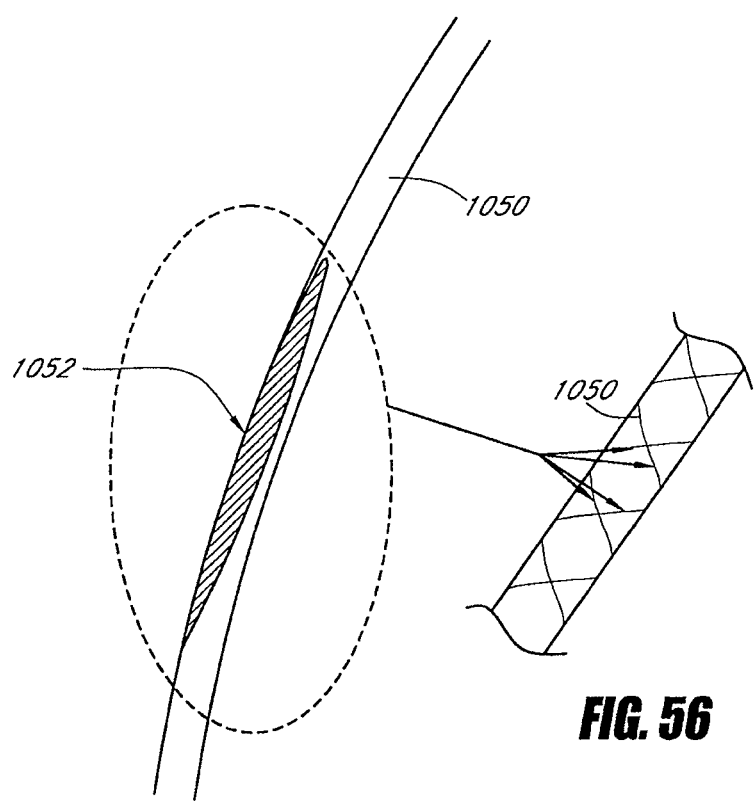
FIG. 55 illustrates another embodiment of an expandable device having an expandable braid electrode.
FIG. 56 illustrates a close-up view of the expandable braid electrode of FIG. 55.
Figure 57:
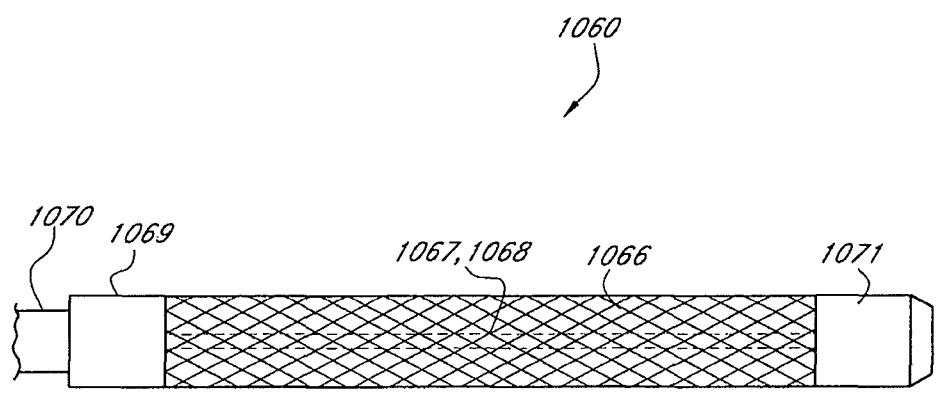
FIG. 57 illustrates another embodiment of an expandable device having an expandable braid electrode.
Figure 58:
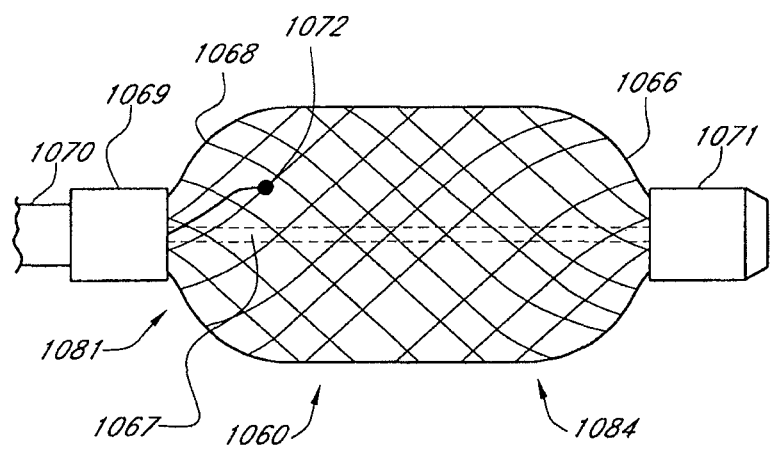
FIG. 58 illustrates the device of FIG. 57 in an expanded configuration.

FIGS. 55-56 and 57-58 show embodiments having a braid component as the working end of the device. These embodiments are expandable and in some embodiments, each can have a sheath there over for use placement of the device. FIGS. 57-58 show a temperature sensor on the braid for temperature control.

FIGS. 55-56 show the detail of a skived window 1052 on a section of the braid wire 1050. The wire is electrically connected and has an insulated jacket on it. The wire insulation can be polyimide, Teflon®, Pebax® or other biocompatible materials, which are stable at the treatment temperatures. Sections of the insulation are removed to expose the wire on the outer circumference of the braid. The method to create the skived window can be mechanical, chemical or by controlled laser or water cutting.

This skived window 1052 creates an electrode from the exposed wire section and places it in contact with the vein wall only. The window creates a skived electrode similar to the checkerboard device electrode, however the individual braid wires 1054 are helically wound in the braid pattern and create a diamond pattern of electrodes. The braid electrode pattern is in apposition to the vein wall and is conformable before and during treatment.

The embodiment 1060 of FIGS. 57-58 utilizes a metal braid wire 1066 as the working active electrode element. This wire is round and made of Nitinol®. However, in other embodiments, the braid wire may be flat wire and/or comprise an alternate spring type material as discussed in earlier sections. For this device, the elastic characteristics of Nitinol® are beneficial to the method of expanding and collapsing the device. In one embodiment, the braid is heat set in the nearly fully expanded position. In other embodiments, a balloon is used to expand the braid.

In one embodiment, the braid wire is sleeved in polyimide to isolate the wires from each other where they overlap as well as to create the skived electrode. The braid component can be created using standard braiding technology. Alternatively, a single wire may be woven into the braid component. The method is relevant for the overall resistance or impedance of the device for the energy source.

The proximal and distal ends of the braid 1066 component are captured in a two-part crimp sleeve, 1069 and 1071, in order to anchor the ends to the catheter tube 1070 and stylet 1067. The braid 1066 in this embodiment is expanded by the use of the catheter stylet 1067, which runs the internal axial length of the catheter, from the distal tip 1071 to the proximal handle (not shown). The proximal end of the stylet passes through a Touhy Borst type fitting on the catheter handle and in turn is a handle for stylet manipulation. In this case, pushing the stylet distally collapses the braid (illustrated in FIG. 57), while pulling the stylet 1067 expands the braid (illustrated in FIG. 58).

In the embodiment of the invention illustrated in FIGS. 57-58, a balloon 1068 is placed internal to the braid 1066 such that the ends are distal to the crimp section 1069 and proximal to the crimp 1071. As previously discussed, the balloon 1068 is silicone, but can be other materials previously identified. This balloon then uses internal lumen and side port (not shown) of the catheter stylet 1067 for inflation and deflation. The balloon can also be used to displace blood from lumen being treated to prevent coagulum build-up on inside of heating element, help direct heat radially outward to the vein wall and provide a support structure for the outer heating element ensuring vein wall apposition.

It should be noted that the typical silicone extrusion may expand axially and radially when inflated. This causes the balloon to become "S" shaped for a set axial length of tubing, thus causing the braid to have non-uniform tissue apposition with the hollow anatomical structure. To compensate for this issue, the extrusion 1068 may be pre stretched axially just prior to anchoring on the catheter tubing to the stylet component 1067. The stretched tube may then expand radially with little to no axial expansion, depending on the amount of pre-stretch achieved. The balloon may be used to occlude the vessel to impair blood flow and to remove blood from the braid portion of the catheter. This creates a static fluid volume and makes the heat treatment more efficient. Also, the balloon promotes braid apposition with the hollow anatomical structure. In other embodiments, the balloon is at least partially expanded and contracted through expansion and compression of the ends 1081, 1084.

In one embodiment, a temperature sensor 1072 is attached to the braid wire along its axial length. The sensor 1072 may be used for temperature control during the application of energy for the controller. Although the sensor 1072 is shown attached near the proximal end of the braid wire, the sensor 1072 may be located along other portions of the braid wire. In addition, more than one sensor may be used.

In another embodiment, the balloon is a separate device from the braid device. For example, the balloon device may fit within the lumen of the braid device, and the tips of both devices may connect and anchor to one another. For example, the anchor mechanism may include a set of male and female threads appropriately sized. Alternatively, the device tips may be anchored together by use of axially aligned holes in both tips through which a wire is placed and tied off. Alternatively, the tips may be designed with a spring ball detent to anchor the tips together. Alternatively, strong magnets of opposite polarity may be used to locate the tips and hold them together.

As discussed above for the fixed diameter electrode element, the skived electrode wires, when individually wired for power, can be used in conjunction with the multiplexing process. This allows the heating of specific active electrode element subsets of the braid wire set. In one embodiment, at least one braid wire is energized for a specific dwell time and cascades or moves to the next braid wire until the end braid wire electrode set is reached. The cycle is then repeated until the complete treatment time is reached. The multiplexing can be used for monopolar or bipolar configurations of braid wire electrode sets. For a monopolar mode, a ground pad preferably is used in conjunction with active braid wire electrodes powered by the multiplexer. For a bipolar mode, adjacent braid wire electrode sets are powered for treatment. Alternatively, adjacent braid wires can be bipolar so that the pairs treat the vein along the braid length. Alternatively, one active braid wire and the two adjacent return braid wires can be powered to treat the vein wall.

FIGS. 59 and 60 are a side view and a tip view of one embodiment 1100 having four expanded splines 1102 with electrodes 1104. One or more splines 1102 can be made of Nitinol®, or similar matter. The device preferably is configured to place the ball electrodes 1104 in apposition to a vein wall. One end of the spline set 1106 preferably is free enabling the electrode set to adjust and collapse as the treatment shrinks the vein.

Alternatively, the electrode set can be collapsed to a smaller diameter by moving the proximal end of the spline set axially in a proximal direction. A pull wire can be used to move the proximal end.

In another embodiment the proximal end is anchored and the electrode set is collapsed or expanded distally in the axial direction. A sheath can be used to expand or contract the electrode set.

FIGS. 61-64 are additional embodiments using a pre-shaped Nitinol® wire for vein conforming. The device 1120 is shown in several configurations. FIG. 61 shows a sheath 1122 and a wire 1124 in a first low-profile configuration. FIG. 62 shows the wire 1124 in an activated configuration. FIG. 63 is another embodiment 1130, similar to the embodiments of FIGS. 61, 62, except that the activated wire 1134 has a different configuration. The wire 1144 of the embodiment 1140 of FIG. 64 has a double wire configuration. These configurations are shown as two dimensional forms, however, the pre-shaped wire can have a three-dimensional or helical shape. The pre-shaped form can be heat activated or can comprise a shape memory material. In one embodiment, ball electrodes are placed on the outer radiuses of the serpentine like curves for vein wall contact.

Figure 65:
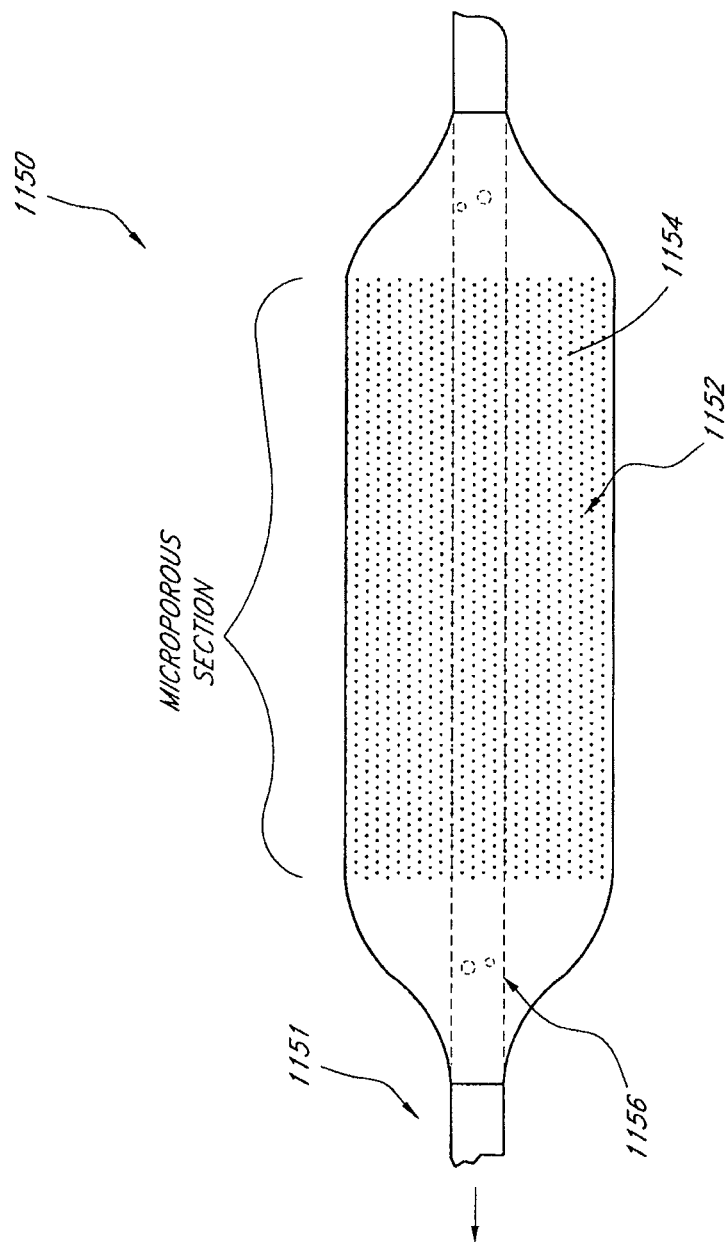
FIG. 65 illustrates another embodiment of an expandable device having an expandable balloon with a micro porous surface.

FIG. 65 is another embodiment 1150 using an expandable balloon-type electrode as the working end of the catheter device 1151. The cylindrical balloon surface 1152 has micro porous holes 1154 in the wall in a defined section. The balloon preferably is made of a PET (polyethylene terephthalate) or other suitable material. The balloon wall preferably is placed in apposition to the vein wall for treatment. In one embodiment, electrically conductive fluid is used to treat the hollow anatomical structure. The micropores permit the conductive fluid to contact the inner wall(s) of the hollow anatomical structure in which the catheter is deployed. An electrode internal to the balloon uses electrically conductive fluid, such as saline, to create an electrical path through the porous balloon surface from fluid ports 1156. The electrical path continues through the tissue to a ground pad on the patient when a monopolar system is used. In one embodiment, a temperature sensor is placed on the balloon surface in the micro porous section for temperature controlled treatment.

In some embodiments, the distal portion of the catheter is collapsible to allow diametrical reduction of the hollow anatomical structure towards the catheter shaft. As the hollow anatomical structure is reduced, the distal catheter portion moves with respect to the catheter shaft in a radially collapsing direction. This movement preferably is monitored and/or conveyed to the handle to signal the end of treatment. In some embodiments, a pre-set axial migration of the distal portion is correlated to a specific lumenal reduction.

Except as further described herein, any of the catheters and/or devices or components of these catheters or devices disclosed in FIGS. 30-65 may, in some embodiments, be similar to any of the catheters described in U.S. Pat. No. 6,401,719, issued Jun. 11, 2002, titled METHOD OF LIGATING HOLLOW ANATOMICAL STRUCTURES; or in U.S. Pat. No. 6,179,832, issued Jan. 30, 2001, titled EXPANDABLE CATHETER HAVING TWO SETS OF ELECTRODES; or in FIGS. 1-26 herein; or in U.S. Provisional Patent Application No. 60/613,415, filed Sep. 27, 2004, titled RESISTIVE ELEMENT SYSTEM. In addition, any of the catheters and/or devices or components of these catheters or devices disclosed herein may, in certain embodiments, be employed in practicing any of the methods disclosed in the above-mentioned U.S. Pat. Nos. 6,401,719 or 6,179,832, or in FIGS. 1-26 herein, or in the above-mentioned Provisional Application No. 60/613,415. The above-mentioned U.S. Pat. Nos. 6,401,719 and 6,179,832 and Provisional Application No. 60/613,415 are hereby incorporated by reference herein and made a part of this specification.

Figure 66:
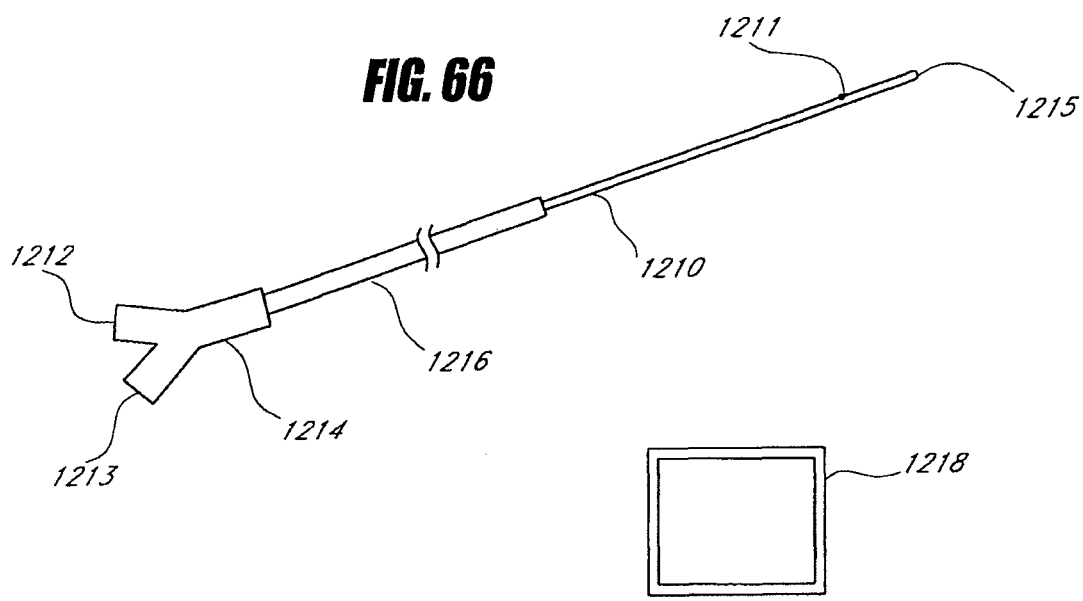
FIG. 66 is schematic view of one embodiment of a device for conforming a hollow anatomical structure (HAS) to a desired shape.

Shown in FIG. 66 is a catheter for applying energy to a hollow anatomical structure (HAS). The catheter includes a catheter shaft 1210, a sheath 1216, a sensor 1211, a tip 1215 and a handle 1214. The handle has an open port 1212 for fluid infusion and/or guidewire introduction, and a connection 1213 for interfacing with an energy source 1218.

The catheter shaft 1210 can be comprised of a biocompatible material preferably having a low coefficient of friction, such as polyimide, Teflon®, Hytrel® or other suitable material. The catheter shaft can be sized to fit within a hollow anatomical structure (HAS) between 6 and 8 French, which corresponds to a diameter of between 2.0 mm (0.08 in) and 2.7 mm (0.10 in), or other sizes as appropriate. The catheter shaft 1210 is used to maneuver the distal portion of the catheter during placement.

The retractable sheath 1216 exposes the distal portion of the device that applies energy to the HAS. The sheath can be employed to protect the device during placement, facilitate introduction of the device and/or adjust the exposed axial length for a desired treatment length. The sheath can be made from a biocompatible material preferably having a low coefficient of friction, such as polyimide, Teflon®, Hytrel® or other suitable material.

The distal portion of the device transfers electrical energy to the HAS for treatment. This portion may have a heating element that directly heats the HAS through heat conduction from the catheter shaft to the wall tissue. This portion may also incorporate a set of electrodes that deliver RF energy to the HAS and thereby generate heat within the HAS. This energy can be delivered up to a predetermined temperature or power level.

An atraumatic tip 1215 can be attached to the distal-most catheter end. The tip facilitates manipulation of the catheter through the HAS. The tip is preferably tapered inward at its distal end or is "nosecone" shaped, however, it can have other shapes that facilitate tracking of the catheter over a guide wire and through the bends and ostia in the vascular system. The nosecone-shaped tip can, for example, be fabricated from a polymer having a soft durometer. In some embodiments, the tip can be fabricated from polymers having durometers between about 60 and about 90 Shore A. In other embodiments, the tip can be fabricated from polymers with durometers between about 70 and about 80 Shore A, and in one preferred embodiment, a material with a durometer of about 70 Shore A is used.

A sensor 1211 can be attached to the exterior of the distal catheter shaft; this sensor can sense values pertinent to measuring the treatment's progress, such as temperature, impedance, or other pertinent treatment parameters. A single sensor 1211 is shown as part of the heating element; there can also be multiple sensors placed along the axial catheter length. The parameter measured will typically be that of the HAS tissue itself. The energy system 1218 can be employed to monitor the individual sensors and use the multiple inputs for feedback. The controller can be employed to monitor for high or low signals, and the microprocessor can be employed to determine the energy output accordingly. This control feedback mechanism may facilitate a more appropriate amount of energy to effectively and safely treat the HAS.

Figure 67:
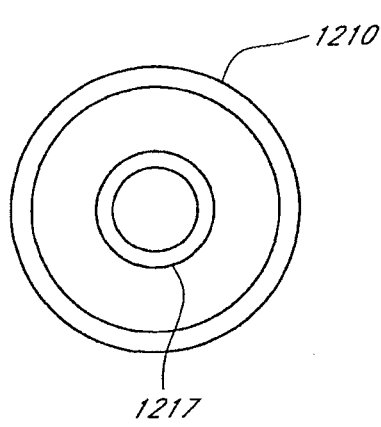
FIG. 67 is a cross-sectional view of the device of FIG. 66.

The handle houses an open port 1212 that directly communicates with an inner lumen extending the entire catheter length. FIG. 67 depicts the inner lumen 1217 contained within the catheter shaft 1210 that communicates with the handle open port 1212. The catheter can be periodically flushed with saline through the port; flushing prevents the buildup of biological fluid, such as blood, within the catheter shaft.

The treatment area of the HAS can also be flushed with a fluid such as saline through the inner lumen 1217 in order to evacuate blood from the treatment area of the HAS so as to prevent the formation of coagulum and subsequent thrombosis.

When the energy delivery method is an RF-based system, the use of a dielectric fluid (e.g., disposed within or around the HAS) can minimize unintended heating effects away from the treatment area. The dielectric fluid prevents the current of RF energy from flowing away from the HAS, instead it concentrates the energy delivered to the intended target. Any suitable dielectric fluid can be used as desired, for example dextrose is often used as a dielectric fluid in medical treatment contexts.

Alternative endolumenal implementations of fluid that can be delivered through the inner lumen 1217 might include drug therapies that promote fibrotic growth post endothelial layer destruction, such as TGF (Transforming Growth Factor) which is widely known to promote fibrotic reactions.

The inner lumen 1217 may also allow for the delivery of sclerosants to the interior of the HAS through an outlet at or near the distal end. Sclerosants typically denude the endothelial layer to damage and scar the inner HAS and further facilitate treatment of the HAS together with electrical energy delivery. Sclerosants, such as Polidocanol, hypertonic saline and Sclerodex or other chemical solutions with appropriate toxicity to endothelial cells are widely known in the art.

Finally, a guidewire can also be introduced through the inner lumen 1217 to facilitate catheter navigation to the desired treatment site. The guidewire is advanced to the treatment site prior to catheter advancement; once in place, the catheter is advanced over the guidewire to the treatment site.

Figure 68:
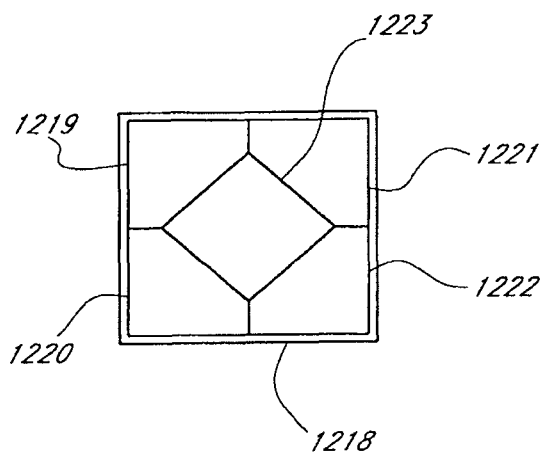
FIG. 68 is a schematic view of an embodiment of an energy source for use with a HAS conforming device.

The handle 1214 also houses an electrical connection that connects the energy system 1218 to a single or plurality of leads traveling down the catheter shaft. These leads may transfer direct thermal heat, or they may be switched as desired to operate in either a bipolar or a monopolar RF-based configuration. The number of leads can be dependent on the size or diameter of the HAS to be treated; larger vessels may require more leads to ensure proper current density and/or heat distribution. FIG. 68 shows the energy system 1218 is made up of an energy source 1223, a microprocessor 1219, a controller 1220, a feedback mechanism 1221 and a visual output 1222.

The energy source 1223 is typically an AC (alternating current) power supply like an RF generator, or a DC (direct current) power supply. The DC power source may also be disposable in form such as a battery. Alternate energy sources may also comprise a laser, microwave, ultrasound, high-intensity ultrasound or other source.

The controller 1220, receives data from the feedback mechanism 1221 and modifies the energy delivery accordingly. The feedback mechanism may receive data from the sensor 1211, for example, and the controller may modify the energy source to supply heat to the HAS at a pre-set parameter. In an alternate embodiment, the user can select a constant power output; the user can then manually adjust the power output relative to the visual output 1222 from the sensor 1211 located at the working portion of the catheter.

The microprocessor 1219 works in conjunction with the controller to provide the algorithm by which the feedback data is processed.

The visual output 1222 can be employed to provide visual verification of critical values obtained during treatment of the HAS.

Figure 69:
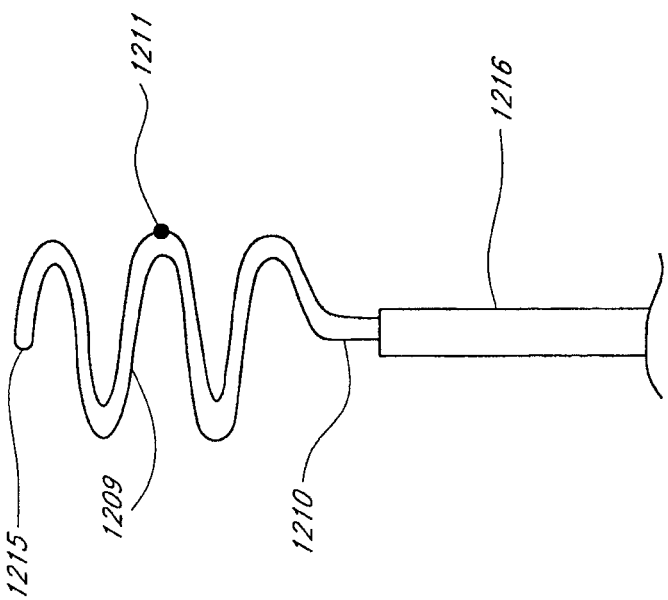
FIG. 69 is a schematic view of an embodiment of a HAS conforming device in which a distal end of the device is expanded outside of a sheath.

FIG. 69 shows a first embodiment of the catheter design with a distal portion 1209 that transfers the energy directly to the HAS when expanded. In this configuration, the distal portion is pre-formed into a planar serpentine shape that stretches the opposing walls of the HAS outward until the top & bottom are forced together and collapsed onto the distal portion. In this expanded shape, the device can be at, for example, a minimum planar thickness range of 2 Fr to 10 Fr (0.66 mm to 3.3 mm) and maximum width range of 3 mm to 25 mm. The intent is to expand and flatten the HAS to approximately the thickness or diameter of the catheter distal portion. An example of a serpentine section is a device distal portion which is 4 Fr or 1.33 mm in diameter with a possible expansion width of 20 mm. A specific example would be to place a 5 Fr or 1.67 mm diameter device in a 8 mm diameter vein. The device then expands and in turn decreases the top to bottom height of the HAS from 8 mm down to 1.67 mm or about a 380% reduction. This would also push the side wall portions of the HAS out to a maximum of about 10-12 mm width. If the HAS is smaller, naturally the percentage reduction will be less and vise versa.

Figure 70:
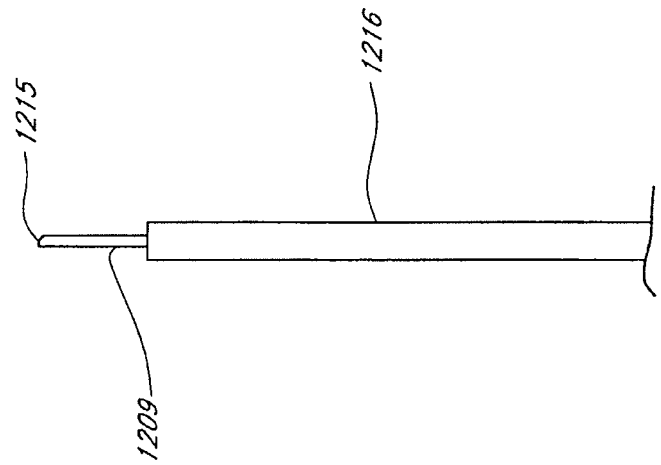
FIG. 70 is an alternate view of the device of FIG. 69 in which the working end of the catheter is withdrawn within the sheath.

FIG. 70 shows the distal portion of the catheter shaft retracted within the sheath 1216. Once within the sheath, the pre-formed curve of the distal portion is overcome by the column strength and radial strength of the sheath. In this retracted or compressed state, the catheter is at full length and minimum width (diameter) and can be introduced into the HAS prior to treatment as well as be removed from the HAS after treatment has been completed.

Figure 71:
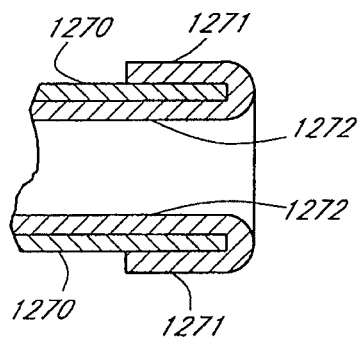
FIG. 71 is a cross-sectional detail view of an embodiment of the sheath portion of FIG. 69.
Figure 72:
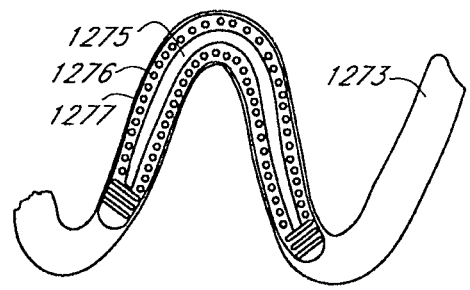
FIG. 72 is a partial cross sectional view of an embodiment of the distal portion of an HAS conforming device.

FIGS. 71 and 72 show cross sectional detail portions of a version of the distal portion 1209, shown in FIG. 69. FIG. 71 shows a sectional view of the distal portion of the sheath. The main tube lumen 1270 is lined with a low friction material 1271 such as Teflon FEP. This liner lets the deformable distal portion 1209 of the device to retract and compress or release and expand with reasonable handling forces. The distal portion 1209 of the device may also have a low friction surface 1277 as well as using similar materials as the outer surface. The internal liner 1272 may be of the same material as the low friction material 1271 or comprise a different material. FIG. 72 shows a cross section of the distal portion 1209 of the device. The main stiffener component 1275 of the device shapes the distal section and is made of materials such as (but not limited to) Nitinol or similar nickel based spring alloys, other spring alloys, 17-7 stainless, Carpenter 455 type stainless, beryllium copper, or shape-memory materials. The intent of the stiffener is to physically conform the HAS to a substantially planar shape, yet be flexible enough to collapse into the device sheath with reasonable handling forces. The cross section of component 1275 could be round, rectangular, or some other shape. Flat or rectangular wire when used for component gives flexibility for conformability and good planar stiffness when expanded. The heating element 1276 is placed on the electrically insulated stiffener 1275 and covered by an insulated outer sleeve 1273, which can be made of a material such as Teflon or FEP.

Figure 73:
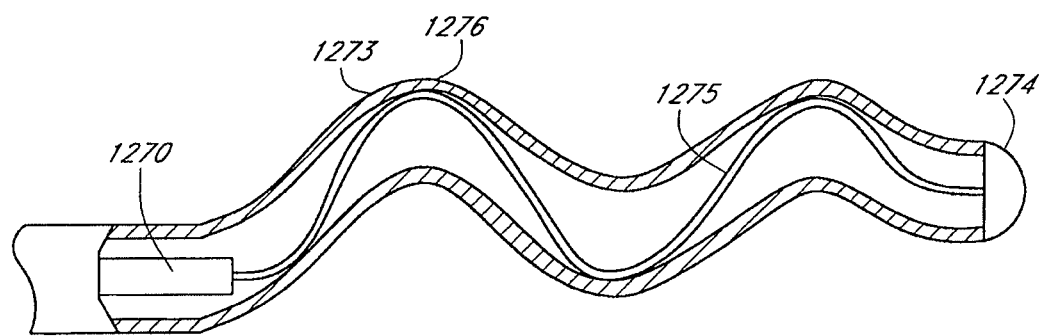
FIG. 73 is a cross-sectional view of another embodiment of a HAS conforming device.

Alternatively, a softer distal tube section could be used which would be more flexible. In this configuration shown in FIG. 73, the coil heating element is on the outer surface of this tube and has gaps between the coils for flexibility of the distal tube. A pre shaped Nitinol wire 1275 resides within the internal lumen of 1273. The proximal end of the shaped wire is anchored to the proximal handle 1214 as a slidable knob while the distal end of the same wire is attached the tip of the catheter tube by a blunt tip 1274. The hypo-tube 1270, acting similar to a sheath, can be coaxial to the Nitinol wire 1275 and catheter tube 1273. The hypo-tube 1270 is moveable distally along the shaped wire. This hypo-tube component 1270 is actuated from the proximal handle end. The hypo-tube can be the length of the catheter or use a stylet type wire connected between it and the handle mechanism. Similar to the embodiment of FIG. 69, the hypo tube can slide over the stationary shaped wire to straighten it. As previously mentioned in the collapsed form the catheter can be used for initial placement, adjustment or removal from the HAS.

FIG. 74 shows a second embodiment of the design in which the distal portion 1209 can be formed by actuation of a distally-anchored wire, which may be pushed or pulled. The distal portion 1209 can be formed with a slight curve bias to achieve this shape when actuated at the handle.

FIG. 75 shows a cross-sectional view of the catheter shaft 1210 within the sheath 1216. The actuation wire 1232 is housed within a dedicated actuation wire lumen 1230 which extends to the distal portion of the device. At the point in which the formed distal portion 1209 begins, the actuation wire 1232 is then suspended on the distal catheter shaft via evenly spaced-apart rings 1231. In this expanded shape, the device is preferably at minimum length and maximum width.

FIG. 76 shows an alternate version of the catheter distal tube portion 1209. The distal tube is free from anchors to create the planar predefined curved shape. The stylet wire is hinged to the tip 1274, so that the distal tip is free to adjust based upon the actuation of the stylet wire. In this configuration the actuation wire 1232 is stiff and controls the pre-shape wire length. By moving the actuation wire proximally, the straight distal section shown in FIG. 76 becomes one of the versions shown to the right of FIG. 76. Moving the actuation wire 1232 proximally will straighten the curved distal portion out. As shown on the right side of FIG. 76, one or two preformed curve distal sections can be used in various shapes to get increased contact to the HAS.

In another embodiment shown in FIG. 77, the planar multiple curve shape is defined by the cut pattern in a hypo-tube component. The cut pattern will determine the shape and the amount of curvature possible, and, as illustrated, various cut patterns may be used. The hypo-tube wall thickness and the depth of cut can affect the stiffness and flexibility of the curve as well. The shape that the cut hypo-tube component may assume can be any shape that will facilitate the purposes of conforming the HAS to the device. For example, the component may assume a helical shape or a serpentine shape, as illustrated in FIG. 77A. The cut hypo-tube could utilize the pull wire 1230 as shown in FIG. 74 for conformal shaping or alternatively the cut hypo-tube could be shape set by using materials such as Nitinol or a spring alloy which can be heat set for shape. By use of an outer sheath, the shape set distal portion would be expanded or collapsed like the device in FIG. 69.

Figure 78:
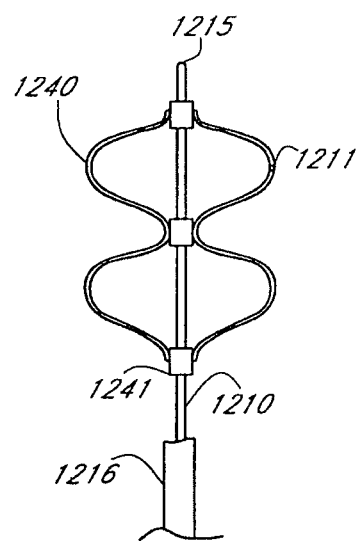
FIG. 78 is a schematic view of another embodiment of an HAS conforming device in which the working end of the catheter is expanded outside the sheath.

FIG. 78 shows a third embodiment of the catheter in its expanded state, or the state at which the catheter is ready to transfer energy to the HAS. The distal portion is comprised of a plurality of rings 1241 slidably disposed on the catheter shaft 1210. Typically, at least one of the rings 1241 is fixed relative to the catheter shaft so that one or both of the remaining rings can be slid towards or away from the fixed ring(s). Attached to the rings 1241 are two ribbon-like elements 40 that transfer energy to the HAS. The ribbon elements can have a cross-section that facilitates the desired outward planar expansion—such as rectangular, elliptical, etc.—when actuated. The ring/ribbon array can be attached to the catheter shaft at its distal end allowing outward planar movement when an actuation rod (not shown), attached to the proximal end of the ring/ribbon array, is actuated.

The ribbon elements 1240 can be made of an electrically-resistive material, such as nickel chromium, copper, stainless-steel, Nitinol®, Alumel® or other suitable materials, that heat when an energy source is applied. This mode of energy transfer would be direct heat conduction to the HAS tissue. The relative resistance or impedance of the resistive element is designed to be optimized for the energy source 1223. The resistive element will depend on the catheter diameter, the energy required, and the energy source requirements.

The ribbon elements 1240 and catheter shaft 1210 can also be used as electrodes to facilitate an RF-based treatment. In this embodiment, the ribbon elements 1240 would be made of a conductive material, such as those already discussed in the previous paragraph. In one scenario, the ribbon elements 1240 could be positively charged, and the catheter shaft could be negatively charged. In a second scenario, one of the ribbon elements could be positively charged, and the other ribbon element could be negatively charged. In a third scenario, both ribbon elements and the catheter shaft could both be positively charged to facilitate a monopolar RF-based treatment.

Figure 79:
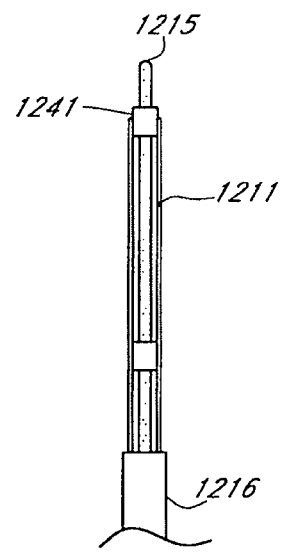
FIG. 79 is an alternate view of the embodiment of FIG. 78 in which the working end of the catheter is withdrawn within the sheath.

FIG. 79 shows the same embodiment in its "compressed" state, or the state prior to treatment in which the catheter is introduced into or removed from the HAS. In the arrangement, the actuation rod (not shown) has been moved with respect to the distal catheter tip to facilitate collapse of the ribbon elements. The sheath 1216 can then be advanced towards the distal tip to protect the ring/ribbon array.

Figure 80:
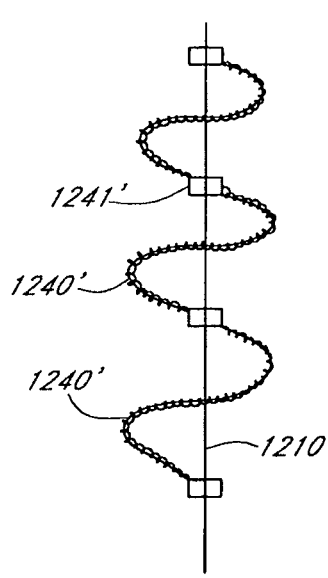
FIGS. 80-82 depict alternate embodiments of the device in FIG. 79.
Figure 81:
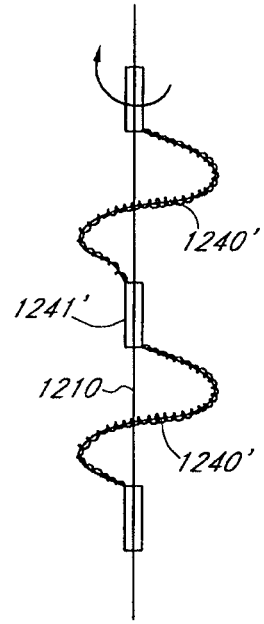
Figure 82:
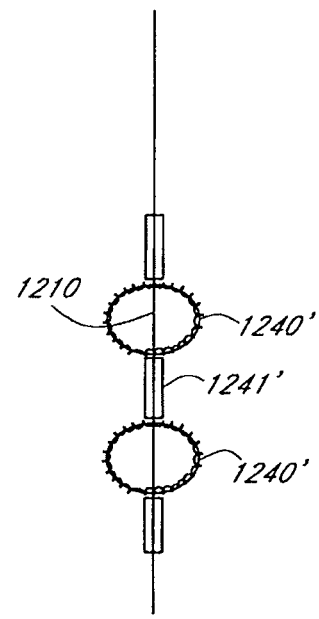

An alternate embodiment is shown in FIG. 80. The ribbon elements 1240 of FIGS. 78 and 79 are replaced by a compressible coil like spring 1240' made of resistant material as previously discussed. The coil spring has anchor points 1241' which attach and slide axially to the central catheter shaft. The actuation rod is internal to the catheter shaft and is not shown. As the actuation rod is moved proximally relative to the catheter main body, the coil spring 1240' elongates as it too moved proximal and becomes linear or straight, as shown in FIG. 79. When the actuation rod is moved distally, the coil spring is expanded in width to form the curves.

In another embodiment, as shown in FIG. 83, a device uses two expandable bow like splines 1240 to reshape and conform the HAS to the device shape. FIG. 83 shows the device collapsed and inside a vein. This device configuration is used for placement or removal from the HAS. FIG. 85 shows the device expanded in the vessel 1250. The planar shape of the vessel 1250 is evident in FIG. 85. In FIG. 86, the broken lines 1240 represent the expanded splines which are in contact with the vein wall, which is shown to be wider than the adjacent sections of this vein 1250. The actuation is accomplished by anchoring the distal portion of each spline 1240 to the catheter tip section. The proximal portion of the spline is attached to an internal stylet wire, not shown, which extends to the proximal end of the catheter. This stylet wire is moveable at the handle 1214 such that it can expand or collapse the splines at the distal tip.

Figures 87, 88, 89, 90:
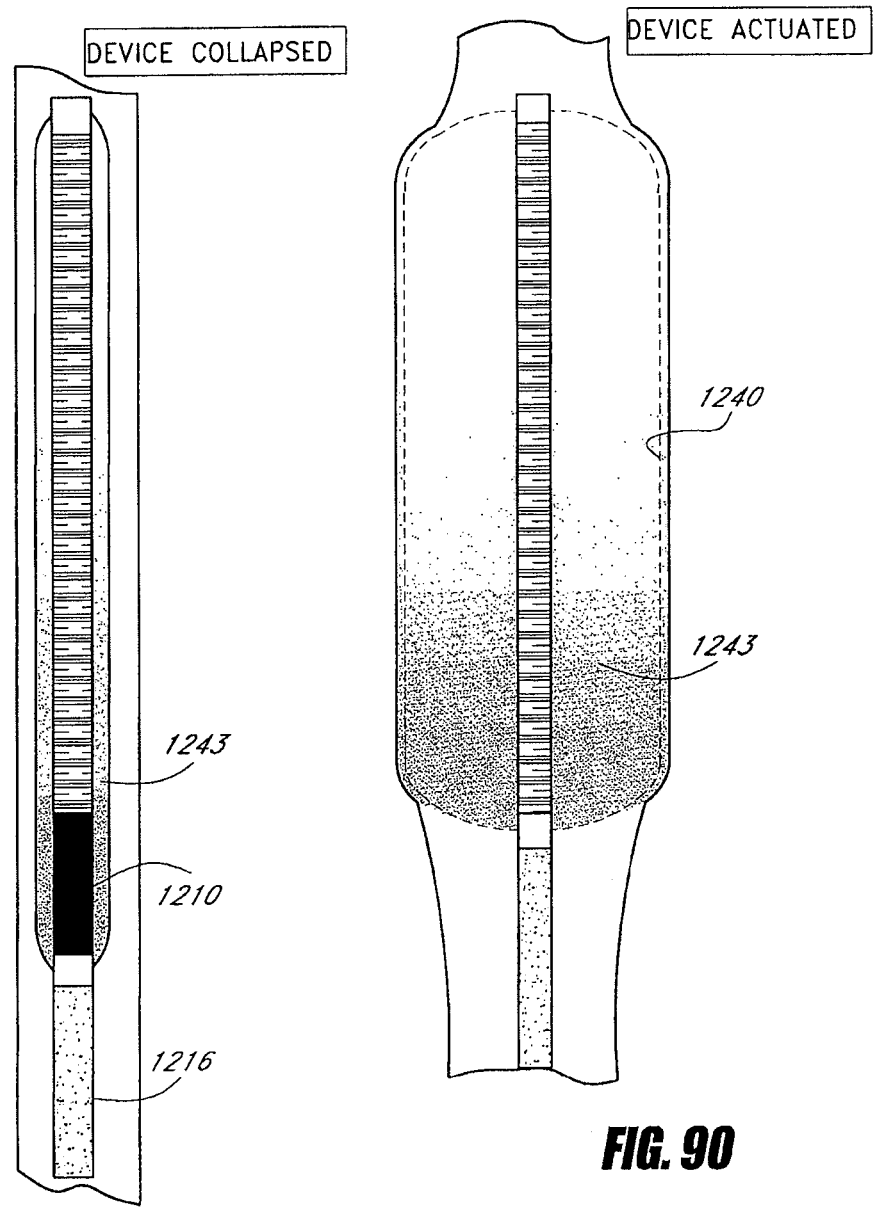
FIGS. 87-90 show schematic views of another embodiment of the device in FIGS. 83-85 in the collapsed and expanded states of the device and respective cross-sectional views of the same.

FIGS. 87-88 show the collapsed device in the vein as previously discussed in connection with FIG. 83. In this alternate embodiment the splines are contained within an elastic film or extrusion made of a material such as silicone. FIGS. 88 and 90 show the elastic film as a gradient shaded section. By expanding the splines, the silicone tube is stretched to a similar cross section as the vein wall in FIG. 85. By encapsulating the splines and catheter tube, the build up of coagulum is greatly reduced and will increase the uniformity of heating.

Figure 91:
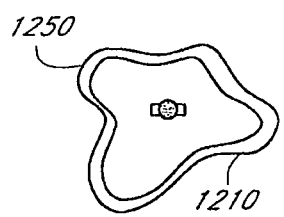
FIG. 91 is a view of a device within a vein in an undeployed state.
Figure 92:
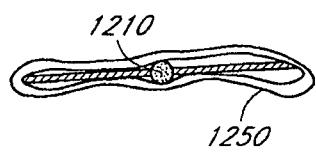
FIG. 92 is a view of a device within a vein in a deployed state.

Shown in FIGS. 91 and 92 are cross-sectional views of the HAS 1250 and distal portion of the catheter shaft 1210 before (FIG. 91) and after (FIG. 92) device deployment. Once actuated, the distal portion of the catheter expands outward in a planar fashion to conform the HAS shape to that of the device. This facilitates direct contact of the HAS with the heating elements of the device.

Figure 93:
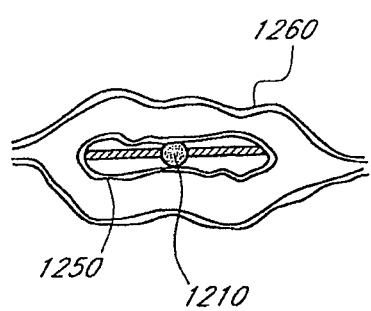
FIG. 93 is a view of a device in a deployed state within a vein and the perivenous compartment.
Figure 94:
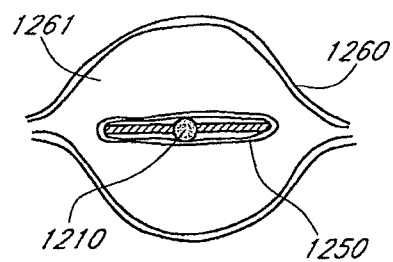
FIG. 94 is a view of a device in a deployed state within a vein and the perivenous compartment in which tumescent has been applied.
Figure 95:
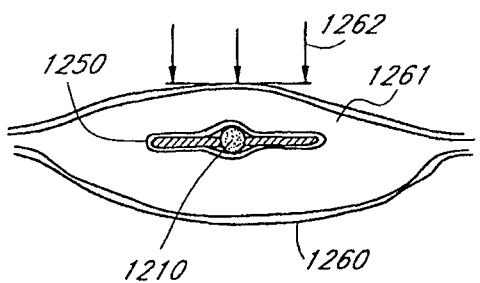
FIG. 95 is a view of a device in a deployed state within a vein and within the perivenous compartment in which tumescent and manual compression have been applied.

To ensure even more complete HAS contact, other means to facilitate HAS wall contact may be applied in the form of tumescent infiltration, exterior manual compression, Trendelenburg positioning, and/or the use of veno-constrictive agents. For example, FIGS. 93-95 show cross-sections of a device's catheter shaft 1210 within a vein 1250 that is within a perivenous compartment 1260. This compartment 1260 is made up of a superficial & deep fascial layers encapsulating the vein and providing a finite three-dimensional space. FIG. 93 shows partial vein wall conformance to the deployed device within fascial layers that are generally non-uniform and unstructured in nature. FIG. 94 shows improved vein wall conformance to the deployed device due to the infiltration of tumescent 1261. Because the perivenous compartment 1260 provides essentially a fixed external envelope, the infiltrated tumescent forces the vein wall further towards the endovenously-placed device. The tumescent essentially provides a circumferentially uniform compressive force inward to the HAS. In FIG. 95, exterior manual compression 1262 is applied from the surface downward onto the perivenous compartment. This provides a non-uniform force causing further perivenous compartment deformation which leads to improved device apposition to the HAS walls. In doing so, more complete vein wall conformance to the deployed device can be achieved. Although FIG. 93 represents an improvement in the art such that device-to-HAS apposition is greatly increased allowing for more effective energy delivery to the HAS, additional compression provided by ancillary methods embodied in FIGS. 93 and 94 might be employed but are not required.

In any of the device embodiments already discussed, the distal portion of the catheter may be collapsible in nature to allow lumenal reduction of the HAS towards the catheter shaft during energy application. As this lumenal reduction occurs, the distal end may move axially, in the proximal direction. Since reduction in HAS diameter typically signals successful application of energy, this axial movement could be monitored and/or conveyed to the handle signaling the end of treatment. In other words, a pre-set axial migration of the distal device portion could be correlated to a specific lumenal reduction. A signal capturing this movement could also be conveyed directly to the energy system as a feedback mechanism to the microprocessor to signal end of treatment to the energy source. The energy source could then stop delivering energy and the visual output could indicate successful and/or treatment end.

In one embodiment, a distal end of an HAS conforming device can be made of a shape-memory material, such as a nickel-titanium alloy. Such a device can be shape set and heat treated such that the device assumes a contracted shape when the material is below a pre-determined transition temperature, and assumes an expanded shape when the material is raised above the transition temperature. In some embodiments, the material can be selected and treated such that the transition temperature is above a patient's normal body temperature, but below an operating temperature of the device. In the case of a resistance-heated device, the temperature of the distal section can be controlled directly.

The first step in facilitating complete vein wall conformance is to introduce the device to the HAS. Once the device is placed in the desired location within the HAS, the device is deployed causing HAS conformance. If applicable and practical, the external compartment is then infiltrated with tumescent agent(s), and externally-placed manual compression is applied directly down onto the HAS. These steps help to promote a more effective treatment by removing HAS conformance inconsistencies due to vessel variability. Likewise, the additional measures of veno-constrictive agents and/or Trendelenburg positioning may be used.

Except as further described herein, any of the catheters disclosed in FIGS. 66-95 herein may, in some embodiments, be similar to any of the catheters described in U.S. Pat. No. 6,401,719, issued Jun. 11, 2002, titled METHOD OF LIGATING HOLLOW ANATOMICAL STRUCTURES; or in U.S. Pat. No. 6,179,832, issued Jan. 30, 2001, titled EXPANDABLE CATHETER HAVING TWO SETS OF ELECTRODES; or in FIGS. 1-26 or 36-65 herein; or in U.S. Provisional Patent Application No. 60/613,415, filed Sep. 27, 2004, titled RESISTIVE ELEMENT SYSTEM; or in U.S. Provisional Patent Application No. 60/621,251, filed Oct. 22, 2004, titled VEIN CONFORMING CATHETER. In addition, any of the catheters disclosed in FIGS. 66-95 herein may, in certain embodiments, be employed in practicing any of the methods disclosed in the above-mentioned U.S. Pat. Nos. 6,401,719 or 6,179,832, or the above-mentioned Provisional Applications Nos. 60/613,415 or 60/621,251. The above-mentioned U.S. Pat. Nos. 6,401,719 and 6,179,832 and Provisional Applications Nos. 60/613,415 and 60/621,251 are hereby incorporated by reference herein and made a part of this specification.

Although invention(s) have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the disclosed invention(s) should not be limited by the particular embodiments described above, but should be determined only by a fair reading of the claims that follow.

What is claimed is:

1. A method of applying energy to a vein, said method comprising:
    providing a catheter configured to emit steam through a plurality of openings along a portion of its length, the catheter comprising:
        a proximal end;
        a working end with a distal tip;
        a perforated outer sheath, including the plurality of openings, near the working end;
        a seal located within the perforated outer sheath and arranged coaxially with respect to the catheter; and
        a fluid chamber having a length extending between the seal and the distal tip;
    selecting a treatment length corresponding to the length of the fluid chamber by adjusting the longitudinal position of the seal, thereby selecting the length of the perforated outer sheath that allows steam to be emitted, wherein selecting the treatment length of a catheter further comprises adjusting a position of an energy element within the internal fluid chamber;
    inserting the catheter into the vein so that the catheter extends longitudinally along the vein;
    heating a fluid;
    applying energy to the vein by emitting the heated fluid as steam from the catheter toward the vein wall; and
    reducing the size of the vein via the applied energy.

2. The method of claim 1, wherein emitting the heated fluid comprises passing the fluid through the openings in the catheter.

3. The method of claim 2, wherein the openings are located on a sidewall of the catheter.

4. The method of claim 3, wherein heating the fluid comprises heating the fluid with a resistance heater.

5. The method of claim 3, further comprising confirming that the vein has been occluded.

6. The method of claim 2, wherein the openings comprise micro-perforations that remain closed until a threshold pressure is reached.

7. The method of claim 1, wherein applying energy to the vein comprises heating the vein wall with the emitted steam.

8. The method of claim 1, wherein heating the fluid comprises heating the fluid inside the catheter with an energy element located within the fluid chamber.

9. The method of claim 1, wherein inserting the catheter comprises positioning the tip of the catheter near the saphenofemoral junction.

10. The method of claim 1, wherein the treatment length is selectable between about 1-60 cm.

11. The method of claim 10, wherein the treatment length is selectable between about 15-45 cm.

12. The method of claim 1, wherein heating the fluid comprises heating the fluid within the chamber.

13. The method of claim 1, wherein selecting the treatment length of a catheter further comprises adjusting the position of the seal with a seal actuation member.

14. A method of treating a vein, said method comprising:
inserting a catheter into the vein so that the catheter extends within the vein along the vein lumen;
heating a fluid in a fluid chamber within the catheter;
emitting the heated fluid as steam from the fluid chamber through a plurality of holes, toward the vein wall, wherein the number of holes emitting steam is selectable by varying the position of a seal within the catheter, wherein the seal defines the proximal end of the fluid chamber, and the seal and the catheter define a common longitudinal axis;
selecting the number of holes to emit steam by moving the position of the seal within the catheter to determine the proximal end of the fluid chamber;
transferring energy to the vein wall with the emitted steam and thereby reducing the size of the vein; and
adjusting a position of an energy element within the fluid chamber.

15. The method of claim 14, wherein the plurality of holes are located on a sidewall of the catheter.

16. The method of claim 15, wherein heating the fluid comprises heating the fluid with a resistance heater.

17. The method of claim 15, further comprising confirming that the vein has been occluded.

18. The method of claim 14, wherein the plurality of holes comprise micro-perforations that remain closed until a threshold pressure is reached.

19. The method of claim 14, wherein heating the fluid comprises heating the fluid with an energy element positioned inside the fluid chamber.

20. The method of claim 14, wherein inserting the catheter comprises positioning the tip of the catheter near the saphenofemoral junction.

21. A method of treating a hollow anatomical structure, said method comprising:
adjusting a position of an internal seal to determine a treatment length of a variable-length fluid chamber within a catheter, the variable-length fluid chamber having a proximal end defined by the position of the seal;
adjusting a position of an energy element within the variable-length fluid chamber;
inserting the catheter into the hollow anatomical structure so that the catheter extends within the hollow anatomical structure along a lumen thereof;
heating a fluid with the energy element in the variable-length chamber at a distal end of the catheter;
emitting the heated fluid as steam from the treatment length of the variable-length chamber, toward the hollow anatomical structure wall; and
transferring energy to the hollow anatomical structure wall with the emitted steam and thereby reducing the size of the hollow anatomical structure.

22. The method of claim 21, wherein emitting the heated fluid comprises passing the fluid through holes in the catheter.

23. The method of claim 22, wherein the holes are located on a sidewall of the catheter.

24. The method of claim 23, wherein heating the fluid comprises heating the fluid with a resistance heater or a laser fiber, wherein the energy element comprises the resistance heater or the laser fiber.

25. The method of claim 23, further comprising confirming that the hollow anatomical structure has been occluded.

26. The method of claim 22, wherein the holes comprise micro-perforations that remain closed until a threshold pressure is reached.

27. The method of claim 21, wherein transferring energy to the hollow anatomical structure wall comprises heating the wall with the emitted steam.

28. The method of claim 21, wherein inserting the catheter comprises positioning the tip of the catheter near the saphenofemoral junction.

29. The method of claim 21, further comprising positioning a distal tip of the energy element at about the longitudinal midpoint of the chamber.

30. The method of claim 21, wherein the seal surrounds the energy element and abuts an inner wall of the catheter, thereby inhibiting proximal leakage of the heated fluid.

31. The method of claim 21, wherein the longitudinal position of the seal is adjusted by an actuation member.

32. The method of claim 21, further comprising introducing fluid into the variable-length fluid chamber through a fluid lumen internal to the energy element.

* * * * *